US008008436B2

(12) United States Patent
Dhurandhar et al.

(10) Patent No.: US 8,008,436 B2
(45) Date of Patent: Aug. 30, 2011

(54) ADENOVIRUS 36 E4 ORF 1 GENE AND PROTEIN AND THEIR USES

(75) Inventors: Nikhil V. Dhurandhar, Baton Rouge, LA (US); Thomas C. Holland, Ann Arbor, MI (US); Zhong Q. Wang, Baton Rouge, LA (US)

(73) Assignees: Wayne State Univeristy, Detroit, MI (US); Board of Sup. of LSU and Agr. & Mechanical College, Baton Rouge, LA (US)

( * ) Notice: Subject to any disclaimer, the term of this patent is extended or adjusted under 35 U.S.C. 154(b) by 9 days.

(21) Appl. No.: 12/095,441

(22) PCT Filed: Nov. 30, 2006

(86) PCT No.: PCT/US2006/045919
§ 371 (c)(1),
(2), (4) Date: Aug. 18, 2008

(87) PCT Pub. No.: WO2007/064836
PCT Pub. Date: Jun. 7, 2007

(65) Prior Publication Data
US 2009/0264356 A1   Oct. 22, 2009

Related U.S. Application Data

(60) Provisional application No. 60/741,399, filed on Nov. 30, 2005.

(51) Int. Cl.
*C07K 14/075* (2006.01)
*A16K 48/00* (2006.01)
(52) U.S. Cl. .................. 530/350; 530/303.1; 424/223.1; 424/93.1; 514/44
(58) Field of Classification Search ........................ None
See application file for complete search history.

(56) References Cited

FOREIGN PATENT DOCUMENTS
WO   WO/2006/086257   8/2006

OTHER PUBLICATIONS

Astrup. A. et al., "Is obesity contagious?" Int J Obes Relat Metab Disord., vol. 22, No. 4, pp. 375-376 (1998).
Atkinson, R.L. et al., "Evaluation of human adenoviruses as an etiology of obesity in chickens," Int J Obesity, vol. 25 (Suppl 2), p. S12 (2001).
Atkinson, R.L. et al., "Human adenovirus-36 is associated with increased body weight and paradoxical reduction of serum lipids," International Journal of Obesity, vol. 29, pp. 281-286 (2005).
Bernard, A. et al., "Brain structures selectively targeted by canine distemper virus in a mouse model infection," J Neuropath Exp Neuro, vol. 52, No. 5, pp. 471-280 (1993).
Bernard, A. et al., "Hyperinsulinemia induced by canine distemper virus infection of mice and its correlation with the appearance of obesity," Comp Biochem Physiol., vol. 91B, No. 4, pp. 691-696 (1988).
Bernard, A. et al., "Localization of viral proteins and RNA in hypothalamus of mice infected by canine distemper virus (French)," Virology, vol. 313, pp. 545-551 (1991).
Burgering, B. M. et al., "Protein kinase B (c-Akt) in phosphatidylinositol-3-OH kinase signal transduction," Nature, vol. 376, pp. 599-602 (1995).
Carter, J.K. et al., Influence of diet on a Retrovirus induced obesity and stunting syndrome, Avian Dis, vol. 27, No. 1, pp. 317-322 (1983).
Carter, J.K. et al., "Rous-Associated virus type 7 induces a syndrome in chickens characterized by stunting and obesity," Infection and Immunity, vol. 39, No. 1, pp. 410-422 (1983).
Cheskin, L.J., "The Pathogens are Speaking: Are We Listening?" Am. Soc. for Nutr. Sc. J. Nutr., vol. 131, pp. 2809S-2810S (2001).
Chiou, G.Y. et al., "Synergistic effect of prostaglandin F2alpha and cyclic AMP on glucose transport in 3T3-L1 adipocytes," J Cell Biochem, vol. 94, pp. 627-634 (2005).
Cornelius, P. et al., "Regulation of glucose transport as well as glucose transporter and immediate early gene expression in 3T3-L1 preadipocytes by 8-bromo-cAMP,".J Cell Physiol., vol. 146, pp. 298-308 (1991).
de Souza, C.J. et al., "Effects of pioglitazone on adipose tissue remodeling within the setting of obesity and insulin resistance," Diabetes., vol. 50,. pp. 1863-1871 (2001).
Dhurandhar, N.V. et al., "Association of Adenovirus Infection with Human Obesity," Obesity Research, vol. 5, No. 5, pp. 464-469 (1997).
Dhurandhar, N.V. et al., "Avian adenovirus leading to pathognomic obesity in chickens," J Bombay Vet College, vol. 2, No. 2, pp. 131-132 (1990).
Dhurandhar, N.V. et al., "Effect of adenovirus infection on adiposity in chicken," Veterinary Microbiology, vol. 31, pp. 101-107 (1992).
Dhurandhar, N.V. et al., "Human Adenovirus Ad-36 Promotes Obesity in Male Rhesus and Marmoset Monkeys," J Nutrition, vol. 132, pp. 3155-3160 (2002).
Dhurandhar, N.V. et al., "Increased adiposity in animals due to a human virus," Int J Obesity, vol. 24, pp. 989-996. (2000).
Dhurandhar, N.V. et al., "Obesity of Infectious Origin: A Review," Growth, Genetics and Hormones, vol. 20, No. 3, pp. 33-39 (2004).
Dhurandhar, N.V. et al., Regulation of Leptin Expression and Secretion by a Human Adenovirus, Obesity Research, vol. 11, p. A38 (2003).
Dhurandhar, N.V. et al., "Transmissibility of adenovirus-induced adiposity in a chicken model," Int J. Obesity, vol. 25, pp. 990-996 (2001).
Douen, A.G. et al., "Exercise Induces Recruitment of the 'Insulin-responsive Glucose Transporter'," J. Biol. Chem., vol. 265, No. 23, pp. 13427-13430 (1990).
Farmer, S.R., "Regulation of PPARgamma activity during adipogenesis,". Int J Obes , vol. 29, pp. S13-S16 (2005).
Farokhzad, O.C. et al., "Nanoparticle-aptamer bioconjugates: a new approach for targeting prostate cancer cells," Cancer Res., vol. 64, pp. 7668-7672 (2004).
Foy, H.M. et al., "Adenoviruses.," in "Viral infections of humans: Epidemiology and control," Evans, Alfred S. Ed. Plenum Medical, New York, pp. 53-70 (1976).

(Continued)

*Primary Examiner* — Bao Li
(74) *Attorney, Agent, or Firm* — McDermott Will & Emery LLP

(57) ABSTRACT

Expression of the E4 orf 1 gene of Ad-36 alone has been discovered to be responsible for the increased insulin sensitivity observed in Ad-36 infected animals, including increased adipogenesis. Ad-36 E4 orf 1 protein can be used to increase insulin sensitivity and ameliorate diabetes. Additionally, drugs that mimic the action of Ad-36 E4 orf 1 protein could be found. Ad-36 E4 orf 1 could also be used to increase fat cells in lipodystrophy. We have also discovered that Ad-36 infection in human skeletal muscle cells increased differentiation and insulin independent glucose uptake. It is expected that infection with Ad-36 E4 orf 1 gene will also cause these effects.

9 Claims, 26 Drawing Sheets

OTHER PUBLICATIONS

Frese, K.K. et al., "Oncogenic function for the Dlg1 mammalian homolog of the *Drosophila* discs—large tumor suppressor," Embo J, vol. 25, pp. 1406-1417 (2006).

Frese, K. K., "Selective PDZ protein-dependent stimulation of phosphatidylinositol 3-kinase by the adenovirus E4-ORF1 oncoprotein," Oncogene, vol. 22, pp. 710-721 (2003).

Furnsinn, C. et al., "Thiazolidinediones: metabolic actions in vitro," Diabetologia, vol. 45, pp. 1211-1223 (2002).

Gosztonyi, G. et al., "Borna disease: Neuropathology and pathogenesis," Current Topics in Microbiology and Immunology, vol. 190, pp. 39-73 (1995).

Gregoire F.M. et al., "Understanding adipocyte differentiation," Physiological Reviews, vol. 78, No. 3, pp. 783-809 (1998).

Hansen, J.B., et al., "Peroxisome proliferator-activated receptor delta (PPARdelta)-mediated regulation of preadipocyte proliferation and gene expression is dependent on cAMP signaling,". J Biol Chem., vol. 276, No. 5, pp. 3175-3182 (2001).

Henry, R.R., et al., "Insulin action and glucose metabolism in nondiabetic control and NIDDM subjects. Comparison using human skeletal muscle cell cultures," Diabetes, vol. 44, pp. 936-946 (1995).

Hierholzer, J.C., et al., "Adenoviruses from patients with AIDS: A plethora of serotypes and a description of five new serotypes of subgenus D (Types 43-47)," J Infectious Dis, vol. 158, No. 4, pp. 804-813 (1988).

Horvath, J. et al., "Group C adenovirus sequences in human lymphoid cells," J Virol, vol. 59, No. 1, pp. 189-192 (1986).

Javier, R. et al., "Human adenovirus type 9-induced rat mammary tumors," J Virol, vol. 65, No. 6, pp. 3192-3202 (1991).

Javier, R. et al., "Requirement for the adenovirus type 9 E4 region in production of mammary tumors," Science, vol. 257, pp. 1267-1271 (1992).

Javier, R. T. "Adenovirus type 9 E4 open reading frame 1 encodes a transforming protein required for the production of mammary tumors in rats," J Virol, vol. 68, No. 6, pp. 3917-3924 (1994).

Kanda, H. et al., "MCP-1 contributes to macrophage infiltration into adipose tissue, insulin resistance, and hepatic steatosis in obesity," J Clin Invest., vol. 116, No. 6, pp. 1494-1505 (2006).

Klip, A..G., "Induction of sugar uptake response to insulin by serum depletion in fusing L 6 myoblase," Am. J. Physiol, vol. 247, pp. E291-E296 (1984).

Komers, R. et al., "Thiazolidinediones—tools for the research of metabolic syndrome X," Physiol Res., vol. 47, pp. 215-225 (1998).

Kou, B. et al., "Gene therapeutic exploration: retrovirus-mediated soluble vascular endothelial growth factor receptor-2 (sFLK-1) inhibits the tumorigenicity of S180, MCF-7, and B16 cells in vivo," Oncol Res., vol. 15, pp. 239-247 (2005).

Latorre, I. J. et al., "Viral oncoprotein-induced mislocalization of select PDZ proteins disrupts tight junctions and causes polarity defects in epithelial cells," J Cell Sci , vol. 118, Pt 18, pp. 4283-4293 (2005).

Loiler, S.A. et al., "Localized gene expression following administration of adeno-associated viral vectors via pancreatic ducts.," Mol Ther., vol. 12, No. 3, pp. 519-527 (2005).

Lyons, M.J. et al., "A virally induced obesity syndrome in mice," Science, vol. 216, pp. 82-85 (1982).

Magun, R. et al., "Expression of a constitutively activated form of protein kinase B (c-Akt) in 3T3-L1 preadipose cells causes spontaneous differentiation," Endocrinology, vol. 137, No. 8, pp. 3590-3593 (1996).

Neumann, R. et al., "Detection of adenovirus nucleic acid sequences in human tonsils in the absence of infectious virus," Virus Res, vol. 7, pp. 93-97 (1987).

Nourry, C. et al., "PDZ domain proteins: plug and play!" Sci STKE, vol. 179, RE7 (2003).

Ntambi, J.M. et al., "Adipocyte differentiation and gene expression," J Nutr., vol. 30, No. 12, pp. 3122S-3126S (2000).

Oka, Kazuhiro et al., "Liver-directed Gene Therapy for Dyslipidemia and Diabetes," Curr Atheroscler Rep., pp. 1-11 (2005).

Pasarica, M. et al., "Adipogenic Human Adenovirus Ad-36 Induces Commitment, Differentiation and Lipid Accumulation in Human Adipose-derived Stem Cells," Stem Cells, published at http://www.StemCells.com on Jan. 17, 2008.

Pasarica, M. et al., "Enhanced cell cycle activation by adenovirus 36 may contribute to increased lipid accumulation in 3T3-L1 cells," FASEB J, vol. 19, No. 4, pp. A70 (2005).

Pasarica, M. et al., "Human adenovirus-36 (Ad-36) induces adiposity in rats," Obesity Research, vol. 12 (Suppl), p. A122 (2004).

Pasarica, M. et al., "Human Adenovirus 36 Induces Adiposity, Increases Insulin Sensitivity, and Alters Hypothalamic Monoamines in Rats," Obesity, vol. 14, No. 11, pp. 1905-1913 (2006).

Pereira, H.G. et al., "A short description of the adenovirus group," Virology, vol. 20, pp. 613-620 (1963).

Powledge, T.M., "Is obesity an infectious disease?" Lancet Infect Dis., vol. 4, No. 10, p. 599 (2004).

Rajala, M.S. et al., "Corneal cell survival in adenovirus type 19 infection requires phosphoinositide 3-kinase/Akt activation," J Virol, vol. 79, No. 19, pp. 12332-12341 (2005).

Rathod, M. et al., "Viral mRNA Expression but not DNA Replication is Required for Lipgenic Effect of Human Adenovirus Ad-36 in Preadipocytes," Int'l J. Obesity, vol. 31, pp. 78-86 (2007).

Reusch, J.E. et al., "CREB activation induces adipogenesis in 3T3-L1 cells,"Mol Cell Biol, vol. 20, No. 3, pp. 1008-1020 (2000).

Rogers, P.M. et al., "Human Adenovirus Ad-36 Induces Adipogenesis Via Its E4 orf-1 Gene," Int'l J. Obesity, pp. 1-10 (2007).

Rossner, S., Can obesity be an infectious disease?, Lakartidningen, vol. 102, Nos. 24-25, pp. 13-26 (2005), No English translation.

Sakaue, H. et al., "Posttranscriptional control of adipocyte differentiation through activation of phosphoinositide 3-kinase," J Biol Chem, vol. 273, No. 44, pp. 28945-28952 (1998).

Shen, Y. et al., "Viruses and apoptosis," Curr Opin Genet Dev., vol. 5, pp. 105-111 (1995).

So, P.W. et al., "Adiposity induced by adenovirus 5 inoculation," Int J Obes, vol. 29, pp. 603-606 (2005).

Stern, J.S. et al., "Adipose-cell size and immunoreactive insulin levels in obese and normal-weight adults," Lancet, vol. 2, No. 7784, pp. 948-951 (1972).

Suomalainen, M. et al., "Adenovirus-activated PKA and p38/MAPK pathways boost microtubule-mediated nuclear targeting of virus," Embo J, vol. 20, No. 6, pp. 1310-1319 (2001).

Tan, P.H. et al., "Effect of vectors on human endothelial cell signal transduction: implications for cardiovascular gene therapy," Arterioscler Thromb Vasc. Biol., vol. 26, pp. 462-467 (2006).

Thomas, D. L., et al., "Early region 1 transforming functions are dispensable for mammary tumorigenesis by human adenovirus type 9," J Virol, vol. 73, No. 4, pp. 3071-3079 (1999).

Tomiyama, K. et al., "Wortmannin, a specific phosphatidylinositol 3-kinase inhibitor, inhibits adipocytic differentiation of 3T3-L1 cells," Biochem Biophys Res Commun, vol. 212, No. 1, pp. 263-269 (1995).

Vangipuram, S.D. et al., "A Human Adenovirus Enhances Preadipocyte Differentiation," Obesity Research, vol. 12, No. 5, pp. 770-777 (2004).

Vangipuram, S.D. et al., "Adipogenic Human Adenovirus-36 Reduces Leptin Expression and Secretion and Increases Glucose Uptake by Fat Cells," Intn'l J. Obesity, vol. 31, pp. 87-96 (2007).

Verges, B., "Clinical interest of PPARs ligands," Diabetes Metab., vol. 30, pp. 7-12 (2004).

Virella-Lowell, I, "Enhancing rAAV vector expression in the lung," J Gene Med., vol. 7, pp. 842-850 (2005).

Wang, Z.Q. et al., "Chromium picolinate enhances skeletal muscle cellular insulin signaling in vivo obese, insulin-resistant JCR:LA-cp rats.," J. Nutr., vol. 136, pp. 415-420 (2006).

Wang, Z.Q. et al., "Effect of age and caloric restriction on insulin receptor binding and glucose transporter levels in aging rats," Exp Gerontology, vol. 32, No. 6, pp. 671-684 (1997).

Wang, Z.Q. et al., "Human adenovirus type 36 enhances glucose uptake in diabetic and non-diabetic human skeletal muscle cells independent of insulin signaling," Accepted for publication by Am. Diabetes Assoc (2008), published online Apr. 16, 2008.

Weiss, R. S. et al., "Human adenovirus type 9 E4 open reading frame 1 encodes a cytoplasmic transforming protein capable of increasing the oncogenicity of CREF cells," J Virol., vol. 70, No. 2, pp. 862-872 (1996).

Weiss, R. S. et al., "Mutant adenovirus type 9 E4 ORF 1 genes define three protein regions required for transformation of CREF cells," J Virol., vol. 71, No. 6, pp. 4385-4394 (1997).

Weyer, C. et al., "Enlarged subcutaneous abdominal adipocyte size, but not obesity itself, predicts type II diabetes independent of insulin resistance," Diabetologia, vol. 43, pp. 1498-1506 (2000).

Wigand, R. et al., "New human adenovirus (candidate adenovirus), a novel member of subgroup D," Arch Virology, vol. 64, pp. 225-233 (1980).

Yamada, T. et al., "Novel Tissue and Cell Type-specific Gene / Drug Delivery System Using Surface Engineered Hepatitis B Virus Nanoparticles," Current Drug Targets—Infectious Disorders, vol. 4, pp. 163-167 (2004).

Javier, Ronald et al., "Mammary Tumors Induced by Human Adenovirus Type 9: A Role for the Viral Early Region 4 Gene," Breast Cancer Res. and Treatment, vol. 39, No. 1, pp. 57-67 (1996).

Mahida, Miloni. et al., "Down-regulating the Expression of Adenovirus-36 Gene E4 orf 1 Attenuates the Pro-Differentiation Effect of the Virus on Fat," FASEB Journal, vol. 19, No. 4, Supp. S, Part 1, p. A70 (entry 67.6) (2005); AND Experimental Biology 2005 Meeting / 35$^{th}$ Int'l Congress of Physiological Sciences; San diego, CA Mar. 31 (Apr. 6, 2005), Abstract.

Oka, Kazuhiro et al., "Liver-directed Gene Therapy for Dyslipidemia and Diabetes," Cur. Atheroscler. Rep., vol. 6, No. 3, pp. 203-209 (2004).

Fusinski, Keith et al., "Adenovirus-36 Transcription Factor E4orf1 Accelerates Preadipocyte Differentiation," Obesity Res., vol. 12, Supp. Program Abstr., NAASO's 2004 Annual Meeting (2004).

Vangipuram, Sharada et al., "Expression of the Early Genes of Human Adenovirus 36 During 3T3-L1 Cell Differentiation," Am. Soc. for Virology, 23$^{rd}$ Meeting, Montreal Quebec, CA (2004).

Vangipuram, Sharada et al., "Up-Regulation of Preadipocyte Differentiation by Human Adenovirus Ad-36 Correlates with Expression of the Viral E1A and E4-Orf1 Genes," Obesity Res., vol. 11, Supp. Program Abstr., NAASO's 2003 Annual Meeting, Ft. Lauderdale, FL (2003).

Berg, A.H. et al., "The Adipocyte-secreted Protein Acrp30 Enhances Hepatic Insulin Action," Nature Med., vol. 7, No. 8, pp. 947-953 (2001).

Bouskila, M. et al., "Adiponectin: a Relevant Player in PPARγ-agonist-mediated Improvements in Hepatic Insulin Sensitivity?" Int'l J. of Obesity, vol. 29, pp. S17-S23 (2005).

Cho, H. et al., "Insulin Resistance and a Diabetes Mellitus-like Syndrome in Mice Lacking the Protein Kinase Akt2 (PKBβ)," Science, vol. 292, pp. 1728-1731 (2001).

Combs, T.P. et al., "Endogenous Glucose Production in Inhibited by the Adipose-Derived Protein Acrp30," The J. of Clin. Inves., vol. 108, No. 12, pp. 1875-1881 (2001).

Combs, T.P. et al., "Induction of Adipocyte Complement-Related Protein of 30 Kilodaltons by PPARγ Agonists: A Potential Mechanism of Insulin Sensitization," Endocrinology, vol. 143, No. 3, pp. 998-1007 (2002).

Jiang, G. et al., "PI 3-Kinase and its Up- and Down-Stream Modulators as Potential Targets for the Treatment of Type II Diabetes," Frontiers in Bioscience, vol. 7, pp. d903-d917 (2002).

Jiang, Z.Y. et al., "Insulin Signaling Through Akt/protein Kinase B Analyzed by Small Interfering RNA-mediated Gene Silencing," PNAS, vol. 100, No. 13, pp. 7569-7574 (2003).

Krook, Anna et al., "Insulin-Stimulated Akt Kinase Activity is Reduced in Skeletal Muscle from NIDDM Subjects," Diabetes, vol. 47, pp. 1281-1286 (1998).

Kubota, N. et al., "Disruption of Adiponectin Causes Insulin Resistance and Neointimal Formation," The J. of Biol. Chem., vol. 277, No. 29, pp. 25863-25866 (2002).

Mizukami, J. et al., "The Antidiabetic Agent Thiazolidinedione Stimulates the Interaction between PPARγ and CBP," Biochem. and Biophys. Res. Comm., vol. 240, pp. 61-64 (1997).

Moller, D.E. et al., "Role of PPARs in the Regulation of Obesity-Related Insulin Sensitivity and Inflammation," Int3 1 J. of Obesity, vol. 27, pp. 517-521 (2003).

Picard, F. et al., "PPARγ and Glucose Homeostasis," Annu. Rev. Nutr., vol. 22, pp. 167-197 (2002).

Stefan, N. et al., "Plasma Adiponectin Concentration is Associated with Skeletal Muscle Insulin Receptor Tyrosine Phosphorylation, and Low Plasma Concentration Precedes a Decrease in Whole-Body Insulin Sensitivity in Humans," Diabetes, vol. 50, pp. 1884-1888 (2002).

Takahashi, N. et al., "Overexpression and Ribozyme-mediated Targeting of Transcriptional Coactivators CREB-binding Protein and p300 Revealed Their Indispensable Roles in Adipocyte Differentiation through the Regulation of Peroxisome Proliferator-activated Receptor γ," The J. of Bio. Chem., vol. 277, No. 19, pp. 16906-16912 (2002).

Vazquez, M. et al., "Experimental Approaches to Study PPARγ Agonists as Antidiabetic Drugs," Meth.Find Exp. Clin. Pharmacol., vol. 24, No. 8, pp. 515-523 (2002).

Weyer, C. et al., "Hypoadiponectinemia in Obesity and Type 2 Diabetes: Close Association with Insulin Resistance and Hyperinsulinemia," The J. of Clin. Endocrin. and Metab., vol. 86, No. 5, pp. 1930-1935 (2001).

Yamauchi, T. et al., "The fat-derived hormone adiponectin reverses insulin resistance associated with both lipoatrophy and obesity," Nature Med., vol. 7, No. 8, pp. 941-946 (2001).

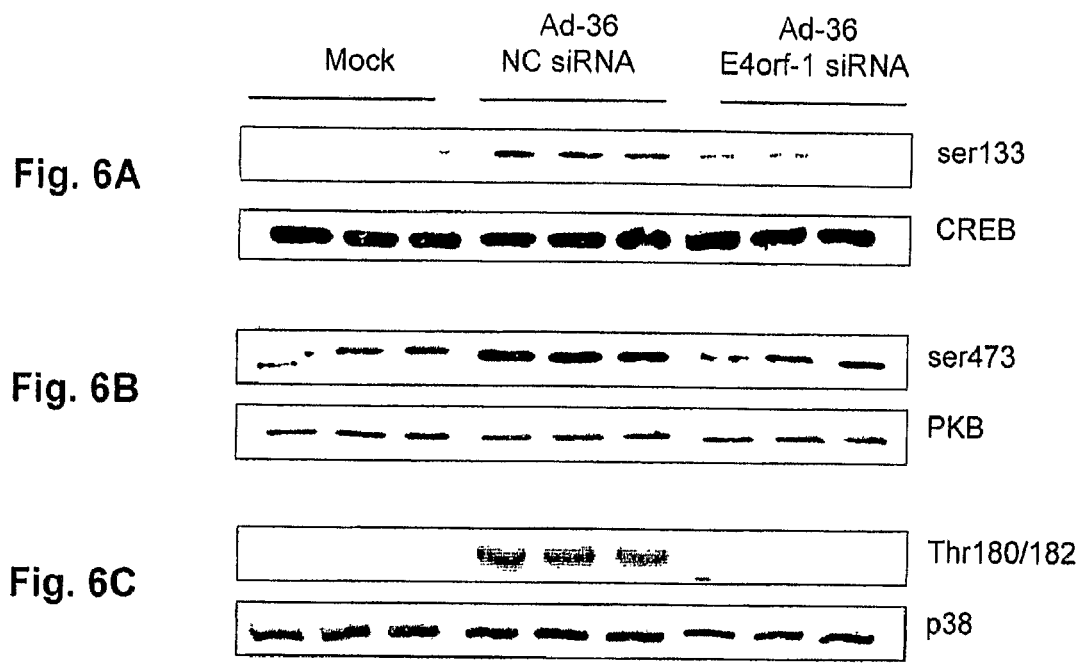

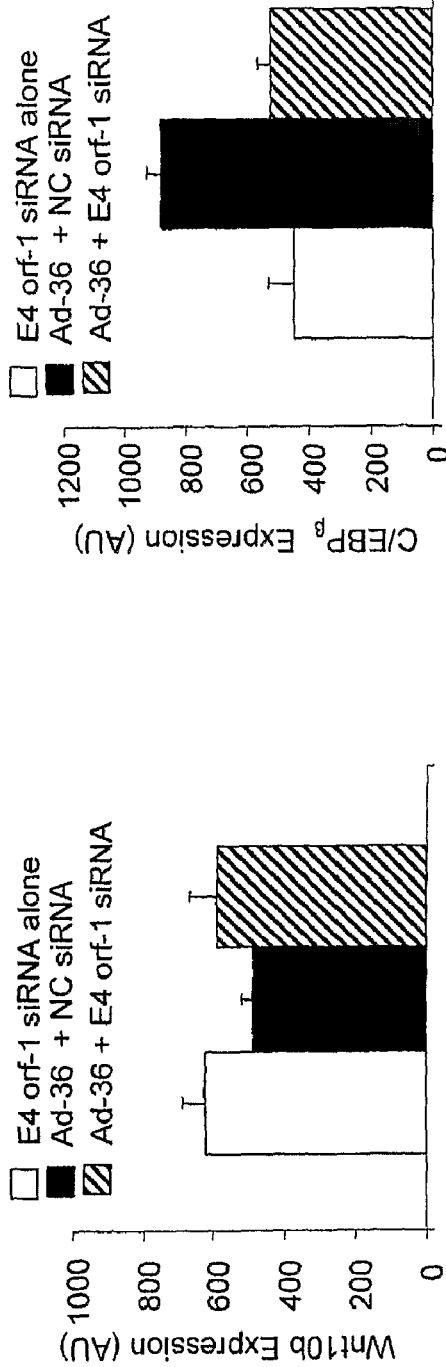
Fig. 7A
Fig. 7B
Fig. 7C
Fig. 7D

ADENOVIRUS 36 E4 ORF 1 GENE AND PROTEIN AND THEIR USES

This is the United States national stage of international application PCT/US06/045919, filed 30 Nov. 2006, which claims the benefit of the 30 Nov. 2005 filing date of U.S. provisional application Ser. No. 60/741,399 under 35 U.S.C. §119(e).

The development of this invention was partially funded by the Government under a grant from the National Institutes of Health, grant no. R-01 DK066164. The Government has certain rights in this invention.

TECHNICAL FIELD

This invention pertains to a composition and a method to increase insulin sensitivity and ameliorate symptoms of diabetes or aid in lipodystrophy using Adenovirus type-36 E4 orf 1 protein or the gene that encodes this protein.

BACKGROUND ART

Infectoobesity

As the epidemic of obesity continues unabated, infectoobesity, obesity of infectious origin, has been receiving increasing attention in the recent years (1-3). Although many factors contribute to the etiology of obesity, a subset of obesity may be caused by infections. In the last two decades, 10 obesity-promoting pathogens have been reported (4). The first human virus, adenovirus type 36 (Ad-36), was reported that caused obesity in experimentally infected animals (5-7) and showed association with human obesity (8).

Although obesity is recognized as a disease of multiple etiologies, microbial infection as an etiological factor has received attention only recently. Seven viruses and a scrapie agent have been reported to cause obesity in animal models (5-7, 10-20). Which of these pathogens can cause obesity in humans remains to be determined. The avian adenovirus SMAM-1 and human adenovirus type 36 (Ad-36) has been reported to cause adiposity in animal models (5-7, 15,16) and to show association with human obesity (8,17). In-vitro experiments have shown that Ad-36 infection of rat preadipocytes (3T3-L1) and human preadipocytes promote their proliferation and differentiation (9). Recently, obesity promoting effects of Ad-5, another human adenovirus, were reported (20). So far, adenoviruses are the only types of viruses linked with human obesity. Therefore, among the adipogenic pathogens, they are the prime targets for determining a role in human obesity.

Adenoviruses

Adenoviruses. In humans, adenoviruses infections are common (21) and cause acute upper respiratory tract infections, enteritis or conjunctivitis. Presence of antibodies to adenovirus is common in the general population (22). Adenoviral DNA is detected in asymptomatic adult human lymphocytes, and the number of positive cells increases with the age of the person (23, 24). There are six major subgroups (A-F) among the 50 human adenoviruses. Each subgroup has a number of specific serotypes. Adenovirus type-36 (Ad-36) belongs to subgroup D, serotype 36. Ad-36 is serologically different when compared to 48 types of human adenoviruses with the exception of a weak cross-reaction with Ad-29 (25, 26). Adenoviruses are non-enveloped DNA viruses (27) that replicate in host cell nucleus. In all serotypes the genes encoding specific functions are located at the same position on the viral chromosome (28). The genome consists of a single linear, double stranded DNA molecule which consists of five early transcription units (E1A, E1B, E2, E3 and E4), two delayed early units (IX and IVa2), and one major late unit which generates five families of mRNAs (L1 to L5). Adenovirus serotypes show genetic diversity, which is promoted by commonly occurring recombination events among adenoviruses.

Replicative cycle: Most studies on replication have been done using Ad-2 or Ad-5, since they are easily grown in the laboratory either by infecting HeLa or KB cells. Conventionally, the replicative cycle is divided into 2 phases. Early events include adsorption, penetration, transcription and translation of an early set of genes. Early viral gene products mediate viral gene expression, DNA replication, induce cell cycle progression, and block apoptosis. Once viral DNA replication is initiated, the 'Late' phase begins with the expression of late genes and assembly of progeny virions.

Adsorption and Entry: Attachment of adenoviruses to cells is mediated by the fiber protein. The distal carboxy-terminal domain of the fiber protein terminates in a knob that is thought to bind to the cell receptor (28). The Coxsackievirus-Adenovirus Receptor (CAR receptor) protein was shown to function as a cellular attachment protein for adenovirus serotypes from Subgroups A, C, D, E, and F. Subsequently, in a process that has been shown to be independent of fiber-CAR interaction, the viral penton base protein binds to cellular $\alpha_v$-integrins through, a tripeptide motif of the penton base, followed by internalization of the virus particle. However, group D viruses may be able to enter via a CAR-independent pathway, possibly by direct interaction of penton base and $\alpha_v$-integrins.

Activation of early viral genes: There are three major functions for the adenoviral early gene expression: (1) to induce host cell to enter 'S' phase of the cell cycle to provide optimal conditions for viral replication; (2) to set up viral systems that protect the infected cell from the anti-viral defenses of the host organism; and (3) to synthesize viral gene products for viral DNA replication (28). The following is a brief description of the role of various adenoviral proteins.

E1A proteins: Once the viral chromosome reaches the nucleus, E1A is the first transcription unit to be expressed. E1A transcription is controlled by a constitutive promoter which also contains a duplicated enhancer element. The E1A unit encodes two mRNAs during the early phase of infection and subsequently 3 other species whose function is not clear. The two early mRNAs encode the 12S and 13S E1A proteins named for the sedimentation co-efficient of their mRNAs. The E1A proteins are referred to as trans-activators since they can activate other viral genes in trans. 13S E1A protein binds directly to the TATA binding protein and activates transcription. E1A can activate transcription by binding directly to several cellular factors such as pRB, p300, ATF-2, and TBP. Adenoviral early genes remain active through the viral replication cycle although the rate of transcription declines. E1A can induce terminally differentiated skeletal muscle cells to synthesize DNA and divide. This is also true for myocytes, adipocytes and myocardiocytes.

E1B proteins: The adenoviral E1B transcription unit encodes two different proteins, E1B 55-57 kDa and E1B 19-21 kDa, which block p53 induced growth inhibition and apoptosis (28). E1B proteins antagonize growth arrest and apoptosis and co-operate with E1A to oncogenically transform cultured cells. Their role in oncogenic transformation shows the ability of these proteins to interfere with normal cellular regulators.

E2 Proteins. The E2 region is subdivided into E2A and E2B and encodes 3 proteins. These proteins provide the machinery for viral DNA replication. Terminal protein (TP) acts as a primer for initiation of DNA synthesis. The DBP (adenoviral DNA binding protein) gene encodes DNA binding protein and the pol gene encodes the DNA dependant DNA polymerase E3 Proteins: The Adenovirus E3 transcription unit encodes seven proteins, none of which is required for replication of the virus in culture. Proteins from E3 transcription unit protect cells from death mediated by cytotoxic T cells and death-inducing cytokines such as tumor necrosis factor (TNF), FAS ligand, and TNF-related apoptosis-inducing ligand. Studies on subgenus C adenoviruses demonstrated that most E3 proteins exhibit immunomodulatory functions. E3/19K glycoprotein prevents expression of newly synthesized MHC molecules by inhibition of ER export, whereas the E3/10.4-14.5K protein down-regulates apoptosis receptors by rerouting them into lysosomes. E3/49K, another recently discovered E3 protein, has been suggested to have immunomodulatory activity. E3 membrane proteins exploit the intracellular trafficking machinery for immune evasion. Adenoviruses may harbor more undiscovered E3 proteins that exploit intracellular trafficking pathways as a means to manipulate immunologically important key molecules.

E4 Proteins: The E4 region includes seven open reading frames (ORFs). Some of these encode proteins that contribute to the cell cycle regulation. Products of various E4 ORFs are shown to be involved in host cell transformation.

Intermediate Protein IVa2 and IX: Adenoviral IVa2 protein is involved in adenovirus assembly. Protein IX is a multifunctional protein which stabilizes the capsid and has transcriptional activity.

Late Transcription: Late phase transcription is driven primarily by the major late promoter. Transcription from this promoter involves multiple polyadenylation and elaborate RNA splicing. Five gene clusters (L1-L5) can be identified from this region. These genes primarily code for virion structural proteins. Upon complete assembly of the virus, the host cell wall is ruptured and virions are released for subsequent infections. Complete assembly of the virus occurs in permissive cells.

Adenovirus Type 36 (Ad-36)

In 1978, Ad-36 was first isolated in Germany, from the feces of a 6-year-old girl suffering from diabetes and enteritis (26). Ad-36 belongs to subgroup D and is distinct both in neutralization and hemagglutination-inhibition from all other human adenoviruses (26). Ad-36 is the first human adenovirus to be associated with human obesity (8).

Human adenovirus type 36 increases body fat in experimentally infected animals and shows association with human obesity (5-8). Ad-36 stimulates preadipocytes (pre-fat cells) to differentiate into adipocytes (fat cells), and increases the number of fat cells and their lipid content (9). Ad-36 can induce differentiation of preadipocytes even in absence of conventional differentiation inducers such as the cocktail of methyl isobutyl xanthine, dexamethasone, and insulin (MDI). A similar effect of the virus is observed in human adipose derived stem cells (9). Rats infected with Ad-36 showed greater adiposity but paradoxically lower insulin resistance 7 months post-infection (50). Moreover, fat cells from uninfected rats when infected with Ad-36 show increased glucose uptake, indicating greater insulin sensitivity (51).

Increased insulin sensitivity despite gain in body fat is also seen in antidiabetic medications of the Thiazolidinediones (TZD) class (52,53). The TZDs increase preadipocyte replication, differentiation and lipid accumulation and increase whole body insulin sensitivity. It is believed that the insulin sensitizing effect of the TZDs is due to their effect on preadipocyte replication and differenctiation (which generates new smaller adipocytes) and on PPARγ (an important gene in adipocyte differentiation and insulin signaling pathway) (52, 53). Insulin sensitivity in humans is shown to inversely correlate with adipocyte size (54,55).

Factors required for increased insulin sensitivity include greater preadipocyte number and differentiation, and activation of cAMP and insulin signaling pathway enzymes (e.g., phosphotidyl inositol-3 kinase (PI3K or PI3 kinase)). Preadiopcyte differentiation in turn is modulated by activation of PI3 kinase and cAMP signaling pathways (43-48). Ad-36 has been shown to increase preadipocyte replication, the number of differentiated adipocytes, and PI3 kinase pathway (56).

Adipogenic potential of Ad-36 is not shared by all adenoviruses. Avian adenovirus CELO (Chick Embryo Lethal Orphan virus) or human adenoviruses type 2 or 31 did not promote adiposity in animals (21,57). Unlike Ad-36, Ad-2 does not increase differentiation of preadipocytes (9). Seropositivity for Ad-36 was associated with human obesity (8). An almost equal distribution of seropositivity was observed among the obese and non-obese subjects for the non-adipogenic adenoviruses Ad-2 and Ad-31 (8, 49). This suggests that the greater prevalence of Ad-36 antibodies in obese subjects (8) is not merely a result of obesity, and that Ad-2 or Ad-31 are not associated with obesity.

E4 orf 1 and Differentiation

Although group D (of Ad-36) contains the largest number of serotypes, it is not as well studied as the group C adenoviruses (e.g., Ad-2 and Ad-5). However, one group D virus, Ad-9, has been partially characterized. This virus first attracted attention because it caused tumors in rats (29). Investigation of the tumorigenic mechanism of Ad-9 showed that the E4 orf 1 gene was required. The E1A and E1B genes, which are necessary and sufficient for transformation by group A and group B adenoviruses, are not required for Ad-9 transformation (30-33). Subsequent studies on the Ad-9 E4 orf 1 protein identified 3 domains in which mutations caused a loss of transforming activity (34). One of these is located at the C-terminus of the protein and was subsequently shown to be a PDZ-binding domain. PDZ domains were first recognized as protein interaction domains in PSD/SAP90, Dlg, and ZO-1. These domains are roughly 90 amino acids in size and are found in over 400 human proteins (35). PDZ domains mediate protein interaction by binding to PDZ-binding domains typically located at the C-termini of other proteins, as is the case for Ad-9 E4 orf 1. They may also bind to internal peptides and other PDZ domains. PDZ proteins may have as few as one or over a dozen PDZ domains and frequently contain other types of protein interaction domains as well. PDZ proteins have been described as scaffolding proteins that organize other proteins into functional groups, and have been shown to have roles in signal transduction, neuronal synapses, and intercellular junctions. The Ad-9 E4 orf 1 protein has been shown to associate with the PDZ proteins MUPP1, MAGI-1, ZO-2, and PATJ to relocate these proteins from the epithelial cell tight junctions to the cytoplasm. Deletion of the Ad-9 E4 orf 1 PDZ-binding domain abolishes these protein interactions and destroys E4 orf 1 transformation activity (36). Ad-9 E4 orf 1 also activates PI3K (37). This requires the E4 orf 1 PDZ-binding domain and so presumably involves a PDZ protein(s), which is not yet identified. Neither the catalytic nor the regulatory subunits of PI3K contain PDZ domains. Although activation of PI3K is required for E4 orf 1-induced transformation, it is not sufficient. Upregulation of PI3K pathway is a common cellular response to several of the 50 known types of human adenoviruses (71-74). PI3K is an enzyme which is required for adipogenesis (38, 39). But Ad-2, a non-adipogenic virus, also upregulates PI3K activity (71). Therefore, the adipogenetic response to infection with Ad-36 involves more that just upregulation of PI3K activity.

Ad-36 Induced Adiposity

The process of adipocyte differentiation comprises growth arrest, followed by a clonal expansion phase, and ending with the expression of key transcription factors and terminal differentiation. The differentiation process in rat preadipocytes (3T3-L1 cells) can be initiated by exposure of the confluent cells to methyl-isobutylxanthine, dexamethasone, and insulin (MDI). During differentiation, the genes that are inhibitory to adipogenesis or unnecessary to fat cell function are repressed (e.g. Pref-1, CUP, and PRE decrease). However, expression of early, intermediate, and later genes of differentiation (e.g., C/EBPβ C/EBPδ and RXR) increases, followed by expression of C/EBPα and PPARγ, and finally followed by lipid accumulation. CEBP/β expression is critical for activation of PPAR and other downstream pro-adipogenic genes (40). Co-expression of C/EBPβ and C/EBPδ induce PPARγ expression, which is the most adipose-specific of the PPARs (α, δ and γ) (41). PPARγ expression together with CEBPα leads to activation of several genes including aP2, GLUT4, SCD1, PEPCK and leptin (41, 42) and to completion of the differentiation process.

DISCLOSURE OF INVENTION

We have discovered that expression of the E4 orf 1 gene of Ad-36 alone is responsible for the increased insulin sensitivity observed in Ad-36 infected animals. To determine the effects of Ad-36 E4 orf 1, 3T3-L1 preadipocytes were prepared that stably express the Ad-36 E4 orf 1 gene, E4 orf 1 without its PDZ binding domain (E4 orf 1 ΔPDZ), or an empty vector (control). We observed that 3T3-L1 cells expressing Ad-36 E4 orf 1, or E4 orf 1 ΔPDZ had significantly greater activation of cAMP pathway compared to the control, whereas, only the Ad-36 E4 orf 1 expressing cells had greater activation of PI3 kinase pathway. Attenuation of the effect of E4 orf 1 on PI3 kinase pathway by deletion of PDZ binding region of the protein (E4 orf 1 ΔPDZ) suggested that the PDZ binding domain of the Ad-36 E4 orf 1 protein contributes to PI3 kinase activation. Furthermore, Ad-36 E4 orf 1 expressing 3T3-L1 preadipocytes showed an extremely high ability to differentiate. Additionally, E4 orf 1 expression increased preadipocyte replication. Thus we have discovered that the Ad-36 E4 orf 1 protein increases insulin sensitivity and promotes preadipocyte differentiation. This protein can be used to increase insulin sensitivity and ameliorate diabetes. Additionally, drugs that mimic the action of the Ad-36 E4 orf 1 protein could be used to increase insulin sensitivity and ameliorate diabetes. The Ad-36 E4 orf 1 protein could also be used to increase replication of cells, such as stem cells, and used to increase fat cells in a patient with lipodystrophy—when the subject lacks the ability to develop mature fat cells. This condition can result in severe co-morbidity as a result of an inability to store body fat in the adipocytes.

In addition, we have discovered the insulin sensitizing potential of Ad-36 infection is likely to be dependent on increased preadipocyte proliferation and adipogenesis, activation of PPARγ2, LPL, FAS and glycerol kinase gene expression, and increased secretion of adiponectin. None of these changes have been reported for other human adenoviruses. An increase in PI3K has been reported for other human adenoviruses, as well as for Ad-36. Only Ad-36 is known to be associated with human obesity.

We have also discovered that Ad-36 infection in human skeletal muscle cells increased differentiation and insulin independent glucose uptake. Similar to adipocytes, it is expected that the Ad-36 E4 orf 1 protein causes these effects.

BRIEF DESCRIPTION OF THE DRAWINGS

FIGS. 6A-6C illustrate a Western blot analysis for CREB (FIG. 6A), PKB (FIG. 6B), and p38 (FIG. 6C) proteins from hASC 24 h after infection with media (mock) or with Ad-36+NC siRNA (MOI 3.8) or with Ad-36+E4 orf-1 siRNA (MOI 3.8).

FIG. 7A illustrates the degree of Wnt10b expression in hASC 1 day after infection with Ad-36+NC siRNA (MOI 3.8), E4 orf-1 siRNA alone (MOI 3.8), or Ad-36+E4 orf 1 siRNA (MOI 3.8).

FIG. 7B illustrates the degree of C/EBPβ expression in hASC 2 days after infection with Ad-36+NC siRNA (MOI 3.8), E4 orf-1 siRNA alone (MOI 3.8), or Ad-36+E4 orf 1 siRNA (MOI 3.8).

FIG. 7C illustrates the degree of PPARγ2 expression in hASC 3 days after infection with Ad-36+NC siRNA (MOI 3.8), E4 orf-1 siRNA alone (MOI 3.8), or Ad-36+E4 orf 1 siRNA (MOI 3.8).

FIG. 7D illustrates the degree of lipid accumulation in hASC 6 days after infection with Ad-36+NC siRNA (MOI 3.8), E4 orf 1 siRNA alone (MOI 3.8), or Ad-36+E4 orf 1 siRNA (MOI 3.8).

Figure 22A:
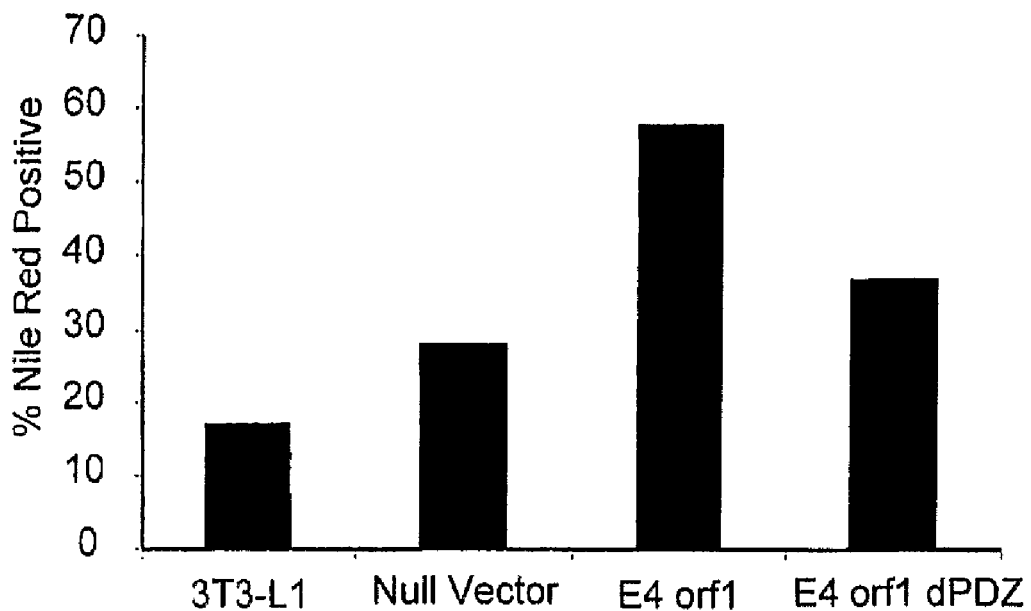
FIG. 22A illustrates the degree of lipid accumulation as measured using Nile Red stain in confluent 3T3-L1 cells inoculated with null vector, Ad-36 E4 orf 1 gene, or Ad-36 E4 orf 1 gene without the PDZ-binding domain (E4 orf 1 dPDZ) and incubated in MDI (MDI+, media with insulin and dexamethasone).
Figure 22B:
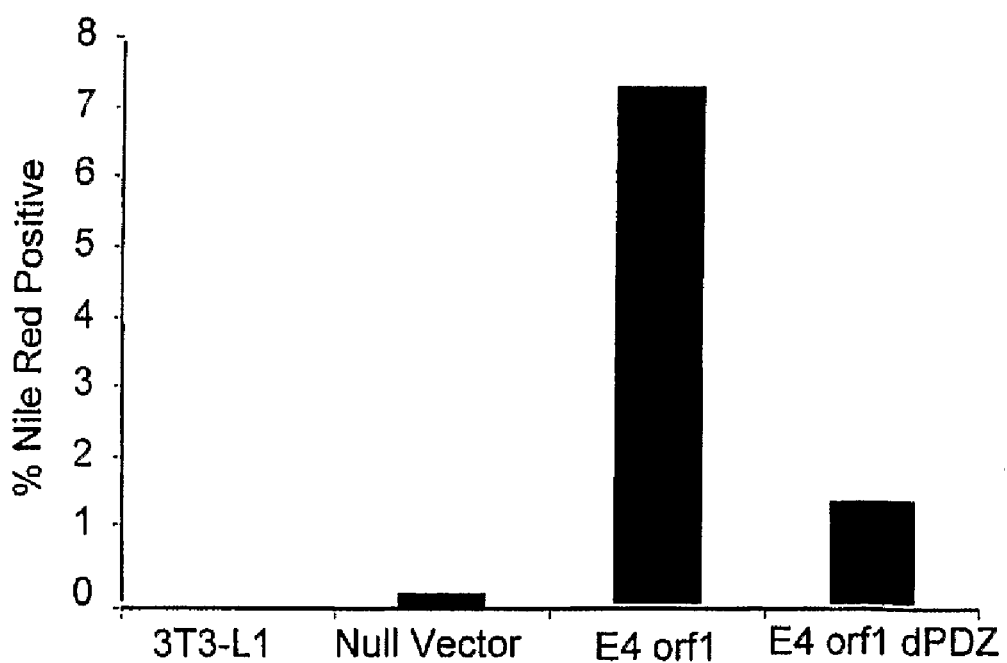
FIG. 22B illustrates the degree of lipid accumulation as measured using Nile Red stain in confluent 3T3-L1 cells inoculated with null vector, Ad-36 E4 orf 1 gene, or Ad-36 E4 orf 1 gene without the PDZ-binding domain (E4 orf 1 dPDZ) and incubated in only media (MDI–).
Figure 22C:
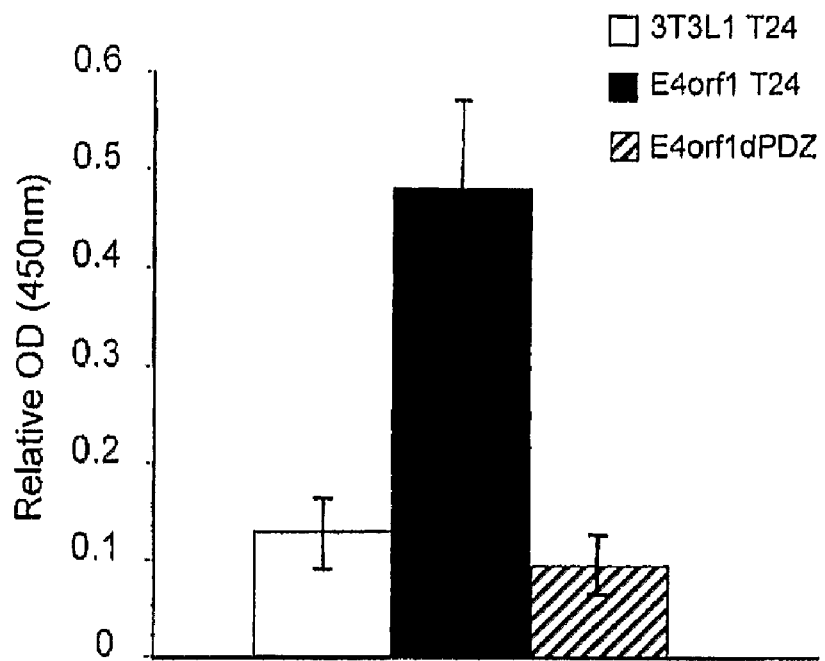

FIG. 22C illustrates the cAMP levels using a cAMP direct immunoassay kit from 3T3-L1 cells 24 h after re-feeding in wild 3T3-L1 cells, or cells inoculated with either the Ad-36 E4 orf 1 gene (E4orf1 T24) or the Ad-36 E4 orf 1 gene without the PDZ-binding domain (E4orf1 dPDZ).

Figure 22D:
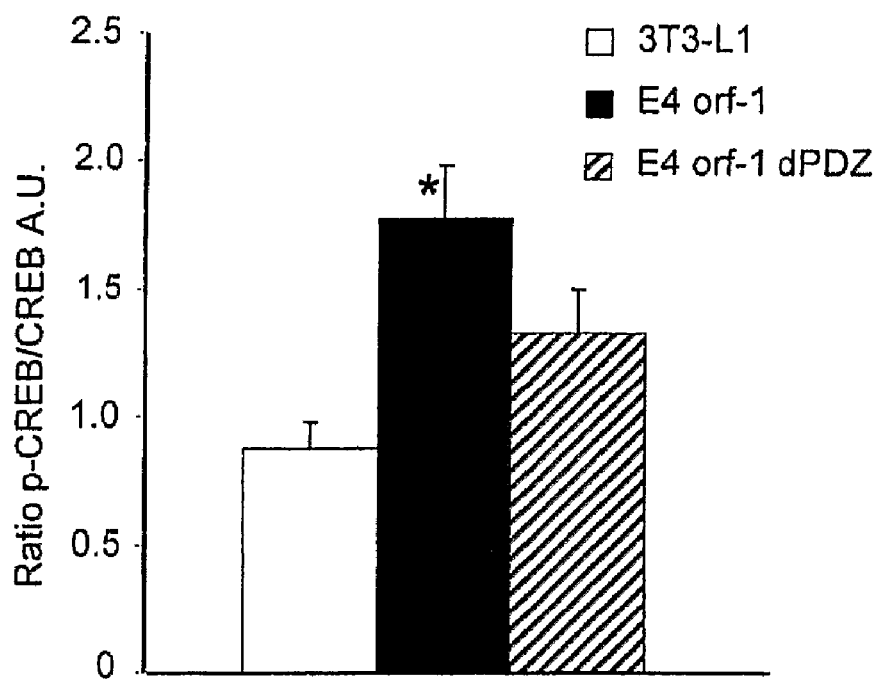

FIG. 22D illustrates the CREBP levels, as the ratio of phosphorylated CREB to total CREB, measured using Western Blot analysis on lysates from 3T3-L1 cells 24 h after re-feeding in wild 3T3-L1 cells, or cells inoculated with either the Ad-36 E4 orf 1 gene (E4orf1 T24) or the Ad-36 E4 orf 1 gene without the PDZ-binding domain (E4orf1 dPDZ).

Figure 22E:
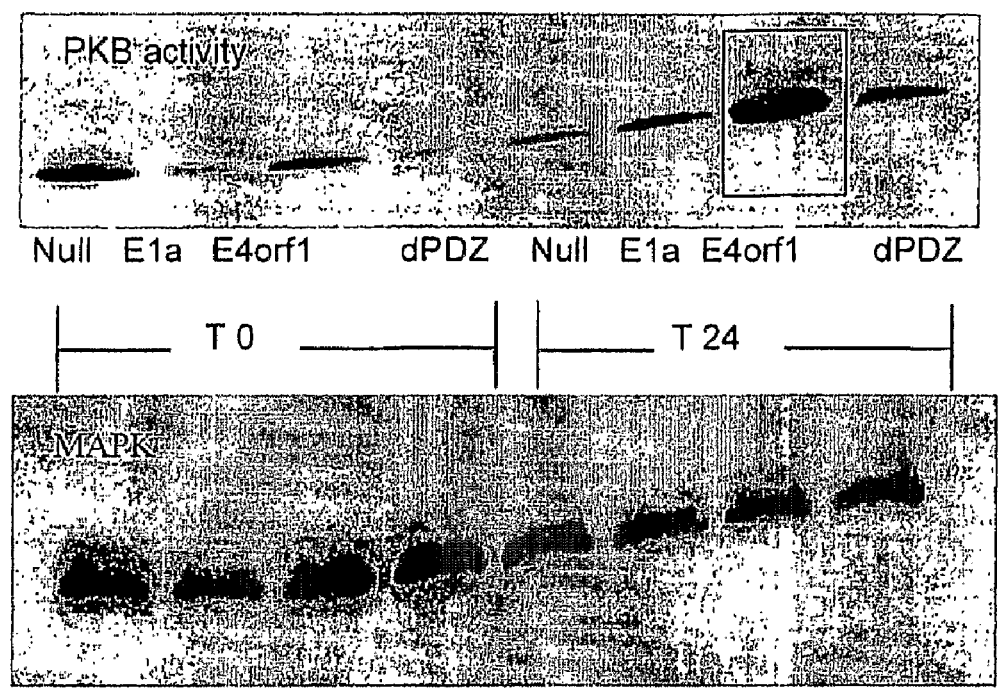

FIG. 22E illustrates the amount of phosphate kinase B (PKB) activity using a Western Blot analysis on lysates from 3T3-L1 cells at time 0 and 24 h after inoculation with either null vector (Null), the Ad-36 Ela gene (Ela), the Ad-36 E4 orf 1 gene (E4orf1) or the Ad-36 E4 orf 1 gene without the PDZ-binding domain (dPDZ), using MAPK expression as a control.

Figure 22F:
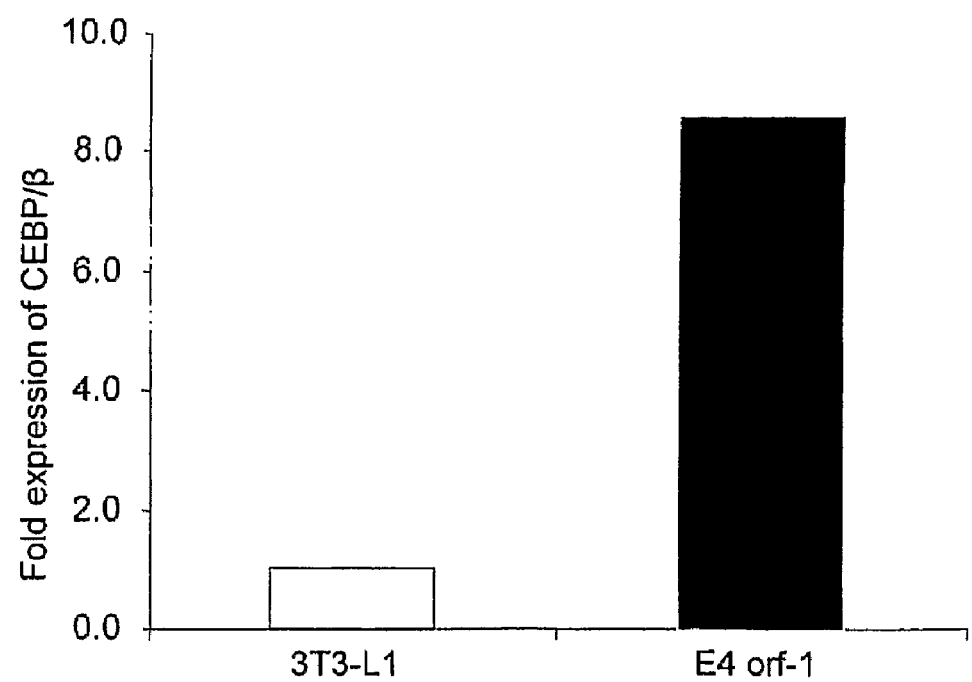

FIG. 22F illustrates the gene expression of CEBP/β measured using qRT-PCR on mRNA from 3T3-L1 cells either wild type (3T3L1) or 2 days after inoculation with E4 orf 1 gene (E4orf1).

MODES FOR CARRYING OUT THE INVENTION

We have isolated a nucleic acid sequence comprising SEQ ID NO: 1 that encodes Ad-36 E4 orf 1 protein. We also claim any nucleic acid sequence that encodes the same amino acid sequence as shown in SEQ ID NO: 2 in accordance with the degeneracy of the genetic code. A transformation vector comprising the nucleic acid sequence that encodes the Ad-36 E4 orf 1 protein could be used to transpose mammalian adipose cells or mammalian skeletal muscle cells.

We also disclose a method of treating or ameliorating the symptoms of a disease in a mammalian patient wherein the disease is chosen from the group comprising lipodystrophy, diabetes, or a disease due to insulin resistance, said method comprising administering to the patient a therapeutically effective amount of the Ad-36 E4 orf 1 protein, wherein the patient's symptoms improve following said administering. If the disease is related to insulin resistance, then the patient's insulin sensitivity will increases following said administering. If the disease is related to lipodystrophy, the number of adipose tissue cells in the patient increases following said administering. If the disease is diabetes due to a concentration of high serum glucose, then the amount of serum glucose decreases following said administering.

We also disclose that the Adenovirus-36 E4 orf 1 protein can be administered by introducing into the mammal a nucleic acid sequence encoding the Adenovirus-36 E4 orf 1 protein, in a manner permitting expression of the Adenovirus-36 E4 orf 1 protein. In such method, the nucleic acid sequence can be introduced by a method selected from the following group consisting of electroporation, DEAE Dextran transfection, calcium phosphate transfection, cationic liposome fusion, proptoplast fusion, creation of an in vivo electric field, DNA-coated microprojectile bombardment, injection with recombinant replication-defective viruses, homologous recombination, in vivo gene therapy, ex vivo gene therapy, viral vectors, and naked DNA transfer.

We also disclose a method for enhancing or inducing adipogenesis in a mammalian patient, comprising administering to the patient's adipose tissue a vector with the nucleic acid sequence to encode the Ad-36 E4 orf 1 protein; wherein expression of the encoded amino acid sequence in the patient's adipose tissue results in adipogenesis.

We also disclose a method for enhancing or inducing glucose uptake in a mammalian patient, comprising administering to the patient's skeletal muscle tissue a vector with the nucleic acid sequence to encode the Ad-36 E4 orf 1 protein; wherein expression of the encoded amino acid sequence in the patient's skeletal muscle tissue results in increased glucose uptake.

We also disclose a method for enhancing or inducing insulin sensitivity in a mammalian patient, comprising administering to the patient's adipose tissue a vector with the nucleic acid sequence to encode the Ad-36 E4 orf 1 protein; wherein expression of the encoded amino acid sequence in the patient's adipose tissue results in increased insulin sensitivity.

Ad-36 E4 orf 1 proteins can be used to increase insulin sensitivity and ameliorate symptoms due to diabetes, to attenuate lipodystrophy, to induce replication of stem cells, or to stimulate glucose uptake from muscle cells. The following are two of the possible approaches that may be used:

Using SEQ ID NO: 1 or SEQ ID NO: 2, purified protein of Ad-36 E4 orf 1 can be made, for example, using currently available recombinant protein production. Using the purified protein, the 3-D structure of the protein can be determined using X-ray crystallography. Using the knowledge of this structure, drugs can be identified or produced that would mimic the action of E4 orf 1 protein. These drugs could be used to target specific tissues for the desired effect, for example, adipocytes. For example, drugs could be delivered to preadipocytes using technologies such as surface engineered nano-particles or nanoparticle-aptamer bioconjungates. The purified protein could also be delivered to the tissues by techniques known in the field, such as targeted injection or using a gene-vector system to deliver the Ad-36 E4 orf 1 gene.

We expect that either the drugs mimicking the actions of the genes or the protein made in preadipocytes or in adipose tissue derived stem cells will promote their replication and differentiation, thereby increasing the number of fat cells. This will increase insulin sensitivity and attenuate hyperglycemia of diabetes. In addition, lipodystrophy is a condition marked by inability of preadipocytes to differentiate in adipocytes, thus resulting in ectopic storage of fat in the body and resulting in severe insulin resistance. Differentiation of fat cells induced by Ad-36 E4 orf 1 protein will provide mature fat cells for the storage of fat and attenuate associated co-morbidities.

In addition the nucleic acid sequence encoding Adenovirus-36 E4 orf 1 protein could be administered to the tissue using various gene therapy approaches. Among various systemic gene delivery approaches, injection of a gene into the tissue followed by electroporation has been shown to increase the level of expression of the injected gene. Other methods to introduce exogenous nucleic acid into the organs of the mammal include the following: DEAE Dextran transfection, calcium phosphate transfection, cationic liposome fusion, proptoplast fusion, creation of an in vivo electric field, DNA-coated microprojectile bombardment, injection with recombinant replication-defective viruses, homologous recombination, in vivo gene therapy, ex vivo gene therapy, viral vectors, and naked DNA transfer. These methods are well known by persons skilled in this art. See U.S. Patent Application Publication No. US 2002/0119945.

Considering the above described effects of Ad-36 E4 orf 1, routine assays such as the real time PCR, reverse transcription PCR, Northern blot analysis, enzyme linked immunosorbet assay (ELISA), Western Blot, or the like can be used to detect the presence of Ad-36 E4 orf 1 DNA, mRNA, or the respective protein in adipose tissue, blood, or other tissue or body fluids. This test could be used to predict insulin sensitivity of the subject.

We have discovered the following gene and amino acid sequences for Ad-36 E4 orf 1:

(1) Ad-36 E4 orf 1 DNA sequence
　　　　　　　　　　　　　　　　　　　　　　(SEQ ID NO. 1)
　　　ATGGCTGAATCTCTGTATGCTTTCATAGATAGCCCTGGAGG

GATCGCTCCCGTCCAGGAAGGGGCTAGCAATAGATATATCTTCTTTTGCC

CCGAATCTTTCCACATTCCTCCGCATGGGGTGATATTGCTTCACCTCAGA

GTGAGCGTGCTGGTTCCTACTGGATATCAGGGCAGATTTATGGCCTTGAA

TGACTACCATGCCAGGGGCATACTAACCCAGTCCGATGTGATATTTGCCG

GGAGAAGACATGATCTCTCTGTGCTGCTCTTTAACCACACGGACCGATTT

TTGTATGTCCGCGAGGGCCACCCAGTGGGAACCCTGCTGCTGGAGAGAGT

GATTTTTCCTTCAGTGAGAATAGCCACCCTGGTTTAG (2) Ad-36 E4 orf 1 Protein translation
　　　　　　　　　　　　　　　　　　　　　　(SEQ ID NO. 2)
　　　MAESLYAFIDSPGGIAPVQEGASNRYIFFCPESFHIPPHGV

ILLHLRVSVLVPTGYQGRFMALNDYHARGILTQSDVIFAGRRHDLSVLLF

NHTDRFLYVREGHPVGTLLLERVIFPSVRIATLV (3) Ad-36 E4 orf 1 ΔPDZ DNA sequence
　　　　　　　　　　　　　　　　　　　　　　(SEQ ID NO. 3)
　　　ATGGCTGAATCTCTGTATGCTTTCATAGATAGCCCTGGAGG

GATCGCTCCCGTCCAGGAAGGGGCTAGCAATAGATATATCTTCTTTTGCC

CCGAATCTTTCCACATTCCTCCGCATGGGGTGATATTGCTTCACCTCAGA

GTGAGCGTGCTGGTTCCTACTGGATATCAGGGCAGATTTATGGCCTTGAA

TGACTACCATGCCAGGGGCATACTAACCCAGTCCGATGTGATATTTGCCG

GGAGAAGACATGATCTCTCTGTGCTGCTCTTTAACCACACGGACCGATTT

TTGTATGTCCGCGAGGGCCACCCAGTGGGAACCCTGCTGCTGGAGAGAGT

GATTTTTCCTTCAGTGAGAATATAG (4) Ad-36 E4 orf 1 ΔPDZ protein translation
　　　　　　　　　　　　　　　　　　　　　　(SEQ ID NO. 4)
　　　MAESLYAFIDSPGGIAPVQEGASNRYIFFCPESFHIPPHGV

ILLHLRVSVLVPTGYQGRFMALNDYHARGILTQSDVIFAGRRHDLSVLLF

NHTDRFLYVREGHPVGTLLLERVIFPSVRI

The Ad-36 E4 orf 1 protein was shown to be different than other known gene sequences for other adenovirus E4 orf 1 proteins using the BLAST database. For example, the percent similarities with six adenoviruses are the following: Ad-9, 92%; Ad-46, 92%; Ad-12, 47%; Ad-50, 47%; Ad-3, 47%; and Ad-7, 47%.

EXAMPLE 1

Materials and Methods

Abbreviations and roles of various compounds used herein are the following:

| Abbreviation | Compound and Role in this study |
|---|---|
| cAMP | Cyclic adenosine mono-phosphate; Indicates cellular differentiation and lipid accumulation |
| CEBPs | CCAAT enhancer binding proteins α, β, δ; indicator genes of preadipocyte differentiation cascade |
| CREBP | Cyclic AMP response element binding protein: Indicates cAMP activation |
| Glut 1 | Glucose transporter 1: Participates in insulin independent glucose uptake |
| Glut 4 | Glucose transporter 4: Participates in insulin stimulated glucose uptake |
| IL | Interleukins (cytokines of immune response), Indicates inflammation |
| MCP-1 | monocyte chemoattractant protein1; indicates inflammation |
| MIF | Macrophage inhibitory factor 1; prevents migration of macrophages |
| P38 (MAPK) | P38 mitogen activated protein kinase; key molecule in cell differentiation |
| PI3K | Phosphotidyl inositol-3' kinase: pivotal enzyme and indicator of cellular differentiation, proliferation, angiogenesis, glucose uptake and lipid accumulation |
| PKB | Protein kinase B: Indicates PI3k activation |
| PPARγ2 | Peroxysomal proliferators activator receptor γ2: key transcription factor involved in preadipocyte differentiation and insulin sensitivity |
| Wnt10b | Acts as a brake on differentiation of preadipocytes. Expression decreases as preadipocytes differentiate in adipocytes |

Isolation of hASC: Liposuction aspirates from subcutaneous adipose tissue sites were obtained from subjects undergoing elective plastic surgery. Tissue was washed 3 times with PBS and suspended in equal volume of phosphate buffered solution (PBS) supplemented with 0.1% collagenase type I from *Clostridium histolyticum* (cat #LS004196, Worthington) and 1% Albumin from bovine serum essentially fatty acid free, ≧96%, and lyophilized powder (cat #A6003, Sigma Chemical Co., St. Louis, Mo.) for 1 hour at 37° C. under mild controlled agitation at approximately 75 rpm. Tubes were centrifuged at 1,200 rpm at room temperature for 5 minutes, followed by 10 seconds of vigorous shaking, and the centrifugation step was repeated. Supernatant was removed, and cell pellet was re-suspended in 10 ml of sterile PBS with 1% BSA, followed by centrifugation at 1200 rpm for 5 min at room temperature. Cell pellet was re-suspended in stromal media, and 200 μl of cell suspension was exposed to Red Blood Cell Lysing Buffer Hybri-Max (cat #R7757, Sigma) for 20 min followed by cell count using a homocytometer and Trypan Blue solution 0.4% (cat #T8154, Sigma).

Culturing human or rat ASC: The ASC were grown in stromal media containing Dulbecco's Modified Eagle's Medium/Ham's Nutrient Mixture F12 (DMEN/F12)1:1, 3.151 Glucose, Glutamine, Phenol Red, HEPES, 1.2 Sodium Bicarbonate, Sodium Pyruvate (cat #SH30023.01, HyClone), supplemented with 10% FBS (cat #SH30070.03, HyClone) and 1× antibiotic-antimycotic solution (cat #A-5955, Sigma) containing 10,000 units of penicillin, 10 mg Streptomycin and 25 μg Amphotericin B per ml.

Ad-36 inoculation of hASC: Passage 2 hASC were inoculated with stromal media (CON) or Ad-36 at 2.7 MOI for 1 hour. Then media was replaced with fresh stromal media. Cells were maintained in culture for 9 or 12 days, and media was replaced every 3 days.

Osteogenic differentiation of hASC: Passage 2 hASC were cultured until 80-90% confluent. The Ad-36 group was inoculated with the virus, and both groups (Ad-36 and CON) were provided with stromal media for 3 days. On day 1 of osteogenic induction, media was replaced with osteoblast induction medium containing DMEM with 10% FBS, 10 mM β-Glicerophosphate, 0.15 mM ascorbate-2-phosphate, 10 nM dexametazone, 100 U/ml penicillin and 100 ug/ml streptomycin. Cells were maintained in culture for 6 days post osteogenic induction.

Construction of 3T3-L1 cells stably expressing Ad-36 E4 orf 1 or E1A genes: To determine the contribution of individual Ad-36 candidate genes, retrovirus vectors were constructed to transduce individual Ad-36 genes into 3T3-L1 cells and to select cells expressing these genes. The vector LXSN contains a multiple cloning site for insertion of genes of interest and the neomycin resistance gene for selection of cells transduced by the vector. 3T3-L1 cells were infected with LXSN vectors expressing either the Ad-36 E1A gene, the Ad-36 E4 orf 1 gene, Ad-36 E4 orf 1 gene with PDZ binding domain deleted (E4 orf-1 dPDZ) or empty vectors. Post confluence, even without MDI induction, E4 orf 1 cells began to accumulate lipid, slightly earlier than nontransduced (control) 3T3-L1 cells or cells transduced with the null vector (data not shown).

Determination of lipid accumulation: Oil Red 0 is a lipid specific stain. This assay is based on the fact that the degree of staining of fat cells with Oil Red 0 is proportional to the extent of lipid accumulation. Cells are fixed for 1 h with 10% formalin solution (cat #HT551128, Sigma), then washed with water and stained for 2 h with Oil Red O (cat #BP 112-10, Fisher), followed by exhaustive rinsing with water. After evaporating the excess water at 32° C., the dye was extracted with isopropyl alcohol (cat #190764, Sigma) by rocking the plates for 5 minutes and its absorbance was read at 510 nm.

DNA extraction: Total DNA was extracted using DNeasy Tissue Mini Kit (cat #69504, Qiagen) based on advanced silica-gel-membrane technology for rapid and efficient purification of total cellular DNA without organic extraction or ethanol precipitation. DNA samples were stored at −80° C. until used for amplification.

RNA extraction and cDNA synthesis. RNA was extracted using the RNeasy Mini Kit, which combines the selective binding properties of a silica-gel-based membrane with the speed of microspin technology as per the manufacturer's instructions (cat #74104, Qiagen). Residual DNA was eliminated by using Amplification Grade Deoxyribonuclease I (cat #18068-015, Invitrogen) which digests single and double stranded DNA to oligodeoxy-ribonucleotides containing 5'-phosphate. One μg of total RNA was reverse-transcribed to cDNA using iScrip™ cDNA Synthesis Kit (cat #170-8890, Bio-Rad) as per the manufacturer's protocol. Samples were stored at −80° C. until used for amplification.

Two step qualitative RT-PCR: PCR core system II (cat #M7665, Promega) was used for the amplification of cDNA, obtained as described above. Water was used a negative PCR control. Positive PCR control was DNA from Ad-36 infected A-549 cells. The reaction mixture contained 1.5 mM $MgCl_2$, 1× Thermophilic DNA polymerase reaction buffer, Nucleotide mix containing 200 μM of each nucleotide, 1 μM each of upstream and down stream primers, 1 μG of DNA template and 1.25 units of Taq DNA polymerase. The total volume was made up to 50 μL with DNAse free water. DNA was denatured for 2 min at 95° C. and subjected to 35 cycles of PCR (94° C. for 1 min, 58° C. for 1 min, 72° C. for 2 min) followed by extension at 72° C. for 5 min. PCR products were visualized on a 1.2% agarose gel with a 100 bp DNA ladder (cat #G-2101, Promega).

Quantitative Real-Time PCR (qRT-PCR): A standard was generated using cDNA or DNA (depending on the experimental design) pooled from the experimental samples. At least 3 data points, representing 10-fold dilutions, were required for generating a standard curve. Non template control reaction mixtures contained water instead of sample. Real-time quantitative PCR was carried out in optical 96 or 384 well reaction plates using ABI PRISM 7700 sequence detector (Applied Biosystems, Branchburg, N.J.) using a SYBER Green detection system (cat #170-8880, Bio-Rad). The reaction mixture contained 2.5 μL of the 10× SYBER green buffer, 1 mM each of dATP, dGTP, dCTP and dUTP, 2 mM $MgCl_2$, 0.625 units of iTaq DNA polymerase, 200 nM each of the forward and reverse primers, 50 ng cDNA or 40 ng DNA and water to attain a final volume of 25 μL. Both samples and standards were run in duplicate, and each transcript level was adjusted to the housekeeping gene used (β actin for the rat samples or Cyclophilin B for human samples). The reactions were performed using the following parameters: one cycle of 48° C. for 30 min, then 95° C. for 10 min, followed by 40 cycles at 95° C. for 15 s and 60° C. for 1 min. The amount of mRNA for the genes of interest relative was expressed as relative to the housekeeping gene.

EXAMPLE 2

Ad-36 Induces Differentiation and Lipid Accumulation in Human Adipose Tissue Derived Stem Cells (hASC)

Figure 1A:
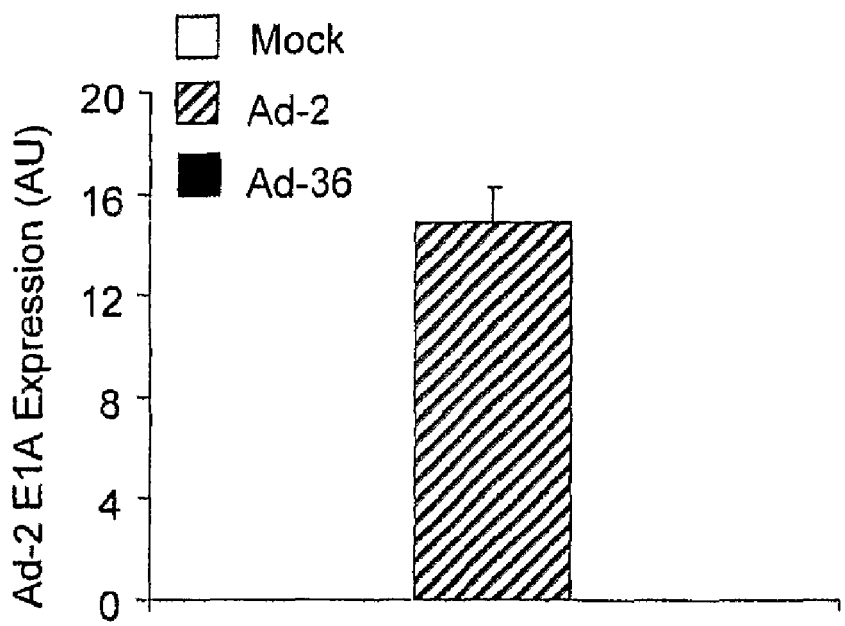
FIG. 1A illustrates the Ad-2 mRNA isolated from human adipose stem cells (hASC) 1 day after infection with Ad-2 virus (multiplicity of infection (MOI) of 3.8).
Figure 1B:
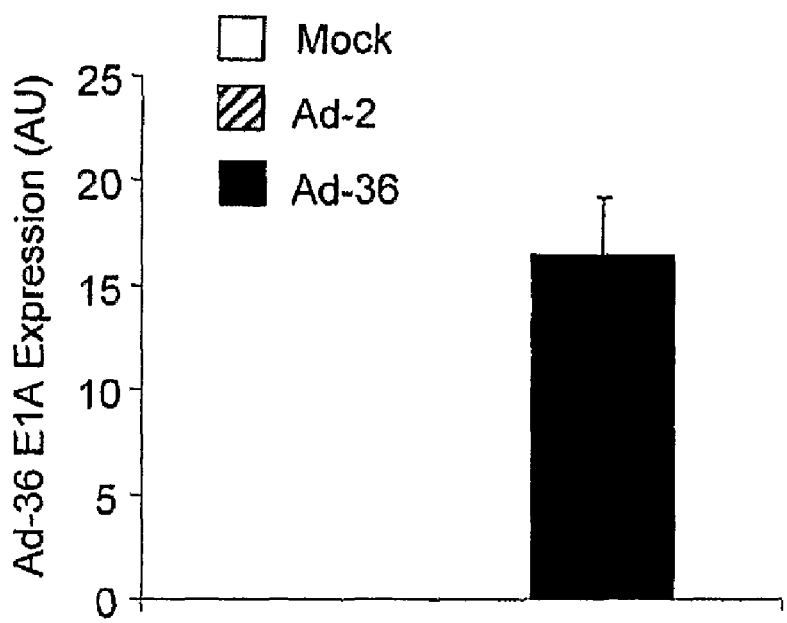
FIG. 1B illustrates the Ad-36 mRNA isolated from hASC cells 1 day after infection with Ad-36 virus (3.8 MOI).
Figure 2A:
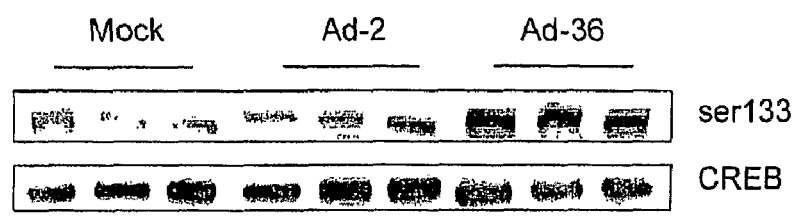
FIGS. 2A-2C illustrate a Western blot analysis for CREB (FIG. 2A), PKB (FIG. 2B), and p38 (FIG. 2C) proteins from lysates of hASC 24 h after infection with Ad-2 (MOI 3.8), Ad-36 (MOI 3.8), or with media (mock).
Figure 2B:
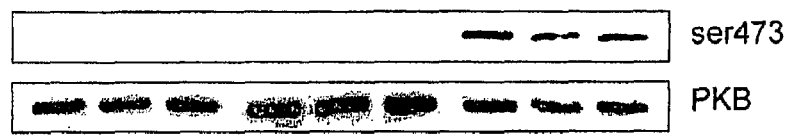
Figure 2C:
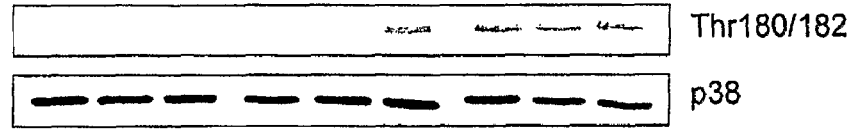

Rat preadipocytes (3T3-L1) provide a convenient in vitro model for studying adipogenesis. However, to determine the relevance of Ad-36 induced adipogenesis to humans, the effects of Ad-36 and Ad-2 infection were studied in primary hASC cultures. At confluency, hASC cultures were serum deprived for 18 h prior to infection with Ad-2 or Ad-36 at MOI 3.8. Both Ad-2 and Ad-36 viral gene expression was observed in experimentally infected hASC cultures (FIGS. 1A and 1B). FIG. 1A shows Ad-2 mRNA expression as isolated after one day infection, and FIG. 1B shows Ad-36 mRNA expression. After 24 h infection, proteins were isolated and analyzed by Western blotting. In FIG. 2A, CREB phosphorylation is shown to increase as a result of Ad-36 infection when compared with mock infection ($p<0.012$). In FIG. 2B, PKB phosphorylation is shown to increase in Ad-36 infected cultures as compared to mock infection ($p<0.010$). In FIG. 2C, p38 phosphorylation is also increased in Ad-36 infected cultures as compared to mock infection ($p<0.005$). Thus, in the absence of differentiation inducers, only Ad-36 was able to induce adipogenesis. Ad-36, but not Ad-2, increased both CREB and PKB phosphorylations.

Figure 3:
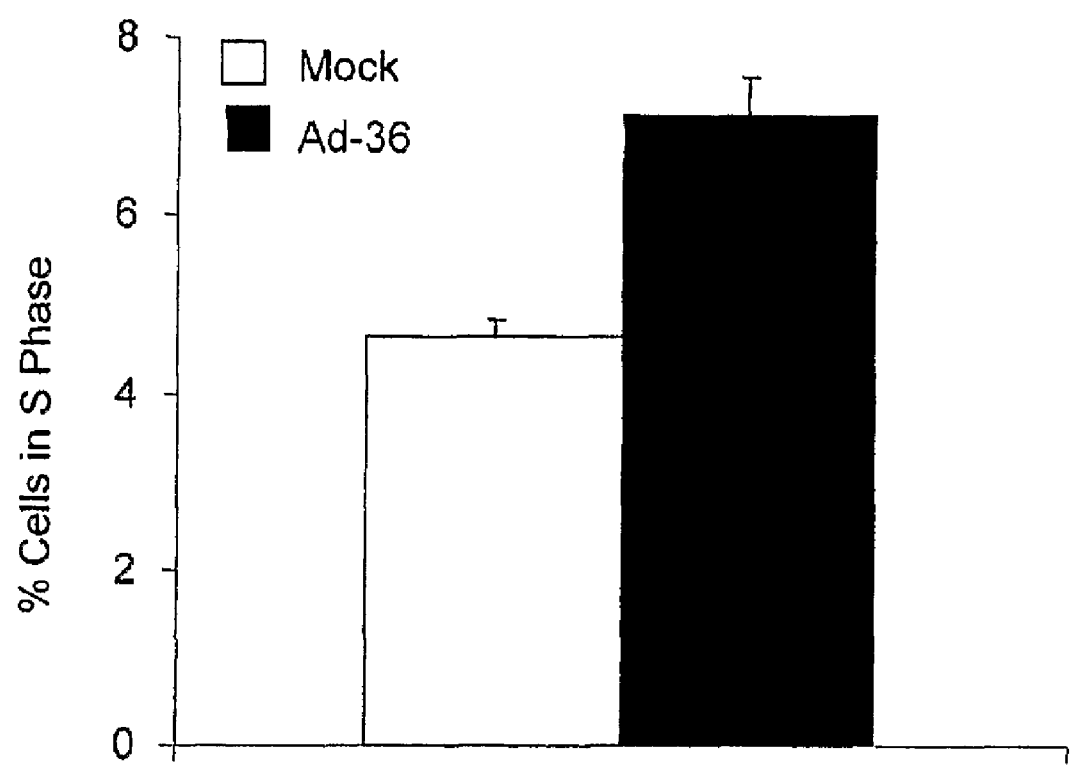
FIG. 3 illustrates the amount of cell proliferation (expressed as % cells in S phase) of hASC 32 h after infection with Ad-36 (MOI 3.8) or media-infected (mock).
Figure 4A:
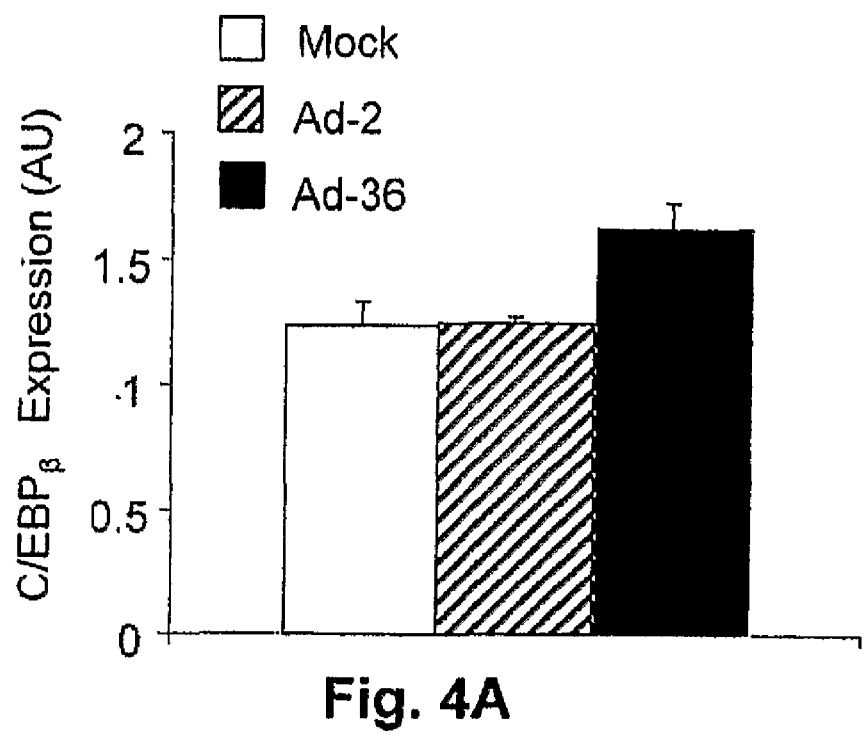
FIG. 4A illustrates the degree of C/EBPβ expression in hASC 1 day after infection with Ad-36 (MOI 3.8) or media-infected (mock).
Figure 4B:
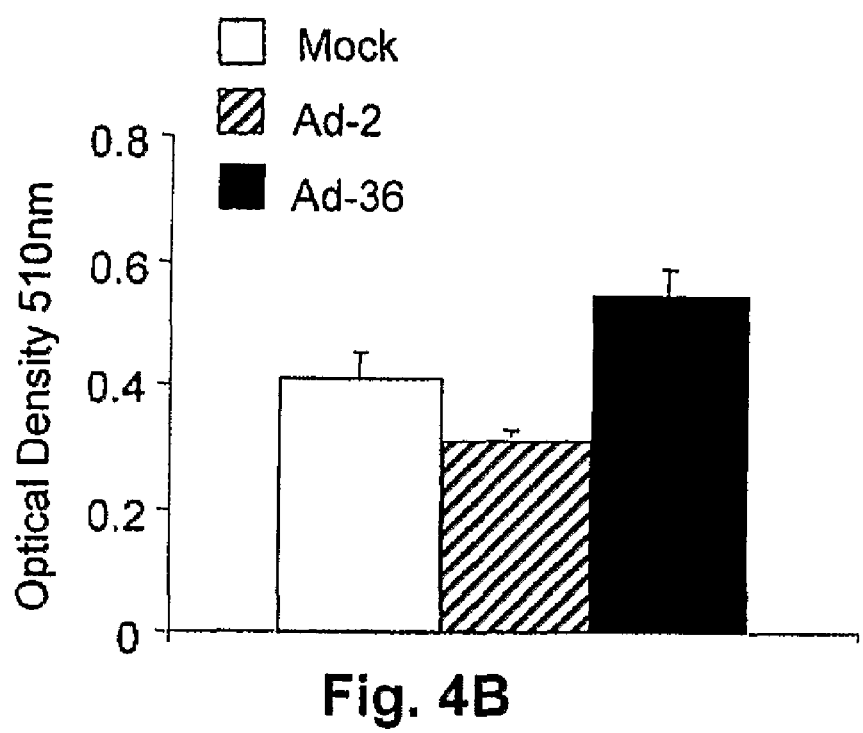
FIG. 4B illustrates the degree of lipid accumulation in hASC 5 days after infection with Ad-36 (MOI 3.8) or media-infected (mock).
Figure 5:
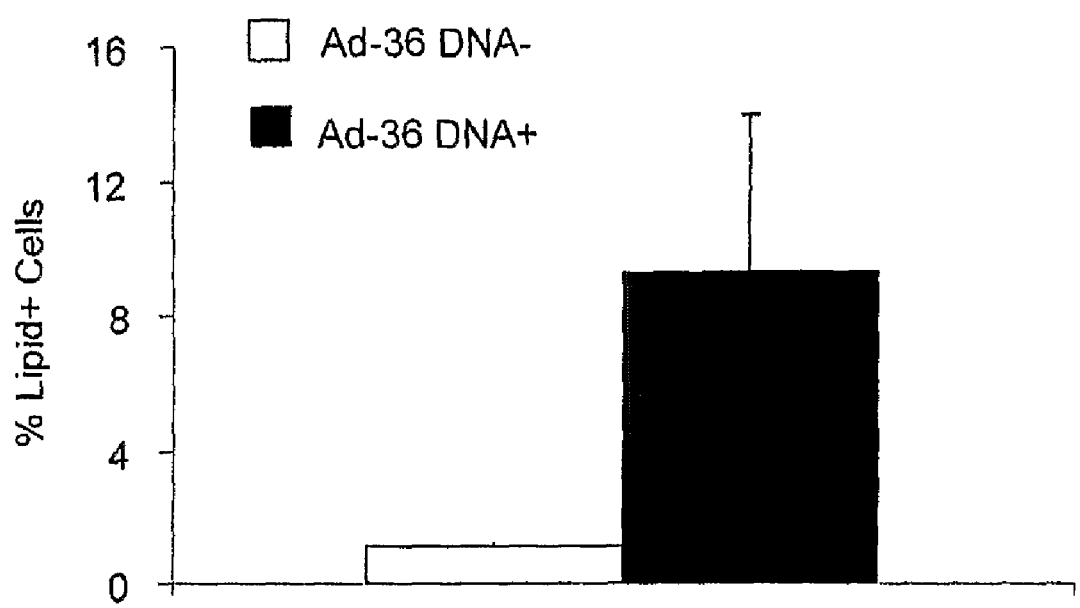
FIG. 5 illustrates the degree of response to differentiation media, expressed as % lipid staining cells, in hASCs isolated from Ad-36 DNA+ human subjects as compared to Ad-36 DNA− human subjects.

Cell proliferation was determined by BrdU incorporation at 32 h. Flow cytometry analysis was used to determine the percent cells in S phase. The percent was found to be higher in Ad-36 infected cultures as compared to mock infection ($p<0.007$) (FIG. 3). Moreover, Ad-36, not Ad-2, upregulated phosphorylation of p38 (FIG. 2C), which is required for 3T3-L1 and human preadipocyte differentiation through phosphorylation of C/EBPβ. Ad-36 infected hASC cultures showed increased C/EBPβ gene expression and lipid accumulation, an effect not seen in Ad-2 infected hASC cultures (FIG. 4A and FIG. 4B). C/EBPβ expression was increased on day 1 in Ad-36 infected cultures as compared to mock infected cultures (p<0.040). In addition, lipid accumulation was greater in Ad-36 infected cultures on day 5 as compared to mock infected cultures (p<0.004). In FIG. 5, hASCs from Ad-36 DNA+ human subjects had a stronger response to differentiation media as compared to Ad-36 DNA− human subjects (p<0.003).

Thus Ad-36 was shown to induce differentiation; to increase cAMP, P13K and p38 MAPK pathways; and to induce lipid accumulation in human adipose tissue derived stem cells, which are cells considered to include progenitor cells of adipocyte lineage.

EXAMPLE 3

E4 orf-1 is Sufficient and Necessary to Induce Lipogenic Changes

To conclusively demonstrate that E4 orf-1 is required for Ad-36 induced adipogenesis, siRNA was used to selectively knockdown E4 orf 1 expression in 3T3-L1 and hASC cultures infected with Ad-36. Ad-36 E4 orf-1 siRNA greatly reduced E4 orf 1 mRNA levels 24 h and 48 h post infection in Ad-36 infected 3T3-L1 cells and completely abolished the expression in hASC cultures 24 h post infection (data not shown). Ad-36 E4 orf 1 siRNA-mediated knockdown of E4 orf 1 gene expression resulted in the abolishment of the pro-adipogenic effects of Ad-36 on cAMP and PI3K pathways, pro-adipogenic genes, and lipid accumulation in hASC cultures.

At confluency, hASC cultures were serum deprived for 18 h prior to infection with Ad-36 E4 orf 1 siRNA, Ad-36+NC siRNA or Ad-36+E4 orf 1 siRNA. In FIGS. 6A-6C, proteins were harvested 24 h after infection and analyzed by Western blotting for CREB (FIG. 6A), PKB (FIG. 6B) and p38 (FIG. 6C) proteins. FIG. 6A illustrates that CREB phosphorylation increased with Ad-36+NC siRNA compared to mock infection (p<0.001) and compared with Ad-36+E4 orf 1 siRNA (p<0.018). FIG. 6B illustrates that PKB phosphorylation increased in Ad-36+NC siRNA compared to mock (p<0.004) and compared to Ad-36+E4 orf 1 siRNA (p<0.018). Finally, FIG. 6C illustrates that p38 phosphorylation increased in Ad-36+NC siRNA as compared to mock infection (p<0.013) and compared to Ad-36+E4 orf 1 siRNA (p<0.003). In FIGS. 6A-6C, protein expression in cells infected with Ad-36+E4 orf 1 siRNA were not significantly different than mock infection.

RNA was harvested from cells infected as above preinfection (day 0), and on days 1, 2, and 3. Cells were fixed on day 0, preinfection, and on days 4 and 6 for Oil Red O staining. In FIG. 7A, Wnt10b expression was shown to decrease on day 1 in Ad-36+NC siRNA as compared to mock (p<0.002), and as compared to Ad-36+E4 orf 1 siRNA (p<0.005). In FIG. 7B, C/EBPβ expression was shown to increase on day 2 in Ad-36+NC siRNA as compared to mock (p<0.001) and Ad-2 (p<0.001). In FIG. 7C, PPARγ2 expression is shown to increase on day 3 as compared to mock (p<0.006) and to Ad-36+E4 orf 1 siRNA (p<0.032). In FIG. 7D, lipid accumulation was shown to be greater in Ad-36+NC siRNA on day 6 as compared to mock (p<0.002) and to Ad-36+E4 orf 1 siRNA (p<0.032). Thus, without E4 orf 1 activity, Ad-36 infection did not result in increased differentiation as evidenced by elevated Wnt10b expression, decreased C/EBPβ and PPARγ2 expression and decreased lipid accumulation as compared to wild type Ad-36 infection (FIGS. 7A-7D). These results implicate Ad-36 E4 orf 1 activity in pro-adipogenic effects of Ad-36 infection in rodent and, more importantly, in human adipose tissue.

Ad-36 E4 orf 1 was found to be sufficient and necessary to induce lipogenic changes in 3T3-L1 and hASC (as shown by siRNA against Ad-36 E4 orf-1). Furthermore, E4 orf 1 is required for Ad-36 induced upregulation of cAMP, PI3K and p38 MAPK pathways, and for induction of adipogenic gene expressions such as C/EBPβ and PPARγ2 in hASC. Induction of adipogenesis and PPARγ2 are linked with improvement in insulin sensitivity (63, 64).

To determine if the E4 orf 1 induced increase in lipids is due to cell hypertrophy or to a greater number of cells that store lipids, confluent 3T3-L1, and 3T3-L1 cells expressing null vector, E4 orf 1, or E4 orf 1 dPDZ were treated with or without MDI. The cells were stained with Nile Red, a lipid-specific dye, and the percent of stained cells were determined by a FACS assay. As shown in FIGS. 22A and 22B, Ad-36 E4 orf 1 expressing cells had the greatest number of lipid containing cells with (FIG. 22A) or without MDI (FIG. 22B) and deletion of PDZ-binding domain attenuated the pro-differentiation effect of E4 orf 1. This is the first evidence of the role of PDZ-domain binding domain of E4 orf 1 as a functional motif that imparts adipogenic property to the gene.

cAMP contributes to replication and differentiation. cAMP levels were measured in synchronized confluent 3T3-L1 cells stably expressing Ad-36 E4 orf 1, Ad-36 E4 orf 1 dPDZ cells, or wild type confluent 3T3-L1 cells. cAMP was determined using cAMP direct immunoassay kit (Biovision, cat #371-100). cAMP showed significantly greater levels in E4 orf-1 expressing cells compared to wild type 3T3-L1 cells or Ad-36 E4 orf 1 dPDZ cells (p=0.025; FIG. 22C). The cAMP enhancing effect of Ad-36 E4 orf 1 was abolished by deletion of the PDZ binding domain. cAMP activation results in activation of CREB by its phosphorylation; and phospho-CREB strongly activates C/EBP β promoter-reporter genes, induces expression of C/EBPbeta, and causes adipogenesis. As described above, the total and phosphorylated CREB protein was determined by Western Blot analysis 24 h post re-feeding, in confluent cell cycle synchronized 3T3-L1 cells stably expressing E4 orf 1, E4 orf 1 dPDZ, or in wild type 3T3-L1 cells. E4 orf 1 expressing cells had greater phosphorylated CREB (p<0.003; FIG. 22D), and this effect was attenuated by E4 orf 1 dPDZ (FIG. 22D).

Confluent, 3T3-L1 cells stably expressing Ad-36 E1A, Ad-36 E4 orf 1, Ad-36 E4 orf 1 dPDZ, or the null vector were fed 10% FBS after 18 h serum deprivation. Cells were harvested 24 h later for protein, and Western Blot analysis was performed for PKB activity and MAPK (used as loading control). Immobilized PKB monoclonal antibody was used to immunoprecipitate PKB from cell extracts (100 μg total protein). Using a non-radioactive PKB Activity Assay Kit (Cell Signaling, Beverly, Mass.), an in vitro assay was performed using GSK-3 fusion protein as a substrate for the bound PKB. PKB activity was reported as a measure of phosphorylation of GSK-3 by Western blotting using a phospho-GSK-3 (ser21/9) antibody. E4 orf 1 showed greater PKB activity at 24 hr (FIG. 22E). Activation of PKB is PI3K activation dependent and considered as an indication of PI3K activation. PKB activation without insulin stimulation indicates that in presence of Ad-36 E4 orf 1, insulin is not required for inducing PI3K signaling.

Finally, RNA extracted 2 d post confluence from E4 orf 1 expressing cells and 3T3-L1 cells was used to determine CEBP/P expression using qRT-PCR. P actin was used as an internal control, and CEBP/β expression by 3T3-L1 cells was considered as 1. FIG. 22F indicates an 8-fold greater CEBP/β expression in the E4 orf 1 expressing cells.

Ad-36 E4 orf 1 expressing cells increased spontaneous differentiation, and enhanced cAMP and insulin signaling pathways as determined by elevated cAMP levels, cAMP response element binding protein activity, and PI3 Kinase activity. The role of Ad-36 E4 orf 1 in differentiation was further confirmed by attenuating its expression in Ad-36 infected 3T3-L1 cells by RNAi technique, which significantly reduced lipid accumulation. These data show that E4 orf 1 enhances cAMP and insulin signaling pathways and induces differentiation in preadipocytes. This indicates that E4 orf 1 is necessary for the adipogenic effect of Ad-36 in hASC. In summary, via its E4 orf 1 gene, Ad-36 induces differentiation of preadipocytes in humans and contributes to the adipogenic effect of the virus.

EXAMPLE 4

Ad-36 Improves Insulin Sensitivity or Treats Lipodystrophy

Figure 8A:
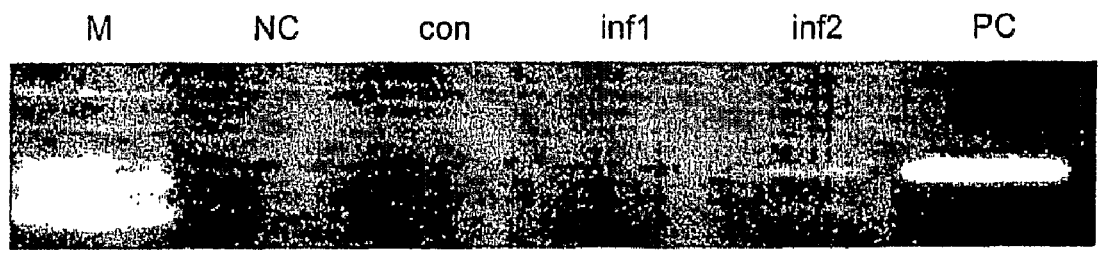
FIG. 8A illustrates the degree of Ad-36 E4 orf 1 gene expression from adipose stem cells from Wistar rats 4 days after being infected with Ad-36, control (not infected), Inf1 (Rat 1 infected with Ad-36), Inf2 (Rat 2 infected with Ad-36), Ad-2 (NC, negative control), and PC (positive control; A549 cells infected with Ad-36).

Ad-36 infects ASC ex-vivo: Ad-36 induced adiposity in rats 6 months post-inoculation and increased preadipocyte differentiation in rodent cell lines. A test was conducted to determine if Ad-36 early genes were expressed in adipose stem cells (ASC) obtained from adipose tissue of Ad-36 infected rats. Ad-36 E4 orf 1 was expressed in ASC extracted from epididymal tissue of Wistar rats 4 days post-inoculation with Ad-36, but was absent in rats inoculated with media. (FIG. 8A). FIG. 8A shows the expression of Ad-36 E4 orf 1 gene in rats after 4 days inoculation with media or Ad-36, ASC of the Ad-36 infected rats expressed Ad-36 E4 orf 1 (inf1 and inf2), compared to no expression in the control (con) group, and with positive (PC, infected with Ad-36) and negative controls (NC, infected with Ad-2), respectively. This indicated that the Ad-36 adipogenic gene, E4 orf 1, is expressed in adipose tissue of experimentally infected animals, suggesting viral replication and subsequent direct effect of Ad-36 in adipose tissue.

Figure 8B:
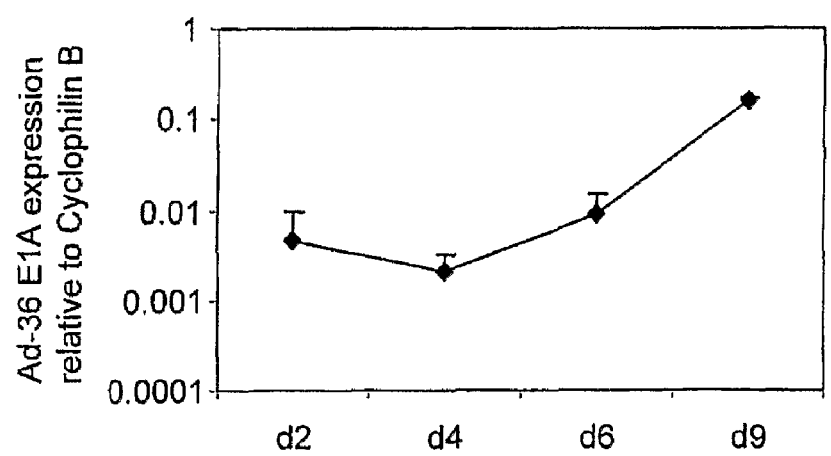
FIG. 8B illustrates the temporal change in Ad-36 E1A gene expression from adipose stem cells of Wistar rats from day 2 to 9 after infection with Ad-36 (intranasal infection with about $10^{12}$ PFU).
Figure 8C:
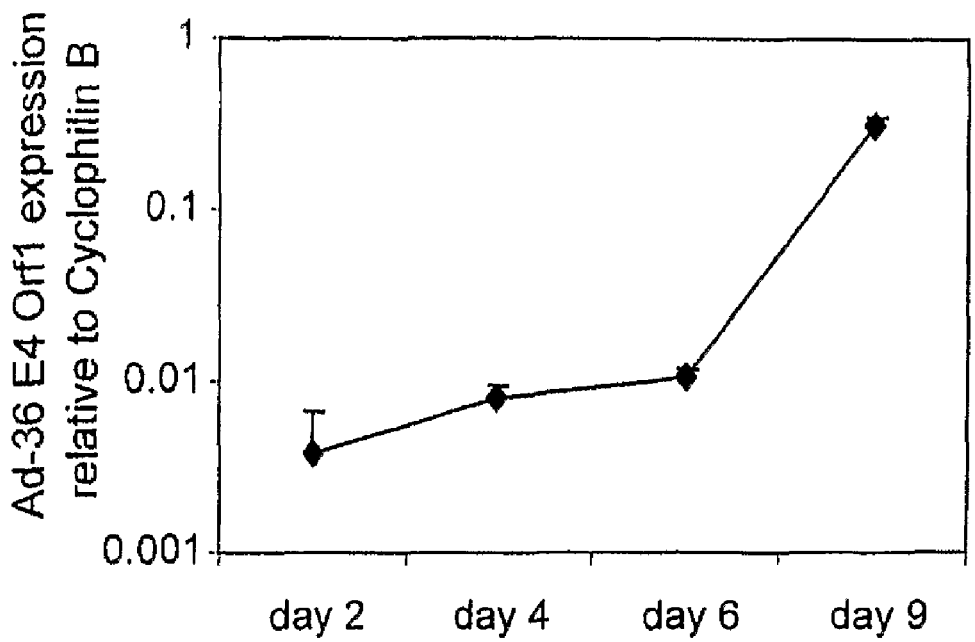
FIG. 8C illustrates the temporal change in Ad-36 E4 orf 1 gene expression from adipose stem cells of Wistar rats from day 2 to 9 after infection with Ad-36 (intranasal infection with about $10^{12}$ PFU).
Figure 8D:
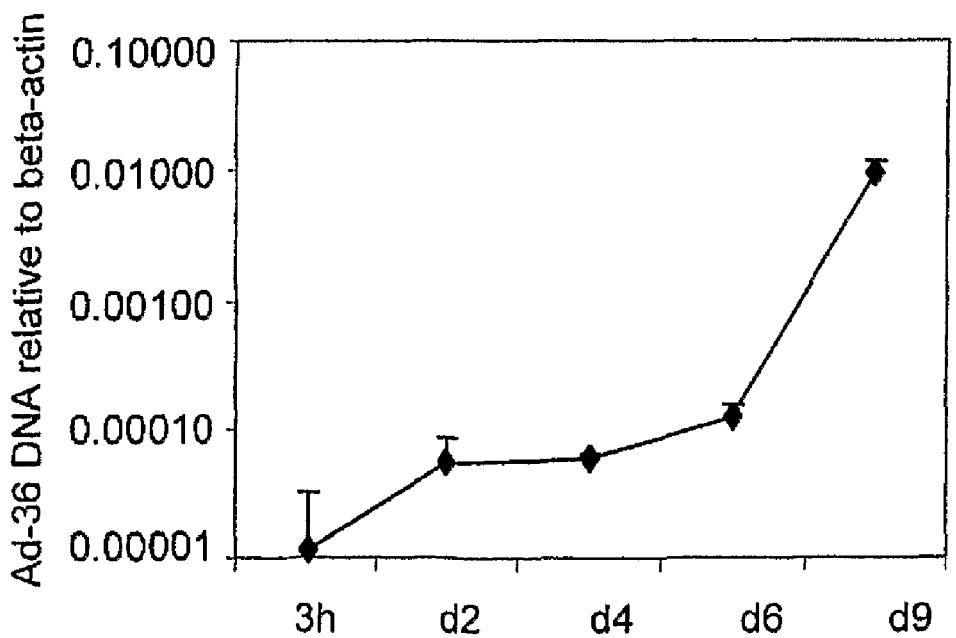
FIG. 8D illustrates the temporal change in Ad-36 DNA from adipose stem cells of Wistar rats from 3 h to 9 days after infection with Ad-36 (intranasal infection with about $10^{12}$ PFU).

Ad-36 infects ASC in-vitro: A time course of Ad-36 infection in hASC was determined by measuring early gene E1A and E4 orf 1 expression for 9 days after inoculation. Pre-confluent hASC infected with Ad-36 showed continued Ad-36 DNA and E1A and E4 orf 1 expression. Ad-36 genes E1A (FIG. 8B) and E4 orf 1 (FIG. 8C) are expressed and Ad-36 genomic DNA increases over time (FIG. 8D). RNA and DNA were determined by qRT-PCR, and values represented in logarithmic scale (N=3; Mean±SD). (FIGS. 8B, 8C, 8D). These results suggest that hASC are capable of supporting Ad-36 gene expression and replication.

Figure 9A:
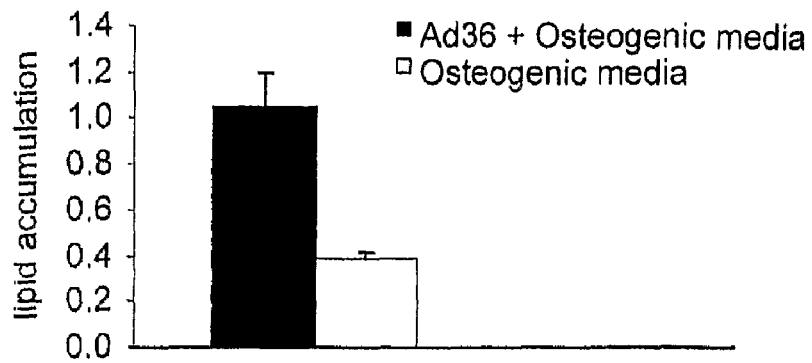
FIG. 9A illustrates the difference in lipid accumulation in hASC inoculated with either Ad-36 (Ad-36+Os; MOI 2.7) or media (Os), and after three days incubated in osteogenic media for 6 days.
Figure 9B:
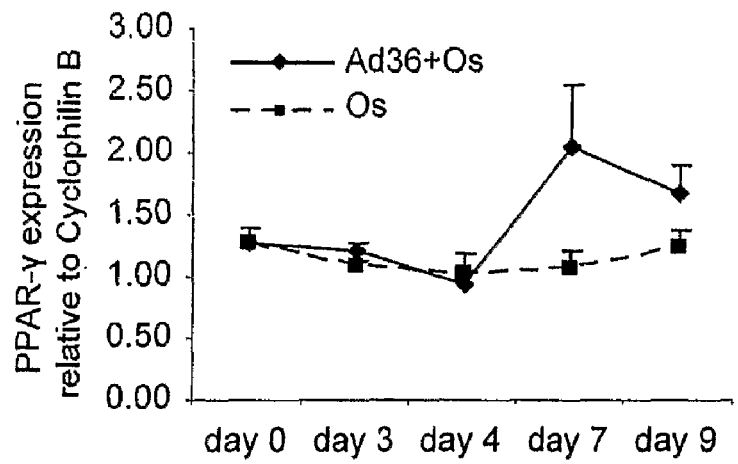
FIG. 9B illustrates the difference in PPAR-γ expression determined by qRT-PCR in hASC inoculated with either Ad-36 (Ad-36+Os; MOI 2.7) or media (Os), and after three days incubated in osteogenic media for 6 days.
Figure 9C:
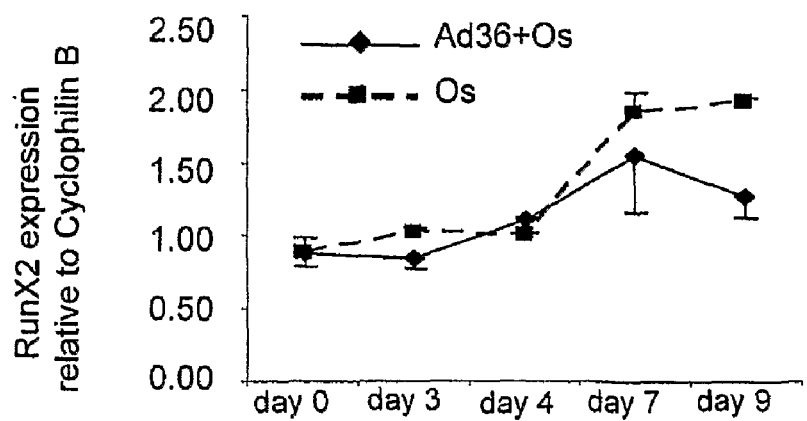
FIG. 9C illustrates the difference in RunX2 expression determined by qRT-PCR in hASC inoculated with either Ad-36 (Ad-36+Os; MOI 2.7) or media (Os), and after three days incubated in osteogenic media for 6 days.

Ad-36 induces commitment of hASC to adipocyte lineage: hASC were inoculated with either media (CON) or Ad-36. After 72 h both groups were incubated with osteogenic media, which normally commits ASC to osteogenic lineage. The Ad-36, inoculated group showed increased lipid accumulation as determined by Oil Red O (FIG. 9A), greater PPAR-γ (FIG. 9B) and lower RunX2 (FIG. 9C) expression, as determined by qRT-PCR (N=3; Mean±SD). Cells inoculated with Ad-36 showed significantly greater lipid accumulation 9 days post inoculation, greater expression of PPARγ, a key gene of adipogenic pathway, and reduced expression of RUNx2, a key gene of osteogenic pathway. These results indicate that Ad-36 commits stem cells to adipocyte lineage, even in presence of osteogenic inducers.

Figure 10A:
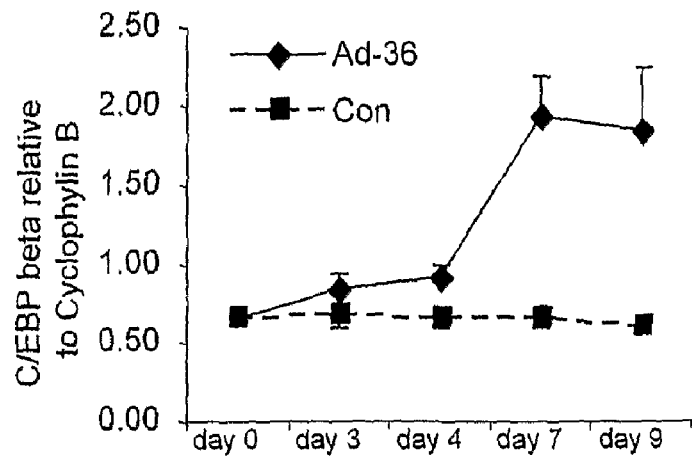
FIG. 10A illustrates the difference in CCAAT/enhancer binding protein β (C/EBP-β) expression determined by qRT-PCR in hASC for up to 9 days after infection with either Ad-36 (MOI 2.7) or media (Con).
Figure 10B:
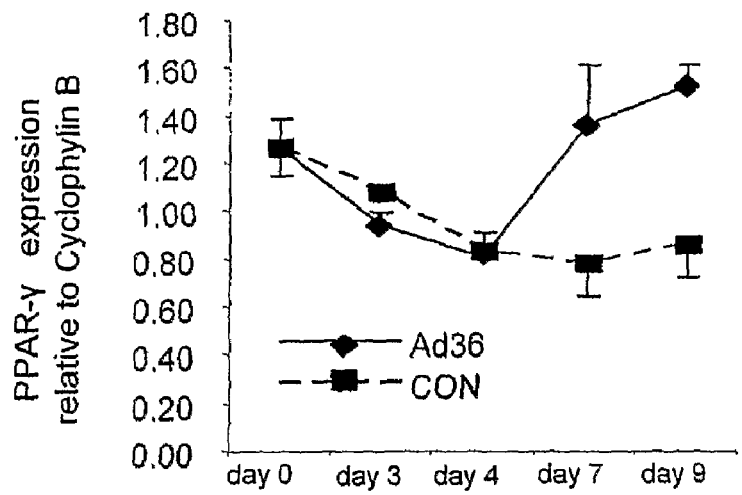
FIG. 10B illustrates the difference in peroxisome proliferator activator receptor γ2 (PPAR-γ2) expression determined by qRT-PCR in hASC for up to 9 days after infection with either Ad-36 (MOI 2.7) or media (Con).

Ad-36 induces C/EBPβ and PPARγ expression: C/EBPβ and PPARγ are genes involved in differentiation of pre-adipocyte and possible targets for Ad-36 induced lipid accumulation. Using qRT-PCR, it was shown that Ad-36 significantly increased C/EBP-β ($p<0.01$, FIG. 10A) and PPARγ ($p<0.001$, FIG. 10B) gene expression 9 days post-infection, in the absence of any adipocyte induction agents. This indicates that Ad-36 induces differentiation of hASC partially by up-regulating C/EBPβ and PPARγ gene expression.

Figure 10C:
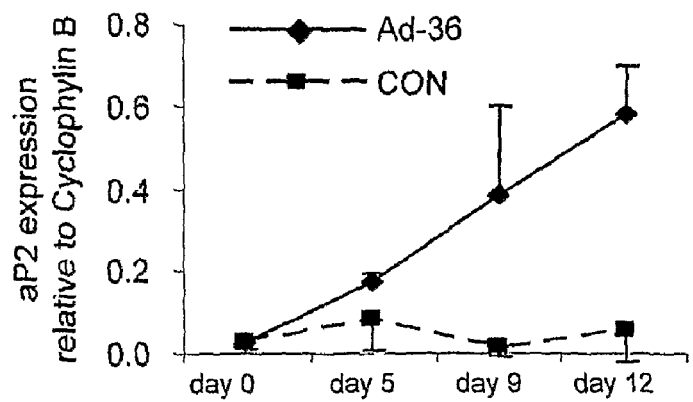
FIG. 10C illustrates the difference in aP2 expression determined by qRT-PCR in hASC for up to 9 days after infection with either Ad-36 (MOI 2.7) or media (Con).

Ad-36 induces αP2 expression: Fatty acid binding protein (aP2) is extensively used as a marker of differentiation of uncommitted cells to mature adipocytes. Therefore, aP2 expression levels were measured by qRT-PCR in Ad-36 infected and uninfected (CON) hASC. hASC expressed significantly higher levels of aP2 5 days ($p<0.01$), 9 days ($p<0.05$) and 12 days ($p<0.01$) post-inoculation with Ad-36, in the absence of induction cocktail (FIG. 10C), showing that Ad-36 induces terminally differentiation of hASC.

Figure 11A:
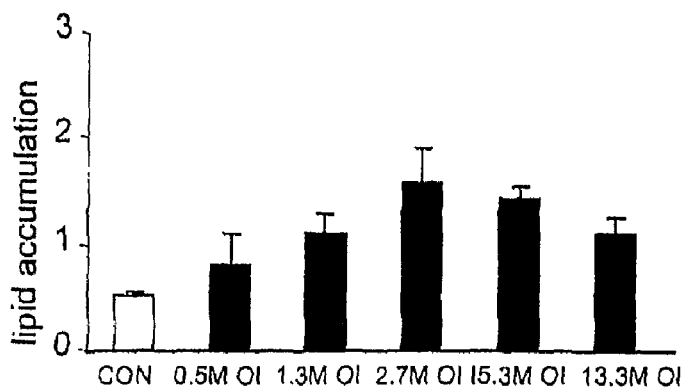
FIG. 11A illustrates the difference in lipid accumulation (determined by Oil Red-O staining) in hASC after 9 days of infection with increasing MOI of Ad-36, from about 0.5 to about 13.3, and with media (CON).

Ad-36 induces and enhances lipid accumulation in hASC: Spontaneous lipid accumulation is defined as lipid accumulation present in the absence of any adipogenic agents (e.g., insulin, dexamethasone, methyl-isobutyl xanthine, thiazolidinedione). Multiple MOIs (multiplicity of infection) were used to infect hASC, and lipid accumulation was determined 9 days later by Oil Red-O assay. Lipid accumulation in hASC in response to increasing MOI of Ad-36 is shown in FIG. 11A. The Ad-36 infected group showed increased lipid accumulation in the order of increasing virus dose (MOI), up a MOI of 2.7 ($p<0.03$, FIG. 11A). This shows that Ad-36 induces spontaneous lipid accumulation in a dose-dependent effect.

Figure 11B:
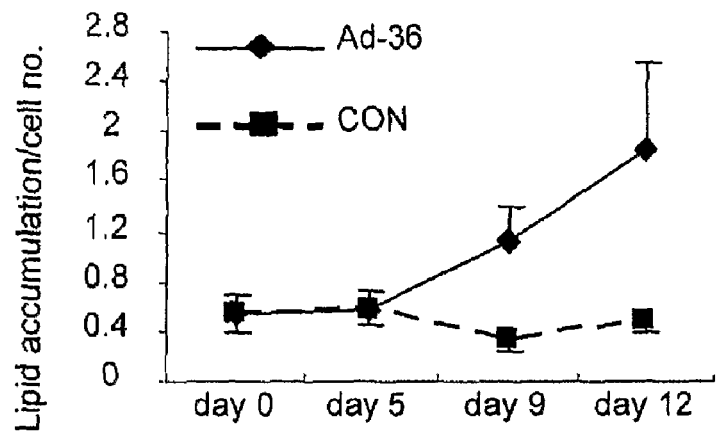
FIG. 11B illustrates the temporal change up to 12 days in lipid accumulation (determined by Oil Red-O staining) in hASC inoculated with either Ad-36 (MOI 2.7) or media (CON).

As shown in FIG. 11B, Ad-36 significantly increased lipid accumulation in hASC 9 ($p<0.01$) and 12 days ($p<0.01$) post-infection as determined by Oil Red-O assay. Similar results were obtained in hASC obtained from 3 donors belonging to a different age and BMI category, showing that Ad-36 is capable of inducing lipid accumulation in hASC.

Figure 11C:
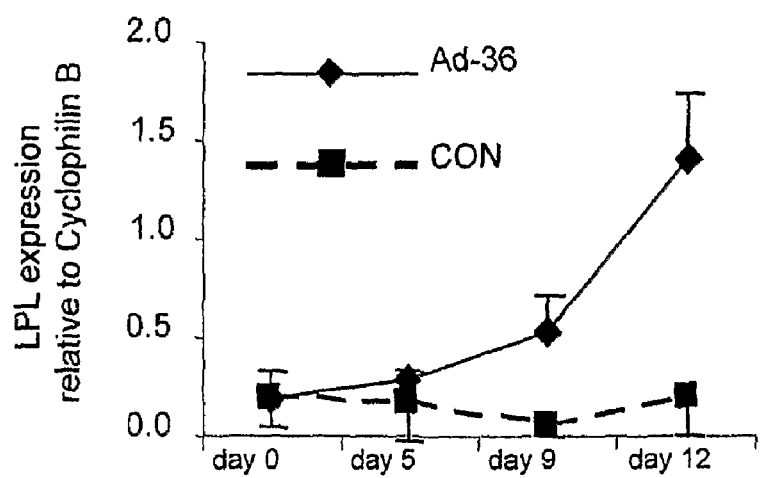
FIG. 11C illustrates the temporal change up to 12 days in lipoprotein lipase (LPL) expression in hASC inoculated with either Ad-36 (MOI 2.7) or media (CON).

Adipose lipoprotein lipase (LPL) is involved in uptake of triglycerides into adipocytes. By increasing lipid uptake from the diet, over expression of LPL increases lipid accumulation in adipocytes. Therefore, LPL was measured in hASC. Greater LPL expression was observed in hASC infected with Ad-36. FIG. 11C illustrates that hASC expressed significantly higher levels of LPL 9 days ($p<0.05$) and 12 days ($p<0.01$) post-inoculation with Ad-36, in the absence of induction cocktail, as determined by qRT-PCR. Over expression of LPL in the infected group indicates that Ad-36 stimulates dietary lipid incorporation into adipocytes, contributing to increased lipid accumulation demonstrated above lipid accumulation.

Figure 11D:
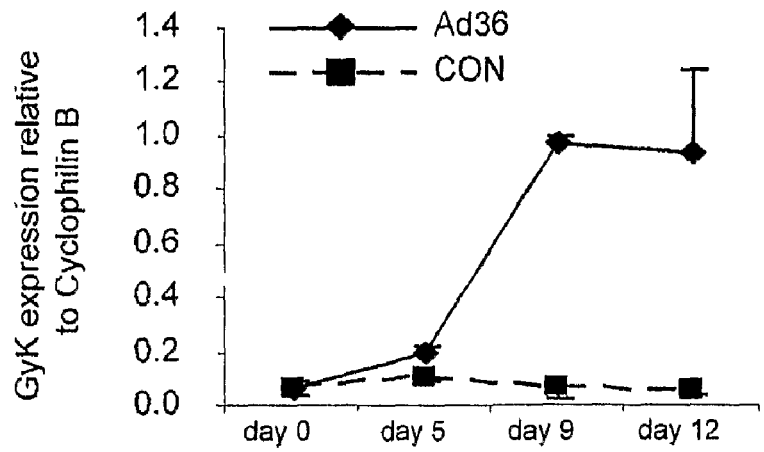
FIG. 11D illustrates the temporal change up to 12 days in glycerol kinase (GyK) expression in hASC inoculated with either Ad-36 (MOI 2.7) or media (CON).
Figure 11E:
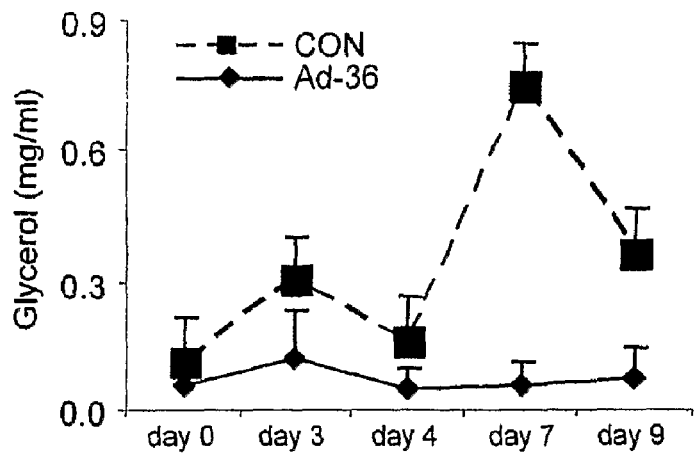
FIG. 11E illustrates the temporal change in glycerol release from hASC up to 9 days after inoculation with either Ad-36 (MOI 2.7) or media (CON).

Adipose glycerol kinase (Gk) is an enzyme responsible for triglyceride re-synthesis in adipocytes. Therefore, glycerol kinase expression was measured. As shown in FIG. 11D, glycerol kinase expression was increased with Ad-36 infection, and glycerol was decreased as measured in the media (FIG. 11E). These results suggest that Ad-36 increases lipid accumulation in adipocytes by providing greater levels of glycerol necessary for lipid synthesis.

Figure 11F:
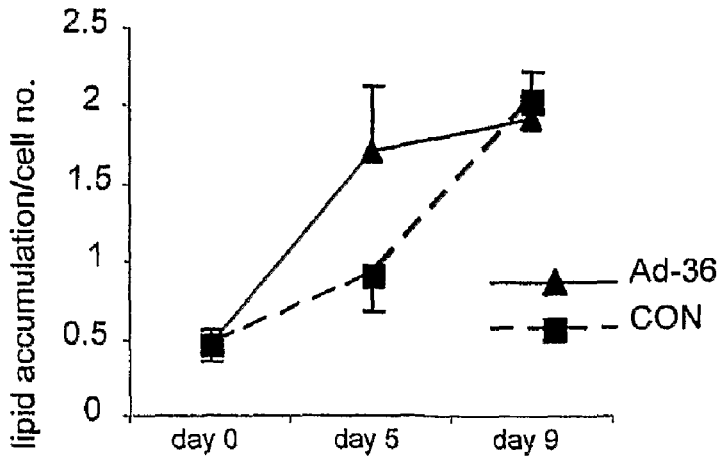
FIG. 11F illustrates the temporal change up to 9 days in lipid accumulation (determined by Oil Red-O staining) in hASC incubated with adipocyte differentiation inducers and inoculated with either Ad-36 (MOI 2.7) or media (CON).

Ad-36 induces lipid accumulation in the absence of adipocyte inductors. Experiments were conducted to determine the effect of Ad-36 on adipocyte-induced hASC, with the hypothesis that the effect of Ad-36 and differentiation inducers would be additive. Five days post-inoculation and adipocyte induction, the Ad-36 infected group showed significantly increased lipid accumulation ($p<0.01$), as determined by Oil Red-O staining normalized to cell number (FIG. 11F; n-5, mean±S.D.). However, after 9 days, lipid accumulation was similar in the two groups. These results show that Ad-36 enhances lipid accumulation in hASC in the presence of adipocyte induction agents.

Ad-36 induced commitment of hASC to adipogenic lineage, even in presence of osteogenic media. This indicates the potential use of Ad-36 in treating lipodystrophy by inducing the adipogenesis. Ad-36 also increased mRNA expression of lipoprotein lipase (LPL) and glycerol kinase (GyK), which suggests increased lipid clearance and reduced glycerol release in Ad-36 infected hASC. Moreover, infection of 3T3-

L1 cells by wild type Ad-36 as well as E4 orf 1 expression in 3T3-L1 cells, increased adiponectin secretion. Collectively, these metabolic changes are linked to improved insulin sensitivity.

EXAMPLE 5

Adipogenic Effect of Ad-36 on Human Adipose Tissue

Human adipose tissue is comprised of stem cells, adipogenic cells, endothelial cells, and immunogenic cells. In addition to the response of isolated cells of adipogenic lineage, experiments were conducted to determine the response of the entire adipose tissue to Ad-36 infection, using human adipose tissue explants (small pieces of adipose tissue cultured). Ad-36 infection of the explants induced adipogenic pathways (p38 and PI3K) and increased mRNA expressions of adipogenic (C/EBPβ and PPARγ2) and angiogenic (VEGF) genes (6).

Considering the cellular heterogeneity and the extensive interaction of the resident cell types in adipose tissue, response of the isolated cells of adipocyte lineage may not accurately reflect the in vivo response. In contrast to collagenase-based cell isolation and culturing techniques, culturing human adipose tissue explants allows manipulation and analysis of cellular interactions while the three dimensional tissue structures is maintained. Experiments were conducted to determine whether human adipose tissue explants cultures retain adipogenic, angiogenic and immunogenic characteristics, and whether the explants respond in a manner predicted by ex vivo and in vitro studies. It was found (data not shown) that human adipose tissue sections obtained from lipoaspirates and then cultured as explants in 96-well plates retain viability demonstrated by detectable expression of pro-adipogenic genes, CCAAT/enhancer binding protein β (C/EBPβ), peroxisome proliferator activator receptor γ2 (PPARγ2), adipocyte lipid binding protein (ap2), lipoprotein lipase (LPL), fatty acid synthase (FAS); angiogenic gene, vascular endothelial growth factor (VEGF); cytokines, monocyte chemoattractant protein-1 (MCP-1), macrophage inhibitory factor 1 (MIF-1) and interleukin 18 (IL-18); detectable presence of active pro-adipogenic signal transduction pathways (cAMP), phosphoinositide-3 kinase (PI3K) and p38 mitogen activated protein kinase (MAPK) as well as the presence of a monocyte lineage cell population (Western blot for HAM56).

Figure 12A:
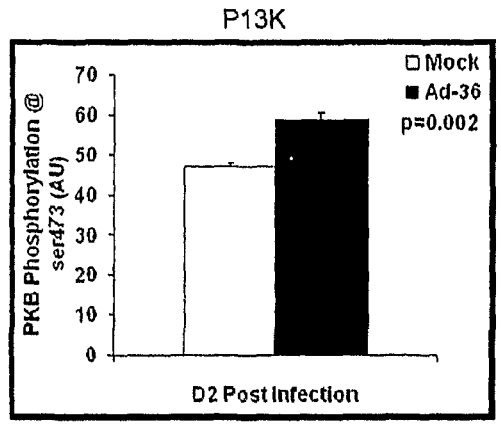
FIG. 12A illustrates the degree of protein kinase B (PKB) phosphorylation in human adipose tissue 15 days after inoculation with media (Mock) or with Ad-36 (MOI 3.8).
Figure 12B:
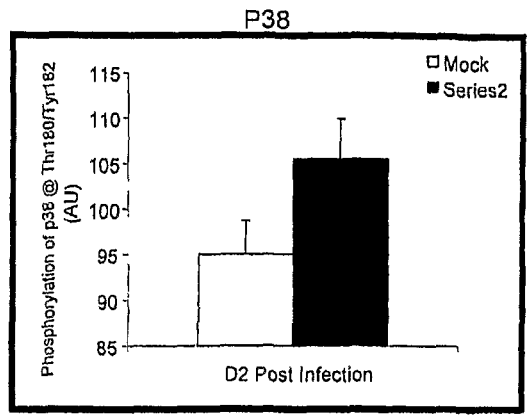
FIG. 12B illustrates the degree of p38 phosphorylation in human adipose tissue 15 days after inoculation with media (Mock) or with Ad-36 (MOI 3.8).
Figure 12C:
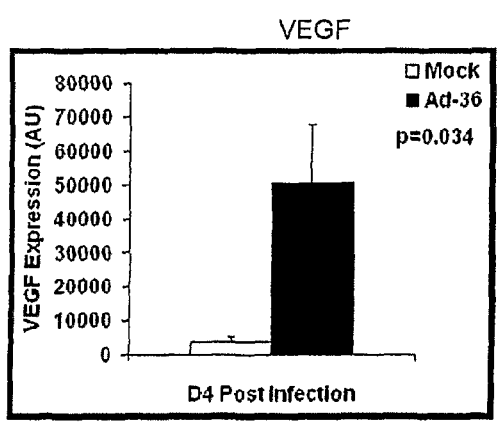
FIG. 12C illustrates the degree of vascular epithelial growth factor (VEGF) expression in human adipose tissue 4 days after inoculation with media (Mock) or with Ad-36 (MOI 3.8).
Figure 12D:
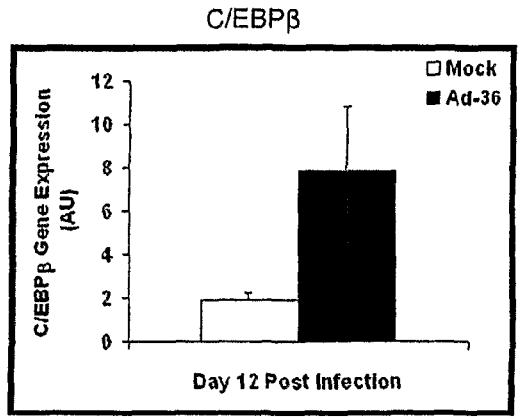
FIG. 12D illustrates the degree of CCAAT/enhancer binding protein β (C/EBPβ) expression in human adipose tissue 12 days after inoculation with media (Mock) or with Ad-36 (MOI 3.8).
Figure 12E:
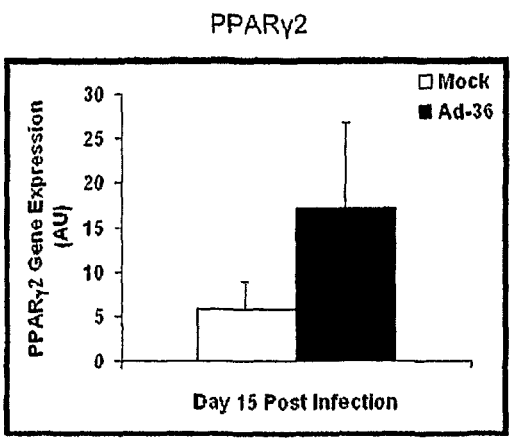
FIG. 12E illustrates the degree of peroxisome proliferator activator receptor γ2 (PPARγ2) expression in human adipose tissue 15 days after inoculation with media (Mock) or with Ad-36 (MOI 3.8).

To assess the effect of Ad-36 infection on human adipose tissue, explants were infected with Ad-36. The infected explants showed strong and increasing expression of viral genes confirming an active viral infection. Similar to the results with cultured hASCs infected with Ad-36, the viral infection up-regulated pro-adipogenic signal transduction pathways PI3K (FIG. 12A; day 2 post infection) and p38 (FIG. 12B; day 2 post infection), as indicated by increased phosphorylations of PKB and p38, respectively, followed by significant increases in pro-adipogenic (C/EBPβ (FIG. 12D; day 12 post infection) and PPARγ2 (FIG. 12E; day 15 post infection)) and VEGF, a proangiogenic gene expression (FIG. 12C; day 4 post infection) in human adipose tissue explants. In FIGS. 7A-7E, human adipose tissue was inoculated with media (Mock) or Ad-36, and various gene expressions were determine from day 2 to day 15. The results suggest that Ad-36 is able to induce adipogenic changes in human adipose tissue. The use of adipose tissue explants minimizes the extrapolation of in vitro results obtained from studying individual cell types or using artificial co-culturing techniques.

The above-described studies showed that Ad-36 infection of human adipose tissue up-regulates PI3 kinase signaling pathway, and increases differentiation and lipid accumulation. The ability of Ad-36 to remodel adipose tissue via PI3 kinase activation was also investigated by infecting human adipose tissue explants in the presence or absence of Wortmannin (WM), a well-characterized PI3 kinase inhibitor. Adipose tissue remodeling was assessed by measuring markers for adiposity (PPARγ2, aP2), angiogenesis (PECAM-1), insulin sensitivity (adiponectin, FAS), and inflammation (MCP-1). The results are shown in Table 1. In Table 1, the Ad-36 group is compared to an uninfected control, while the Ad-36+WM group is compared to Ad-36 alone

TABLE 1

| Fold change in gene expression by qRT-PCR ($p < .05$) | | |
|---|---|---|
| | Ad-36 | Ad-36 + WM |
| PPARγ2 | 29.0 | −6.4 |
| aP2 | 106.0 | −80.3 |
| PECAM-1 | 19.0 | −34.8 |
| adiponectin | 8.7 | −2.2 |
| FAS | 3.3 | −2.0 |
| MCP-1 | −19.0 | 9.3 |

Collectively, the results in Table 1 suggest that Ad-36 remodels human adipose tissue to exhibit increased adipogenesis, angiogenesis, insulin sensitivity and favorable inflammatory cytokine profile, which requires PI3 kinase activity. Potential of Ad-36 to remodel adipose tissue may provide an effective therapeutic mechanism to remodel an unfavorable adipose tissue profile common in obesity, diabetes and metabolic syndrome.

EXAMPLE 6

Ad-36 Induces Coordinated Reduction in Inflammation

Inflammatory cytokines such as MCP-1 increase insulin resistance, and reduction in their levels improves insulin sensitivity (65). Ad-36 infection was observed to rapidly decrease pro-inflammatory cytokine production (MCP-1, IL-6, IL-18) and increases anti-inflammatory (MIF-1) expression in hASC and adipose tissue explants in vitro and rats in vivo. Ad-2, a non-adipogenic adenovirus did not suppress inflammatory response.

Adipose tissue growth is associated with increased in inflammatory cytokines. Due to the association of proinflammatory cytokines with diabetes and other comorbidities, understanding the regulation of adipose tissue induced proinflammatory response is critical. Experiments were conducted to test whether Ad-36 reduced an inflammatory response of adipose tissue and adipocytes, which may contribute to Ad-36 induced insulin sensitivity. hASC from a healthy donor (BMI=25) were infected with either Ad-36 or Ad-2 (MOI=3.8). Ad-2 is a non-adipogenic human adenovirus used as a negative control. On day 1, mRNA expression of macrophage migration inhibitory factor (MIF) was significantly higher in Ad-36 infection and significantly lower in Ad-2 infection, suggesting that Ad-36 suppresses the recruitment of macrophages, while Ad-2 promotes macrophage recruitment (see Table 2). By day 2, monocyte chemoattractant protein-1 (MCP-1) and IL-18 mRNA expression were both significantly lower in the Ad-36 infected group, indicating that a coordinated immune suppression is induced by Ad-36 infection in isolated cells of adipocyte lineage. To determine the anti-inflammatory response of Ad-36 in adipose tissue, human adipose tissue explants obtained by lipoaspiration were infected with Ad-36. Similar to the findings in hASC, the Ad-36 infected group showed greater MIF and lower MCP-1 mRNA expression as compared to the uninfected control (Table 2). To determine the in vivo impact of Ad-36 induced modulation of inflammation, 5-week-old male Wistar rats were inoculated intranasally either with media, UV-inactivated Ad-36, or replication competent Ad-36. Four days later, serum IL-6 levels were found to be reduced in both viral infected groups, indicating a receptor mediated immune suppression (Table 2). However, IL-18 and MCP-1 levels were significantly reduced in replication competent Ad-36 infection alone, indicating that active viral replication is required for these effects. These data indicate that Ad-36 is able to rapidly induce coordinated reduction in inflammation, which may play a direct role in modulation of adiposity and insulin sensitivity.

TABLE 2

Percent mRNA* or protein** compared to the respective uninfected control groups. Data are expressed as Mean % change (p value).

|  | MCP-1 | MIF | IL-18 | IL-6 |
|---|---|---|---|---|
| hASC*: Ad-36 infected | 42% (p < 0.003) | 154% (p < 0.001) | 79% (p < 0.007) | N/A |
| hASC*: Ad-2 infected | 136% (p < 0.05) | 51% (p < 0.03) | 94% (p = NS) | N/A |
| hAT explants* Ad-36 infected | 70% (p < 0.07) | 167% (p < 0.056) | 113% (P = NS) | N/A |
| Rat serum** Ad-36 infected | 52% (p < 0.05) | N/A | 51% (p < 0.005) | 22% (p = NS) |

TABLE 2-continued

Percent mRNA* or protein** compared to the respective uninfected control groups. Data are expressed as Mean % change (p value).

|  | MCP-1 | MIF | IL-18 | IL-6 |
|---|---|---|---|---|
| Rat serum** UV Inactivated Ad-36 | 92% (p = NS) | N/A | 76% (p < 0.054) | 28% (p = NS) |

N/A; Data not available;
NS: Statistically not significant.

EXAMPLE 7

Effects of Ad-36 Not Due to "Infection"

Comparison with non-adipogenic human adenoviruses is one approach to identify the unique characteristics of Ad-36. Human adenovirus type 2 (Ad-2) is perhaps the most widespread virus, but it is non-adipogenic in animals and has not been found associated with human obesity. Since 3T3-L1 cells poorly express coxsackievirus-adenovirus receptor (CAR) used by Ad-2 for cell entry, it is unable to infect 3T3-L1 cells and promote differentiation—a possible explanation for the reported lack of adipogenic effect for Ad-2. To address the issue of cellular entry of Ad-2, 3T3-L1 cells that over express CAR (3T3-CAR) were used. Ad-36 and Ad-2 could infect 3T3-CAR cells as determined by the expression of respective viral genes. These results support that Ad-36 infection of 3T3-CAR significantly increases cell proliferation, PI3 kinase pathway, differentiation, and lipid accumulation over the uninfected control. (data not shown) However, none of these lipogenic effects were observed in Ad-2 infected 3T3-CAR. This experiment was repeated in human adipose derived stem cells (hASC), which support the expression of viral genes for both Ad-2 and Ad-36. Ad-36, but not Ad-2, significantly increased lipid accumulation in hASC (data not shown). Thus, the adipogenic effect of Ad-36 is not merely due to its entry in preadipocytes.

To further identify the mechanism for anti-lipogenic effect, the effects of Ad-2 on a time course of adipogenic gene expression cascade up to 7 days post infection was determined in the absence or presence of adipogenic inducers (e.g., methyl isobutyl xanthine, dexamethasone and insulin (MDI)). Ad-36 was used as an adipogenic positive control. These results are shown in Table 3.

TABLE 3

Changes in gene expression and lipid accumulation by Ad-36 and Ad-2 as compared to an uninfected control group.

|  | Wnt10b | Pref1 | C/EBPβ | C/EBPδ | C/EBPα | PPARγ2 | G3PDH | aP2 | Lipid |
|---|---|---|---|---|---|---|---|---|---|
| Ad-36 No MDI | ↓ | ↓ | ↑ | ↑ | ↑ | ↑ | ↑ | ↑ | ↑ |
| Ad-2 No MDI | ND | ↓ | ND | ND | ↓ | ND | ↓ | ↓ | ↓ |
| Ad-36 + MDI | ↓ | ↓ | ↑ | ↑ | ↑ | ↑ | ↑ | ↑ | ↑ |
| Ad-2 + MDI | ND | ND | ND | ND | ↓ | ↓ | ↓ | ↓ | ↓ | p < .05 for all changes noted.
ND: no difference vs uninfected control.

Ad-2 infected groups had significantly lower lipid accumulation even in the presence of MDI. (Table 3). These findings indicate a distinct pattern of cellular gene modulation by Ad-36, which may contribute to its phenotypic effects. Non-adipogenic human adenovirus Ad-2 is not lipogenic in 3T3-L1 cells or hASC, despite successful infection of these cells by the virus. Thus, the observed effects of Ad-36 are not simply due to an "infection", but more specific to the viral proteins made by Ad-36.

EXAMPLE 8

Ad-36 and Ad-36 E4 orf-1 Increase Adiponectin

Figure 13A:
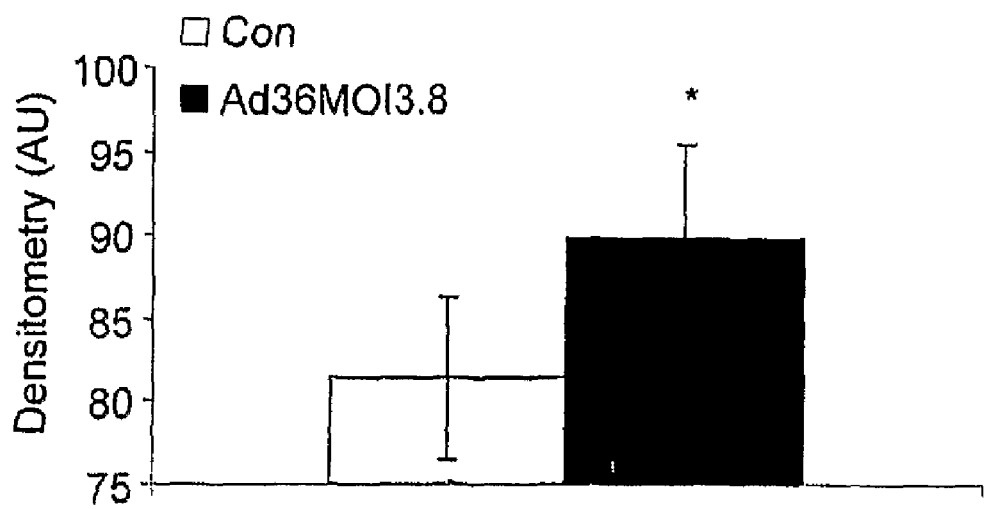
FIG. 13A illustrates the amount of adiponectin secretion from 3T3-L1 cells 7 days after inoculation with Ad-36 (MOI 3.8) or with media (CON).
Figure 13B:
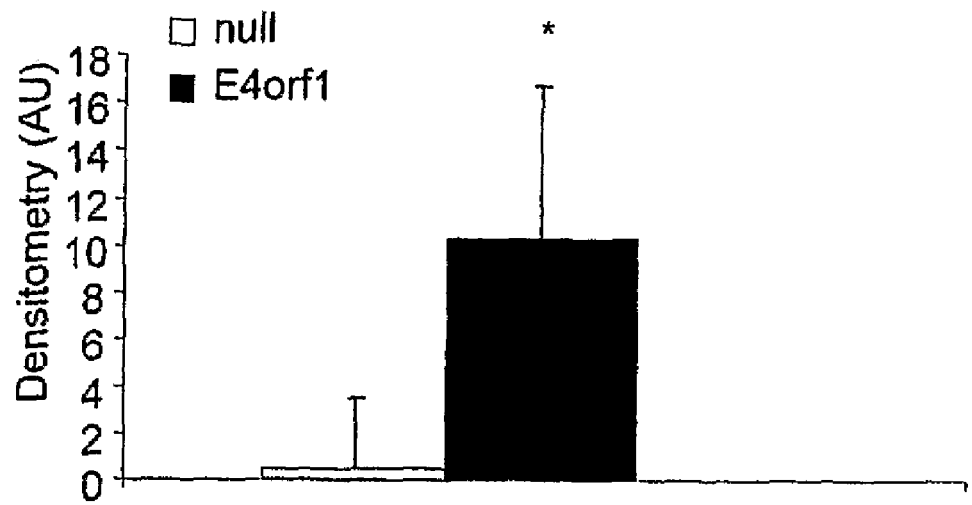
FIG. 13B illustrates the amount of adiponectin secretion from 3T3-L1 cells that either expressed E4 orf 1 or had no expression of E4 orf 1 (null) 7 days after inoculation with Ad-36 (MOI 3.8)

Adiponectin concentration was measured in media from 3T3-L1 cells 7 days after inoculation with Ad-36. The amount of adiponectin was significantly greater in the Ad-36 group as compared to the uninfected control group (p<0.04). (FIG. 13A). In addition, 3T3-L1 cells expressing only the Ad-36 E4 orf 1 gene showed greater adiponectin secretion in media, indicating a role of E4 orf 1 in modulating the secretion of adiponectin. (FIG. 13B). Thus, compared to the uninfected control, 3T3-L1 cells infected with Ad-36 showed 12-fold greater adiponectin expression (P<0.001). In addition, aquporin-7 levels increased 37% in preadipocytes, but deceased 19% in adipocytes infected with Ad-36. (data not shown) As expected, Ad-36 increased intra-cellular glycerol levels (p<0.05) and reduced glycerol release to the media to 0.25 fold. The results indicate that increased adiponectin and reduced glycerol release due to aquaporin-7 suppression may contribute to the insulin sensitizing effect of Ad-36, while increasing lipid accumulation in adipocytes.

Thus, Ad-36 wild type and its E4 orf 1 gene increase adiponectin secretion from fat cells, which indicates a role for the virus or for the E4 orf 1 gene (or protein) in increasing insulin sensitivity.

EXAMPLE 9

Ad-36 Infection Increases Differentiation and Glucose Uptake in Skeletal Muscle Cells Skeletal muscle plays an important role in glucose clearance and insulin sensitivity. A limiting step in this process is glucose transport, which is mediated by different glucose transporters. GLUT1 is responsible for basal transport and GLUT4 is responsible for insulin- or exercise-stimulated glucose transport through translocation to the plasma membrane (66). Therefore, in addition to its effect on adipose tissue and adipocytes, the effect of Ad-36 on glucose uptake by skeletal muscle was determined. As described below, we have shown that Ad-36 is capable of infecting human skeletal muscle and promoting differentiation of myoblasts. Ad-36 increases abundance of PI3K, glut 4 and glut 1 transport proteins, and. increases glucose uptake in both diabetic and non-diabetic human skeletal muscle. The increased glucose uptake appears to be independent of insulin signaling.

Human skeletal muscle cell culture. The methods for muscle biopsy and cell isolation and growth are as described (67). Muscle biopsies were obtained from the vastus lateralis muscle by the needle biopsy procedure from type 2 diabetes subjects and a lean subject. Approximate 100 mg muscle tissue was minced with surgical scissors and digested by 0.55% trypsin and 2.21 mM EDTA with constant shaking at 37° C. After centrifuging to remove fat and debris, myoblasts were grown in a monolayer culture in skeletal muscle growth medium (SkGM) from Cambrex Co (Walkersville, Md.) with 10% (v/v) fetal bovine serum, 1% (v/v) antibiotics (10,000 units/ml of penicillin G and 10 mg/ml streptomycin), 2 mM glutamine, and 25 mM Hepes (pH 7.4).

Infection of HSKM cells with Ad-36 virus. The myoblast cells were maintained in skeletal muscle growth media with 10 FBS to 80% confluence. The cells were infected with either Ad-36 or Ad-2 at the stated doses for 1 hour. The Ad-2 infected cells were used as a control group. After the hour, the cells were washed and fresh media added. A successful infection of cells was ascertained by determining viral gene expression by qPCR as shown above.

Real-time RT-PCR assay analysis: Total RNA from hSKM cells was isolated with TRIzol reagent (Invitrogen) according to the manufacturer's protocol, and further purified by RNeasy Mini Kit from Qiagen (Md.).

Western Blotting analysis. Whole cell lysates were prepared as previously described (68). Membranes were incubated with polyclonal or monoclonal antibodies that recognize MyoD, Myogenin, M-cadherin, IRS-1, IRS-2, IR β, PI 3, Akt-p, Ras, Glut 1, Glut 4 and β-actin antibodies respectively. Following corresponding secondary antibody conjugated with horseradish peroxidase, signals were detected by enhanced chemiluminescence solution. The specific bands were quantitated with scanning densitometry, and the data were normalized to β-actin levels.

2-Deoxy-D-glucose Uptake. hSKM cells were infected with various doses of Ad-36 virus for up to 5 days. Vehicle (Saline) or Insulin (100 nM) were added during the last 15 min of incubation. Cells were washed twice using PBS, and glucose uptake was performed as previously described (69). Briefly, muscle cells were cultured in 24-well plates at $5\times10^5$ cells/well in SkMG media which contained 5 mM glucose and 2% calf serum for 24 h at 37° C. The culture medium was replaced with serum-free, glucose- and pyruvate-free skeletal muscle cell basal medium (no growth factors) containing 10 μCi/ml [$^3$H]2DG 500 μl/well (Perkin Elmer life Sciences, Boston, Mass.). Then the wells were incubated for 7 min at room temperature. Subsequently, the medium was removed by aspiration, and the cells were washed three times with cold PBS. The cells were then lysed with 500 μl/well 0.2 N NaOH for 15 min. Cell lysate (400 μl) was transferred from each well plate to a scintillation vial, and the radioactivity determined by scintillation counting. All experiments were performed in triplicate with at least three different donors of muscle cells.

IRS-1 and IRS-2 associated PI3 kinase activity assays: A total of 1 mg of protein from the muscle cell lysates was immunoprecipitated with 4 μg of IRS-1 polyclonal antibody to determine IRS-1-associated PI3 kinase activity, as previously described (70) The PI3 kinase phosphate product was visualized by autoradiography, and quantified by scanning densitometry.

Figure 14A:
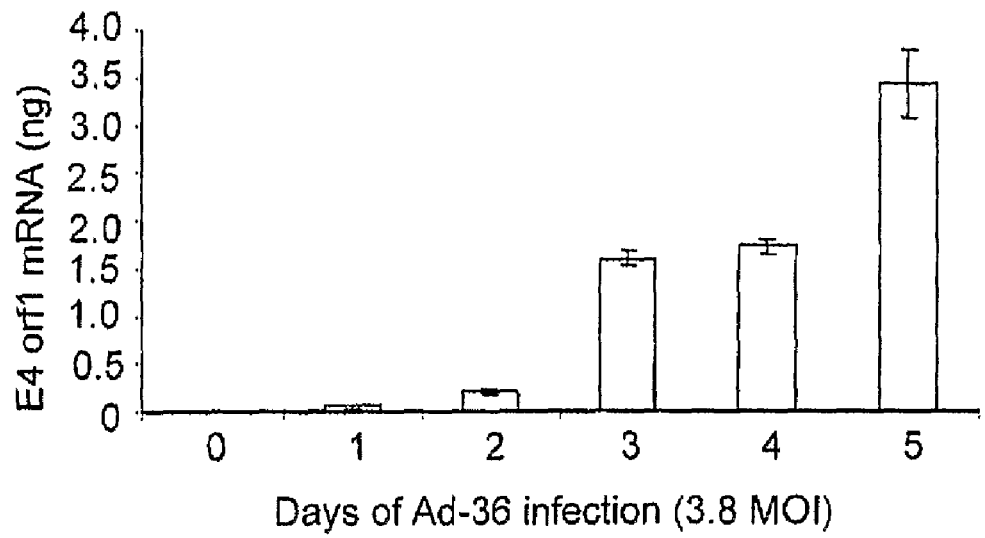
FIG. 14A illustrates the temporal change in Ad-36 E4 orf-1 gene expression in human skeletal muscle cells (hSKM) up to 5 days after inoculation with Ad-36 (MOI 3.8).
Figure 14B:
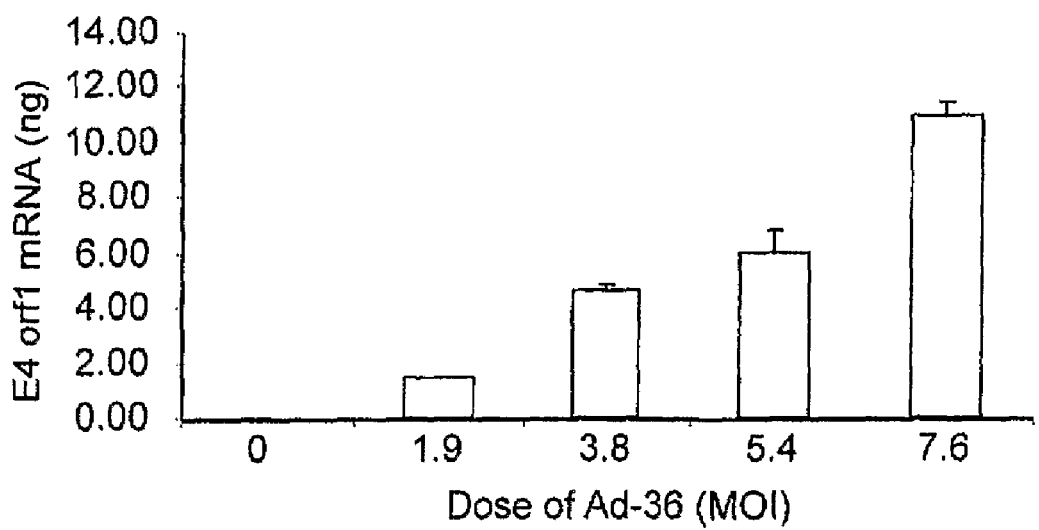
FIG. 14B illustrates the dose-dependent change in Ad-36 E4 orf-1 gene expression in human skeletal muscle cells 5 days after inoculation with Ad-36 at MOI of about 1.9 to about 7.6.

Ad-36 can infect human skeletal muscle (hSKM) cells. Using real time PCR assay, E4 orf 1 gene expression was measured in Ad-36 infected HSKM cells. Muscle cells isolated from muscle biopsies from human subjects (67) were inoculated with or without Ad-36 for up to 5 days. As shown in FIG. 14A, Ad-36 E4 orf 1 mRNA increased with time with Ad-36 infection of MOI of 3.8. In addition, different doses of Ad-36 infection were tried (MOI from about 1.9 to about 7.6). As shown in FIG. 14B, E4 orf 1 mRNA increased with dose. The data shown in FIGS. 14A and 14B were the results of triplicate measurements and represent a mean±SEM.

Figure 15:
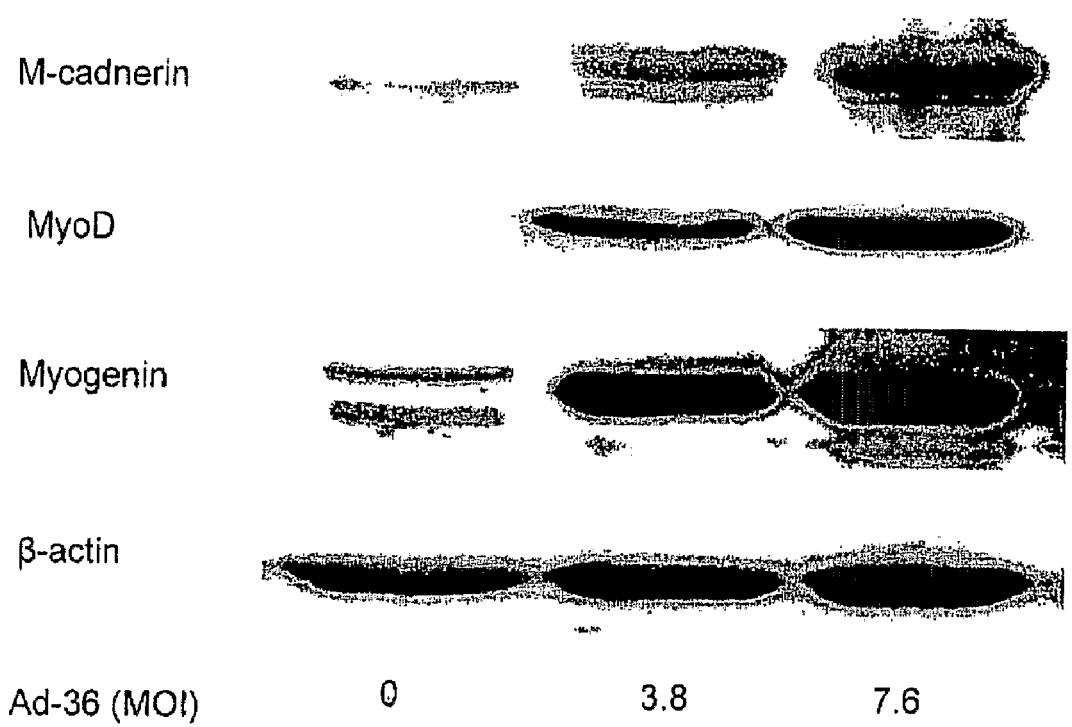
FIG. 15 illustrates the degree of expression using Western Blot analysis for several proteins involved in muscle cell differentiation (M-cadnerin, MyoD, Myogenin) in clysates of human skeletal muscle cells 7 days after inoculation with Ad-36 (either MOI 3.8 or MOI 7.6), using β-actin expression as a control.

Ad-36 enhanced myoblasts differentiate into myotubes. Using a Western blot analysis for various muscle proteins, Ad-36 infected cells were shown to have significantly increased M-cadnerin, Myogenin and MyoD proteins at day 7 of post Ad-36 infection. The concentrations increased with the higher dose of MOI of 7.6 (FIG. 15). These proteins signify a differentiation from myoblasts to myotubes.

Figure 16A:
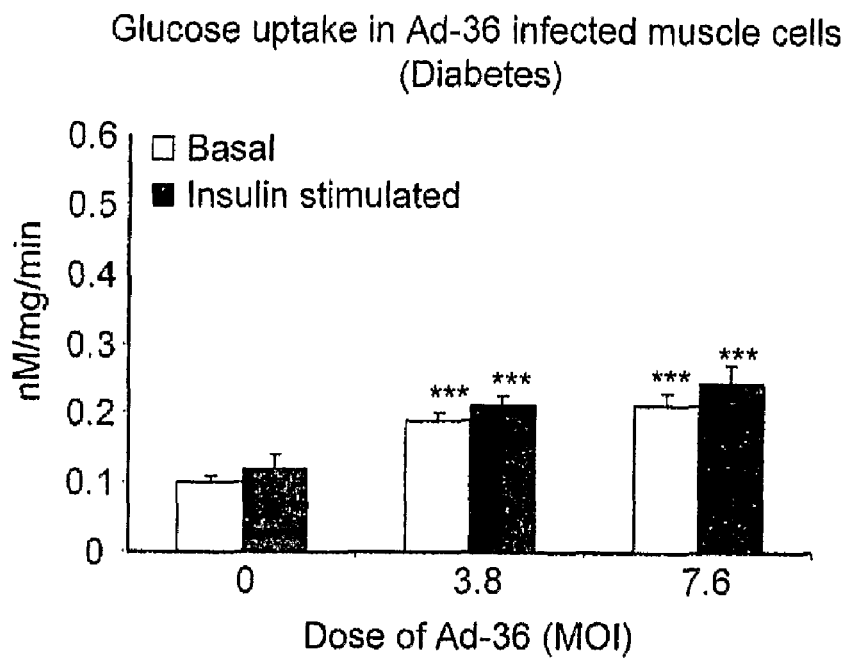
FIG. 16A illustrates the degree of glucose uptake in skeletal muscle cells isolated from diabetic human subjects 24 h after infection with Ad-36 (either MOI 3.8 or 7.6), and incubated with either plain media (Basal) or with insulin (Insulin stimulated).
Figure 16B:
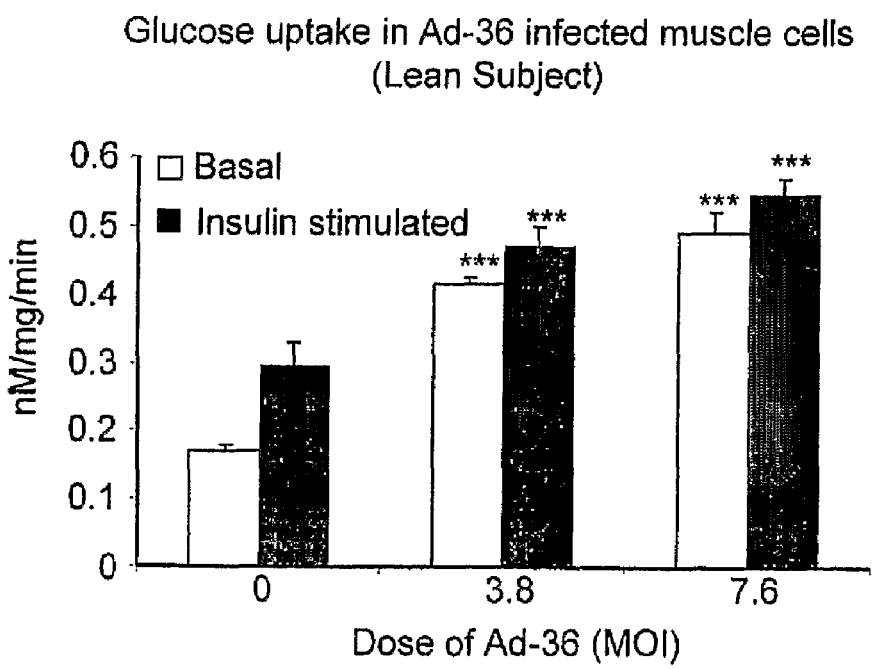
FIG. 16B illustrates the degree of glucose uptake in skeletal muscle cells isolated from non-diabetic, lean human subjects 24 h after infection with Ad-36 (either MOI 3.8 or 7.6), and incubated with either plain media (Basal) or with insulin (Insulin stimulated).

Ad-36 increases glucose uptake in muscle cells. 2-Deoxy glucose uptake was measured in Ad-36 infected muscle cells taken both from a diabetic subject and a lean, non-diabetic subject. The degree of uptake with and without insulin stimulation was measured in a control, as well as at two different doses of Ad-36 (MOI of 3.8 and 7.6). As shown in FIG. 16A, Ad-36 infection significantly increased both basal and insulin-stimulated glucose uptake of hSKM cells from an overweight diabetic subject as compared to the uninfected control group. In addition, similar results were seen at comparable infection levels in hSKM cells from a lean non-diabetic subject (FIG. 16B). The glucose assay was performed in triplicate, and the results in FIGS. 16A and 16B are expressed as mean+/−SEM. (***P<0.001, Ad-36 infected cells compared to uninfected control).

Figure 17:
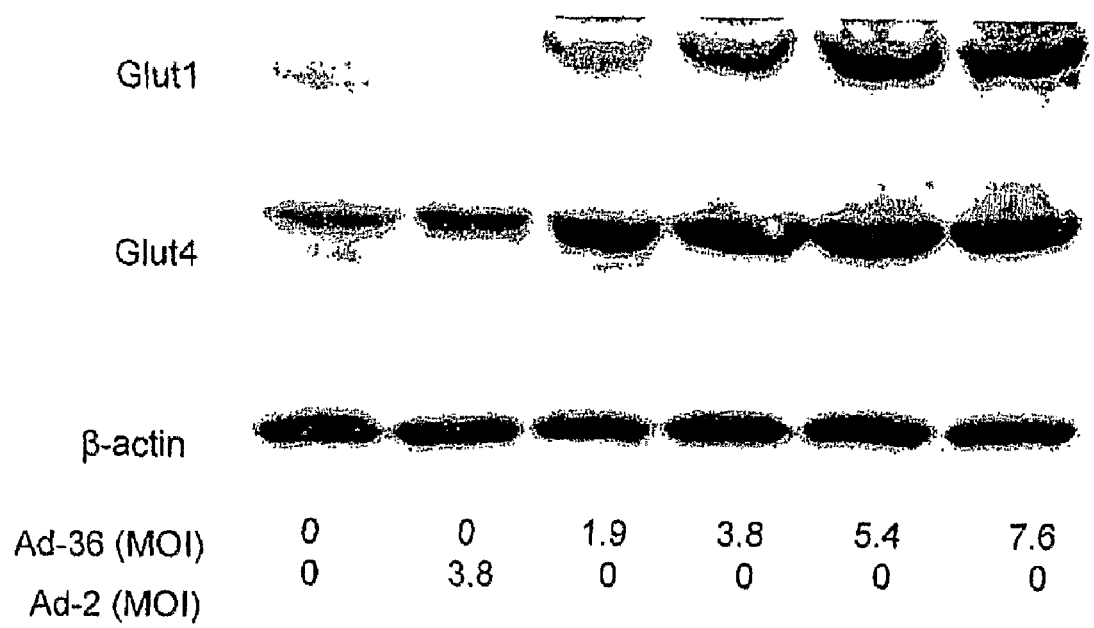
FIG. 17 illustrates the degree of either Glut1 or Glut 4 protein expression in human skeletal muscle cells using Western Blot analysis 7 days after inoculation with either Ad-36 (MOI from about 1.9 to about 7.6) or Ad-2 (MOI 3.8), using β-actin expression as a control.

Ad-36 increases GLUT1 and GLUT4 gene expression and proteins in hSKM cells. Using a Western Blot analysis, the effect of Ad-36 and Ad-2 infection on Glut1 and Glut4 protein abundance was determined after 7 days post infection. The results are shown in FIG. 17. Ad-36 but not Ad-2 infection, significantly increased the level of both Glut1 and Glut4 proteins in a dose-dependent manner.

Figure 18A:
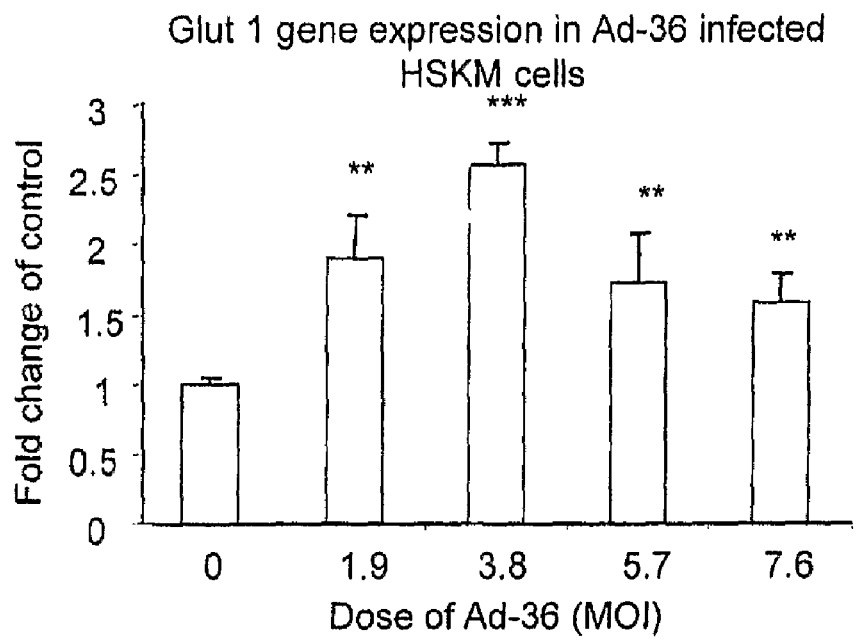
FIG. 18A illustrates the dose-dependent effect on Glut1 gene expression in human skeletal muscle cells using real time PCR assay 7 days after inoculation with either Ad-36 (MOI from about 1.9 to about 7.6) or media.
Figure 18B:
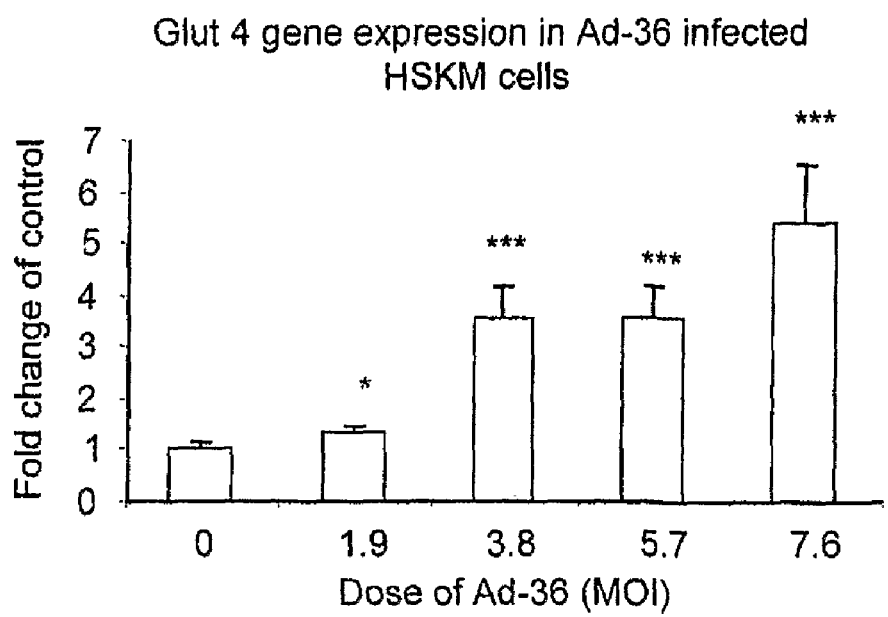
FIG. 18B illustrates the dose-dependent effect on Glut4 gene expression in human skeletal muscle cells using real time PCR assay 7 days after inoculation with either Ad-36 (MOI from about 1.9 to about 7.6) or media.

In addition, using real time PCR assay, the effect of Ad-36 infection on Glut 1 and Glut 4 gene expression was measured in hSKM cells. On day 7 post infection, Ad-36 was shown to increase gene expression of Glut1 up to a MOI of 3.8 (FIG. 18A). However, the highest expression level of Glut4 in hSKM cells was seen at a MOI of 7.6 (FIG. 18B). In FIGS. 18A and 18B, data are the mean+/−SEM of triplicate measurements. (*P<0.05, P<0.01 and *P<0.001, when comparing Ad-36 infected cells to the control).

Figure 19:
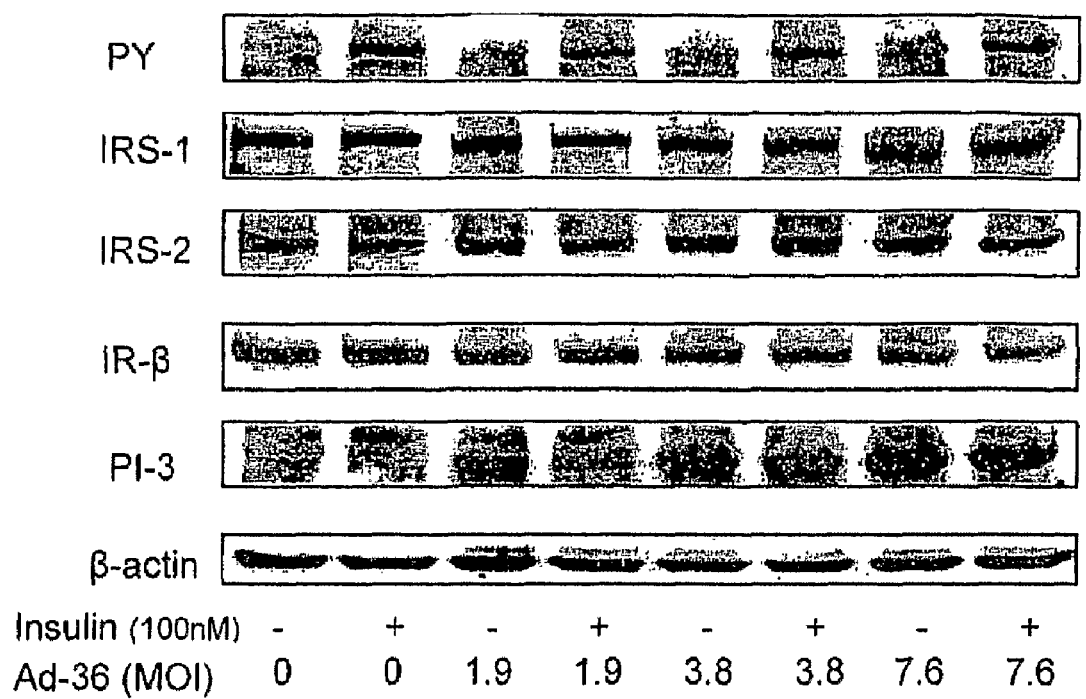
FIG. 19 illustrates the degree of expression of several proteins (PY, IRS-1, IRS-2, IR β, and PI 3K) using Western Blot analysis on cell lysates from human skeletal muscle cells 7 days after infection with either Ad-36 (MOI from about 1.9 to about 7.6) or media, and incubated either with or without insulin (100 nM), using β-actin as a control.

Ad-36 increases PI3K, but not proteins involved in insulin signaling pathway. Using a Western Blot analysis, proteins involved in the insulin signaling pathway protein analysis were measured in cells infected with Ad-36 at various concentrations for 7 days. The results are shown in FIG. 19. After 7 days post infection, equal amounts of supernatant from the infected cell lysates were subjected to 6% SDS PAGE, and then transferred to a nitrocellulose membrane. Specific antibodies against PY, IRS-1, IRS-2, IRβ, PI 3 and β-actin were added into 2% BSA TBST buffer at 4° C. overnight, and followed by a second antibody as described above. The assay was performed for three separated experiments. FIG. 19 shows that infection with Ad-36 substantially increased PI3K abundance even without insulin, but the proteins involved in insulin stimulated signaling (IRS-1 and IRS-2) were unchanged. These results indicate that Ad-36 is able to activate PI3K by an insulin independent pathway, and thus would be useful in the treatment of both type 1 and type 2 diabetes. This increase in PI3K causes an increase in cellular glucose uptake.

Figure 20:
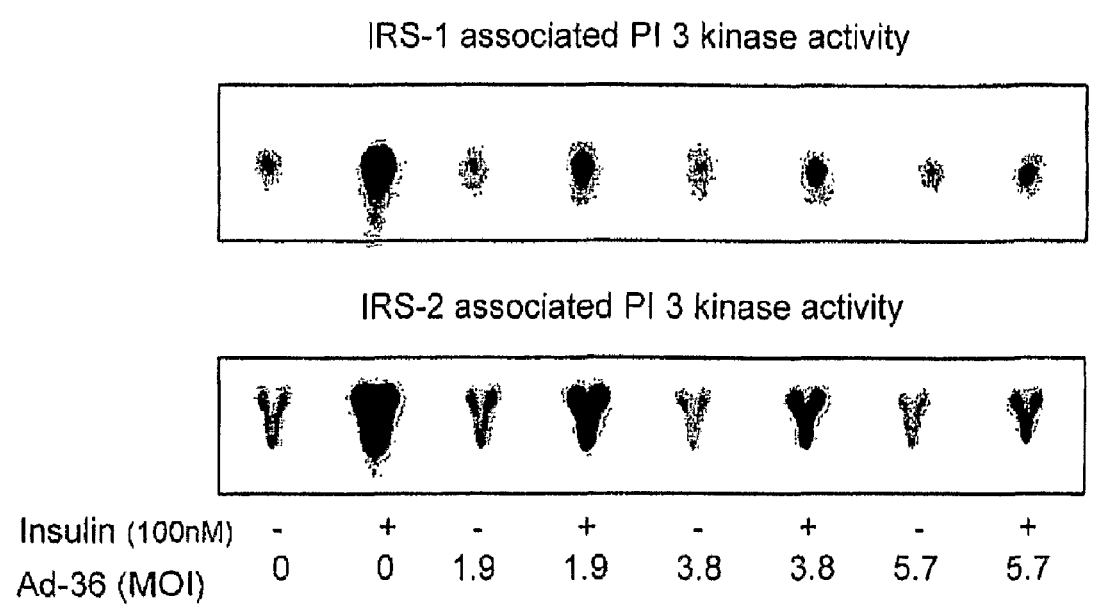
FIG. 20 illustrates the amount of PI3 kinase activity associated with either IRS-1 or IRS-2 by using immunoprecipitation followed by a PI3 kinase activity assay on cell lysates from human skeletal muscle cells 7 days after infection with Ad-36 (MOI from about 1.9 OI to about 7.6) or media, and incubated either with or without insulin (100 nM).

To further elucidate the changes in PI3K, on day 7 post Ad-36 infection, hSKM cells were harvested and homogenized. After centrifugation, 400 ug supernatant was immunoprecipitated with 3 ug of either IRS-1 or IRS-2 antibody (Upstate Biotech, Lake Placid, N.Y.). PI3 kinase activity was then assayed for a duplicate of three separate experiments. The results are shown in FIG. 20, which indicates that PI3K is activated by complexing with IRS-1 and IRS-2 in response to insulin induction. However, PI3K activation due to Ad-36 infection does not occur by complexing with IRS-1 and IRS-2. Once again, these results support that Ad-36 is able to induce PI3K activation, independent of insulin signaling.

Figure 21:
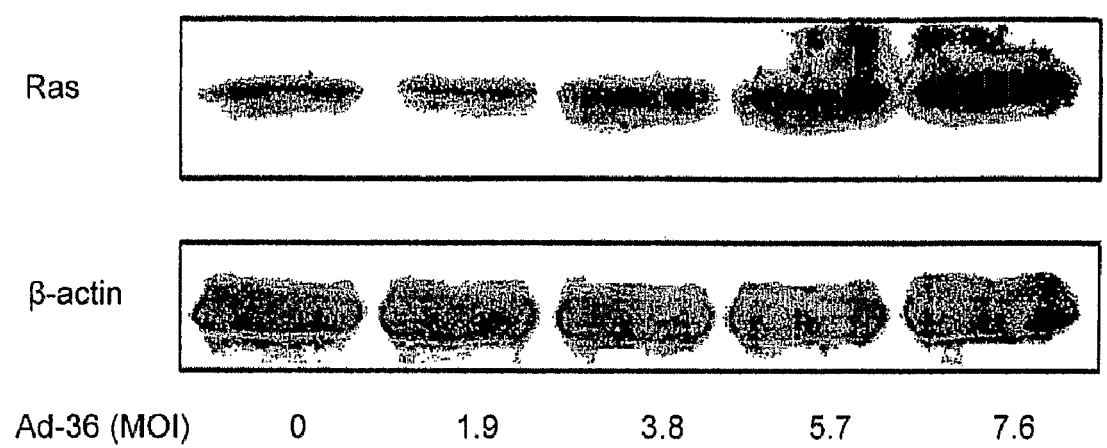
FIG. 21 illustrates the degree of RAS protein expression using Western Blot analysis on cell lysates from human skeletal muscle cells 7 days after infection with Ad-36 (MOI from about 1.9 OI to about 7.6) or media, and incubated either with or without insulin (100 nM).

Ad-36 infection increases RAS protein abundance. The effect of Ad-36 infection on RAS activation in hSKM cells was measured using Western Blot analysis. hSKM cells were infected with various doses of Ad-36 (MOI from about 1.9 to about 7.6). The results are shown in FIG. 21, which indicates a dose-dependent increase in abundance of RAS protein. RAS is a protein known to activate PI3K. These results suggest that the effect of Ad-36 infection on PI3K activation is through an increase in the RAS protein.

Ad-36 was shown to increase differentiation and insulin independent glucose uptake in primary human skeletal muscle cells (hSMC). The baseline glucose uptake by hSMC obtained from type 2 diabetic subjects was lower than that of non-diabetic subjects. However, Ad-36 infection increased glucose uptake in cells obtained from diabetic as well as non-diabetic subjects. Ad-36 increased glut4 expression and protein abundance, which is involved in glucose uptake by cells. Future experiments will test the effect of infection with the Ad-36 E4 orf 1 gene. It is expected, based on the results using adipose tissue cells, that the E4 orf 1 gene will increase differentiation and glucose uptake in muscle cells.

Miscellaneous

The term "Ad-36 E4 orf 1 protein" used herein and in the claims refers to the peptide as shown in SEQ ID NO. 2, its derivatives and analogs. The terms "derivatives" and "analogs" are understood to be compounds that are similar in structure to Ad-36 E4 orf 1 protein and that exhibit a qualitatively similar effect on insulin sensitivity, on angiogenesis, or on glycerol release as does the unmodified Ad-36 E4 orf 1 protein.

The term "therapeutically effective amount" as used herein refers to an amount of Ad-36 E4 orf 1 protein or its agonists sufficient to either increase insulin sensitivity, promote cell differentiation (adipose or muscle), promote lipid accumulation in adipose tissue, and promote glucose uptake in muscle cells to a statistically significant degree (p<0.05). The dosage ranges for the administration of Ad-36 E4 orf 1 protein are those that produce the desired effect. Generally, the dosage will vary with the age, weight, condition, and sex of the patient. A person of ordinary skill in the art, given the teachings of the present specification, may readily determine suitable dosage ranges. The dosage can be adjusted by the individual physician in the event of any contraindications. In any event, the effectiveness of treatment can be determined by monitoring the level of insulin sensitivity by methods well known to those in the field. Moreover, Ad-36 E4 orf 1 protein can be applied in pharmaceutically acceptable carriers known in the art, including carrier molecules that target specific tissues.

The present invention provides a method of preventing, treating, or ameliorating the symptoms of insulin resistance, diabetes or of lipodystrophy, comprising administering to a subject at risk for a disease or displaying symptoms for such disease, a therapeutically effective amount of Ad-36 E4 orf 1 protein or its agonists. The term "ameliorate" refers to a decrease or lessening of the symptoms or signs of the disorder being treated.

REFERENCES

1. Rossner S. Can obesity be an infectious disease? Lakartidningen. 2005 June 13-26; 102 (24-25): 1896-8.
2. Astrup A, Lundsgaard C, Stock M J. Is obesity contagious? Int J Obes Relat Metab Disord. 1998 April; 22(4):375-6.
3. Powledge T M. Is obesity an infectious disease? Lancet Infect Dis. 2004 October; 4(10):599.
4. Dhurandhar N V, Atkinson R L and Ahmad A. Obesity of Infectious Origin: A Review. Growth, Genetics and Hormones 2004, 20(3): 33-39.

5. Dhurandhar N V, Israel B A, Kolesar J M, Mayhew G F, Cook M E and Atkinson R L. Increased adiposity in animals due to a human virus, Int J Obesity 2000; 24: 989-996.
6. Dhurandhar N V, Israel B A, Kolesar J M, Mayhew G F, Cook M E and Atkinson R L. Transmissibility of adenovirus-induced adiposity in a chicken model. Int J Obesity 2001; 25: 990-996.
7. Dhurandhar N V, Whigham L D, Abbott D H, Schultz-Darken N J, Israel B A, Bradley S M, Kemnitz J W, Allison D B, and Atkinson R L. Human Adenovirus Ad-36 Promotes Obesity in Male Rhesus and Marmoset Monkeys. J Nutrition 2002, 132:3155-3160.
8. Atkinson R L, Dhurandhar N V, Allison, D B, Bowen R L, Israel B A, Albu J B, and Augustus A S. Human adenovirus-36 is associated with increased body weight and paradoxical reduction of serum lipids International Journal of Obesity 2005 29:281-286.
9. Vangipuram S D, Sheele J, Atkinson R L, Holland T C, and Dhurandhar N V. A Human Adenovirus Enhances Preadipocyte Differentiation. Obesity Research 2004; 12:770-777 (reprint attached).
10. Bernard A, Zwingelstein G, Meister R and Fabian Wild T. Hyperinsulinemia induced by canine distemper virus infection of mice and its correlation with the appearance of obesity. Comp Biochem Physiol, 1988; 91B:691-696.
11. Bernard A, Fevre-Montange M, Giraudon P, Hardin H, Fabian Wild T and Belin M F. Localization of viral proteins and RNA in hypothalamus of mice infected by canine distemper virus (French). Virology 1991; 313:545-551.
12. Bernard A, Fevre-Montange M, Bencsik A, Giraudon P, Fabian Wild T, Confavreux C and Belin M F. Brain structures selectively targeted by canine distemper virus in a mouse model infection. J Neuropath Exp Neuro 1993; 52:471-480.
13. Carter J K, Ow C L and Smith R E. Rous-Associated virus type 7 induces a syndrome in chickens characterized by stunting and obesity. Infection and Immunity 1983; 39:410-422.
14. Carter J K, Garlich J D, Donaldson W T and Smith R E. Influence of diet on a Retrovirus induced obesity and stunting syndrome. Avian Dis, 1983; 27:317-322.
15. Dhurandhar N V, Kulkarni P R, Ajinkya S M and Sherikar A A. Avian adenovirus leading to pathognomic obesity in chickens. J Bombay Vet College, 1990; 2:131-132.
16. Dhurandhar N V, Kulkarni P R, Ajinkya S M and Sherikar A A. Effect of adenovirus infection on adiposity in chickens. Veterinary Microbiology, 1992; 31:101-107.
17. Dhurandhar N V, Kulkarni P R, Ajinkya S M, Sherikar A A and Atkinson R L. Screening of human sera for antibody against avian adenovirus. Obesity Research 1997; 5:464-469.
18. Gosztonyi G and Ludwig H. Borna disease: Neuropathology and pathogenesis. Current Topics in Microbiology and Immunology 1995; 190:39-73.
19. Lyons M J, Faust I M, Hemmes R B, Buskirk D R, Hirsch J and Zabriskie J B. A virally induced obesity syndrome in mice. Science 1982; 216:82-85.
20. So P W, Herlihy A H, Bell J D. Adiposity induced by adenovirus 5 inoculation. Int J Obes Relat Metab Disord. 2005 June; 29(6):603-6.
21. Foy H M and Grayston J T. 1976. Adenoviruses. In "Viral infections of humans: Epidemiology and control". Evans Alfred S. Ed. Plenum Medical. New York, pp 53-70.
22. Foy H M and Grayston J T. 1976. Adenoviruses. In "Viral infections of humans: Epidemiology and control". Evans Alfred S. Ed. Plenum Medical. New York, pp 53-70.
23. Horvath J, Palkonyay I, Weber J. Group C adenovirus sequences in human lymphoid cells. J Virol 1986; 59:189-192.
24. Neumann R, Genersch E, Eggers H J. Detection of adenovirus nucleic acid sequences in human tonsils in the absence of infectious virus. Virus Res 1987; 7:93-97.
25. Hierholzer J C, Wigand R, Anderson L J, Adrian T and Gold J W M. Adenoviruses from patients with AIDS: A plethora of serotypes and a description of five new serotypes of subgenus D (Types 43-47). J Infectious Dis 1988; 158:804-813;
26. Wigand R, Gelderblom H, Wadell G. New human adenovirus (candidate adenovirus 36), a novel member of subgroup D. Arch Virology 1980; 64:225-233.
27. Pereira H G, Huebner R J, Ginsberg H S and Van Der Veen J. A short description of the adenovirus group. Virology 1963; 20:613-620.
28. Shen Y, Shenk T E. Viruses and apoptosis. Curr Opin Genet Dev. 1995; 5(1):105-11.
29. Javier, R., Raska, K., Jr., Macdonald, G. J., and Shenk, T. (1991). Human adenovirus type 9-induced rat mammary tumors. *J Virol* 65(6), 3192-202.
30. Javier, R., Raska, K., Jr., and Shenk, T. (1992). Requirement for the adenovirus type 9 E4 region in production of mammary tumors. *Science* 257(5074), 1267-71.
31. Javier, R. T. (1994). Adenovirus type 9 E4 open reading frame 1 encodes a transforming protein required for the production of mammary tumors in rats. *J Virol* 68 (6), 3917-24.
32. Thomas, D. L., Shin, S., Jiang, B. H., Vogel, H., Ross, M. A., Kaplitt, M., Shenk, T. E., and Javier, R. T. (1999). Early region 1 transforming functions are dispensable for mammary tumorigenesis by human adenovirus type 9. *J Virol* 73 (4), 3071-9.
33. Weiss, R. S., McArthur, M. J., and Javier, R. T. (1996). Human adenovirus type 9 E4 open reading frame 1 encodes a cytoplasmic transforming protein capable of increasing the oncogenicity of CREF cells. *J Virol* 70(2), 862-72.
34. Weiss, R. S., Gold, M. O., Vogel, H., and Javier, R. T. (1997). Mutant adenovirus type 9 E4 ORF 1 genes define three protein regions required for transformation of CREF cells. *J Virol* 71(6), 4385-94.
35. Nourry, C., Grant, S. G., and Borg, J. P. (2003). PDZ domain proteins: plug and play! *Sci STKE* 2003(179), RE7.
36. Latorre, I. J., Roh, M. H., Frese, K. K., Weiss, R. S., Margolis, B., and Javier, R. T. (2005). Viral oncoprotein-induced mislocalization of select PDZ proteins disrupts tight junctions and causes polarity defects in epithelial cells. *J Cell Sci* 118(Pt 18), 4283-93.
37. Frese, K. K., Lee, S. S., Thomas, D. L., Latorre, I. J., Weiss, R. S., Glaunsinger, B. A., and Javier, R. T. (2003). Selective PDZ protein-dependent stimulation of phosphatidylinositol 3-kinase by the adenovirus E4-ORF1 oncoprotein. *Oncogene* 22(5), 710-21.
38. Sakaue, H., Ogawa, W., Matsumoto, M., Kuroda, S., Takata, M., Sugimoto, T., Spiegelman, B. M., and Kasuga, M. (1998). Posttranscriptional control of adipocyte differentiation through activation of phosphoinositide 3-kinase. *J Biol Chem* 273(44), 28945-52.
39. Tomiyama, K., Nakata, H., Sasa, H., Arimura, S., Nishio, E., and Watanabe, Y. (1995). Wortmannin, a specific phosphatidylinositol 3-kinase inhibitor, inhibits adipocytic differentiation of 3T3-L1 cells. *Biochem Biophys Res Commun* 212(1), 263-9.
40. Farmer SR. Regulation of PPARgamma activity during adipogenesis. Int J Obes. 2005 Suppl 1:S13-6.

41. Gregoire F M, Smas C M and Sul H S. Understanding adipocyte differentiation. Physiological Reviews 1998 78(3): 783-809.
42. Ntambi J M, Young-Cheul K. Adipocyte differentiation and gene expression. J. Nutr. 2000, 30(12):3122S-3126S. Review.
43. Hansen J B, Zhang H, Rasmussen T H, Petersen R K, Flindt E N, Kristiansen K. Peroxisome proliferator-activated receptor delta (PPARdelta)-mediated regulation of preadipocyte proliferation and gene expression is dependent on cAMP signaling. J Biol Chem. 2001; 276(5):3175-82.
44. Reusch J E, Colton L A, Klemm D J. CREB activation induces adipogenesis in 3T3-L1 cells. Mol Cell Biol. 2000; 20(3):1008-20.
45. Chiou G Y, Fong J C. Synergistic effect of prostaglandin F2alpha and cyclic AMP on glucose transport in 3T3-L1 adipocytes. J Cell Biochem. 2005; 94(3):627-34.
46. Cornelius P, Marlowe M, Call K, Pekala P H. Regulation of glucose transport as well as glucose transporter and immediate early gene expression in 3T3-L1 preadipocytes by 8-bromo-cAMP. J Cell Physiol. 1991; 146(2):298-308.
47. Burgering B M, Coffer P J. Protein kinase B (c-Akt) in phosphatidylinositol-3-OH kinase signal transduction. Nature. 1995 Aug. 17; 376(6541):599-602.
48. Magun R, Burgering B M, Coffer P J, Pardasani D, Lin Y, Chabot J, Sorisky A. Expression of a constitutively activated form of protein kinase B (c-Akt) in 3T3-L1 preadipose cells causes spontaneous differentiation. Endocrinology. 1996 August; 137(8):3590-3.
49. Atkinson R L, Whigham L D, Kim Y C, Israel B A, Dhurandhar N V, and Strasheim A. Evaluation of human adenoviruses as an etiology of obesity in chickens. Int J Obesity 2001; 25 (suppl 2):S12.
50. Pasarica M, Mahida M, OuYang H, Yu M, Mohankumar S, Jen K-L C and Dhurandhar N V. Human adenovirus-36 (Ad-36) induces adiposity in rats. *Obesity Research* 2004, 12 (supplement): A122.
51. Dhurandhar N V, Vangipuram S, Tian J, Stanhope K, Havel P and Heydari A R. Regulation of Leptin Expression and Secretion by a Human Adenovirus. *Obesity Research* 2003, 11:A38.
52. Komers R, Vrana A. Thiazolidinediones—tools for the research of metabolic syndrome X. Physiol Res. 1998; 47(4):215-25.
53. Verges B. Clinical interest of PPARs ligands. Diabetes Metab. 2004 February; 30(1):7-12.
54. Weyer C, Foley J E, Bogardus C, Tataranni P A, Pratley R E. Enlarged subcutaneous abdominal adipocyte size, but not obesity itself, predicts type II diabetes independent of insulin resistance. Diabetologia. 2000 December; 43(12):1498-506.
55. Stern J S, Batchelor B R, Hollander N, Cohn C K, Hirsch J. Adipose-cell size and immunoreactive insulin levels in obese and normal-weight adults. Lancet. 1972 Nov. 4; 2(7784):948-51.
56. Pasarica M, Holland T C, and Dhurandhar N V. Enhanced cell cycle activation by adenovirus 36 may contribute to increased lipid accumulation in 3T3-L1 cells. FASEB J 2005, 19 (4): A70.
57. Dhurandhar N V, Israel B A, Kolesar J M, Mayhew G F, Cook M E and Atkinson R L. Increased adiposity in animals due to a human virus. Int J Obesity 2000; 24: 989-996.
58. Yamada T, Ueda M, Seno M, Kondo A, Tanizawa K, and Kuroda S. Novel Tissue and Cell Type-specific Gene/Drug Delivery System Using Surface Engineered Hepatitis B Virus Nano-particles. Current Drug Targets—Infectious Disorders, Volume 4, Number 2, June 2004, pp. 163-167 (5).
59. Farokhzad O C, Jon S, Khademhosseini A, Tran T N, Lavan D A, Langer R. Nanoparticle-aptamer bioconjugates: a new approach for targeting prostate cancer cells. Cancer Res. 2004 Nov. 1; 64(21):7668-72.
60. Virella-Lowell I, Zusman B, Foust K, Loiler S, Conlon T, Song S, Chesnut K A, Ferkol T, Flotte T R. Enhancing rAAV vector expression in the lung. J Gene Med. 2005 July; 7(7):842-50.
61. Loiler S A, Tang Q, Clarke T, Campbell-Thompson M L, Chiodo V, Hauswirth W, Cruz P, Perret-Gentil M, Atkinson M A, Ramiya V K, Flotte T R. Localized gene expression following administration of adeno-associated viral vectors via pancreatic ducts. Mol Ther. 2005 September; 12(3): 519-27.
62. Kou B, Li Y, Shi Y, Xia J, Wang X, Wu S. Gene therapeutic exploration: retrovirus -mediated soluble vascular endothelial growth factor receptor-2 (sFLK-1) inhibits the tumorigenicity of S180, MCF-7, and B16 cells in vivo. Oncol Res. 2005; 15(5):239-47.
63. de Souza C J, Eckhardt M, Gagen K, Dong M, Chen W, Laurent D, Burkey B F. Effects of pioglitazone on adipose tissue remodeling within the setting of obesity and insulin resistance. Diabetes. 2001 August; 50(8):1863-71.
64. Furnsinn C, Waldhausl W. Thiazolidinediones: metabolic actions in vitro. Diabetologia. 2002 September; 45 (9): 1211-23.
65. Kanda H et al. MCP-1 contributes to macrophage infiltration into adipose tissue, insulin resistance, and hepatic steatosis in obesity. J Clin Invest. Jun; 116(6):1494-505, 2006.
66. Douen A G, Ramlal T, Rastogi S, Bilan P J, Cartee G D, Vranic M, Holloszy J O, and Klip A. *J. Biol. Chem.* 1990 265, 13427-13430.
67. Henry R R, Abrams L, Nikoulina S, and Ciaraldi T P. Insulin action and glucose metabolism in nondiabetic control and NIDDM subjects. Comparison using human skeletal muscle cell cultures. Diabetes. 1995 44:936-946.
68. Wang Z Q, Bell-Farrow A D, Sonntag W E, Cefalu W T. Effect of age and caloric restriction on insulin receptor binding and glucose transporter levels in aging rats. Exp Gerontology. 1997 32:671-684.
69. Klip, A., G. Li, and W. Logan. Induction of sugar uptake response to insulin by serum depletion in fusing L 6 myoblase. Am. J. Physiol. 1984, 247:E291-E296.
70. Wang Z Q, Zhang X H, Russell J C, Hulver M & Cefalu W T. Chromium picolinate enhances skeletal muscle cellular insulin signaling in vivo obese, insulin-resistant JCR:LA-cp rats. J. Nutr. 2006, 136:415-420.
71. Suomalainen M, Nakano MY, Boucke K, Keller S, Greber U F (2001) Adenovirus -activated PKA and p38/MAPK pathways boost microtubule-mediated nuclear targeting of virus. Embo J 20: 1310-1319.
72. Rajala M S, Rajala R V, Astley R A, Butt A L, Chodosh J (2005) Corneal cell survival in adenovirus type 19 infection requires phosphoinositide 3-kinase/Akt activation. J Virol 79: 12332-12341.
73. Tan P H, Xue S A, Manunta M, Beutelspacher S C, Fazekasova H, et al. (2006) Effect of vectors on human endothelial cell signal transduction: implications for cardiovascular gene therapy. Arterioscler Thromb Vasc Biol 26: 462-467.

74. Frese K K, Latorre I J, Chung S H, Caruana G, Bernstein A, et al. (2006) Oncogenic function for the Dlg1 mammalian homolog of the Drosophila discs-large tumor suppressor. Embo J 25: 1406-1417.

The complete disclosures of all references cited in this specification are hereby incorporated by reference. Also incorporated by reference are the complete disclosures of the following: (1) Fusinski et al., "Induction of Adipogenesis by Activation of Cell Signaling Pathways by Adenovirus 36," an abstract and poster presentation to American Society of Microbiology, Dec. 1-4, 2004; (2) P. M. Rogers et al., "E4 orf 1 gene of adipogenic human adenovirus Ad-36 enhances cAMP and insulin signaling pathways and induces differentiation in preadipocytes," FASEB. J., vol. 20(4): A165 (2006); (3) ZQ. Wang et al., "Effect of Adenovirus-36 Infection on Aquaporins in Preadipocytes and Adipocytes," presented at American Diabetic Association, Honolulu, Hi., Sep. 16-19, 2006; (4) M. A. Rathod et al., "Human Adenovirus Ad-36 Infection Induces Differentiation and Replication of Preadipocytes," Obesity Reviews, vol. 7(suppl 2): 138 (2006); (5) M. Pasarica et al., "Induction of Differentiation in Human Preadipocytes May Contribute to Adipogenic Effect of Human Adenovirus Ad-36," Obesity Reviews, vol. 7(suppl 2):36 (2006); (6) P. M. Rogers et al., "Human Adenovirus Ad-36 via E4 orf 1 Activity Up-regulates Pro-Adipogenic Signal Transduction Pathways and Increases Lipid Accumulation in Human Adipose Derived Stem Cells," Obesity, vol. 14(9): A 13 (2006); (7) M. A. Rathod et al., "Unique properties of human adenovirus 36 contribute to its adipogenic effect," Obesity, vol. 14(9): A 52 (2006); (8) P. M. Rogers et al., "An Organotypic Culture Model of Human Adipose Tissue," abstract submitted to International Fat Applied Technology Society, Oct. 21-24, 2006, Baton Rouge, La.; (9) M. Pasarica et al., "A novel lipogenic modulator of human adipose derived stem cells: A human adenovirus," abstract submitted to International Fat Applied Technology Society, Oct. 21-24, 2006, Baton Rouge, La.; and (10) S. A. Loiler et al., "Rapid Immune Cytokine Suppression Induced by Adenovirus-36 Infection," abstract submitted to International Fat Applied Technology Society, Oct. 21-24, 2006, Baton Rouge, La. In the event of an otherwise irreconcilable conflict, however, the present specification shall control.

What is claimed:

1. An isolated protein, Adenovirus-36 E4 orf 1, whose amino acid sequence comprises SEQ ID NO: 2.

2. The protein recited in claim 1, wherein the amino acid sequence of said protein is SEQ ID NO: 2.

3. A pharmaceutical composition comprising the protein of claim 1, additional comprising a pharmaceutical and a pharmaceutically acceptable carrier.

4. A method of treating or ameliorating one or more symptoms of a disease in a mammalian patient wherein the disease is chosen from the group consisting of lipodystrophy, diabetes, and insulin resistance, said method comprising administering to the patient a therapeutically effective amount of Adenovirus-36 E4 orf 1 protein whose amino acid sequence comprises SEQ ID NO:2, wherein the patient's symptoms improve following said administering.

5. A method as in claim 4, wherein the disease is insulin resistance, and wherein the patient's insulin sensitivity increases following said administering.

6. A method as in claim 4, wherein the disease is lipodystrophy and wherein the number of adipose tissue cells in the patient increases following said administering.

7. A method as in claim 4, wherein the disease is diabetes and the symptom is a high concentration of serum glucose, and wherein the concentration of serum glucose decreases following said administering.

8. The method of claim 4, wherein the amino acid sequence of the Adenovirus-36 E4 orf 1 protein is SEQ ID NO: 2.

9. The method of claim 4, wherein a pharmaceutical composition comprising the Adenovirus-36 E4 orf 1 protein additionally comprises a pharmaceutical and a pharmaceutically acceptable carrier are administered to the patient.

* * * * *

```
                          SEQUENCE LISTING

<160> NUMBER OF SEQ ID NOS: 4

<210> SEQ ID NO 1
<211> LENGTH: 378
<212> TYPE: DNA
<213> ORGANISM: Adenovirus type 36

<400> SEQUENCE: 1
atggctgaat ctctgtatgc tttcatagat agccctggag ggatcgctcc cgtccaggaa      60
ggggctagca atagatatat cttcttttgc cccgaatctt tccacattcc tccgcatggg     120
gtgatattgc ttcacctcag agtgagcgtg ctggttccta ctggatatca gggcagattt     180
atggccttga atgactacca tgccaggggc atactaaccc agtccgatgt gatatttgcc     240
gggagaagac atgatctctc tgtgctgctc tttaaccaca cggaccgatt tttgtatgtc     300
cgcgagggcc acccagtggg aaccctgctg ctggagagag tgattttcc ttcagtgaga      360 atagccaccc tggtttag                                                    378

<210> SEQ ID NO 2
<211> LENGTH: 125
<212> TYPE: PRT
<213> ORGANISM: Adenovirus type 36

<400> SEQUENCE: 2

Met Ala Glu Ser Leu Tyr Ala Phe Ile Asp Ser Pro Gly Gly Ile Ala
1               5                   10                  15

Pro Val Gln Glu Gly Ala Ser Asn Arg Tyr Ile Phe Phe Cys Pro Glu
            20                  25                  30

Ser Phe His Ile Pro Pro His Gly Val Ile Leu Leu His Leu Arg Val
        35                  40                  45

Ser Val Leu Val Pro Thr Gly Tyr Gln Gly Arg Phe Met Ala Leu Asn
    50                  55                  60

Asp Tyr His Ala Arg Gly Ile Leu Thr Gln Ser Asp Val Ile Phe Ala
65                  70                  75                  80

Gly Arg Arg His Asp Leu Ser Val Leu Leu Phe Asn His Thr Asp Arg
                85                  90                  95

Phe Leu Tyr Val Arg Glu Gly His Pro Val Gly Thr Leu Leu Leu Glu
```

```
                    100                 105                 110
Arg Val Ile Phe Pro Ser Val Arg Ile Ala Thr Leu Val
            115                 120                 125

<210> SEQ ID NO 3
<211> LENGTH: 366
<212> TYPE: DNA
<213> ORGANISM: Adenovirus type 36

<400> SEQUENCE: 3
atggctgaat ctctgtatgc tttcatagat agccctggag ggatcgctcc cgtccaggaa       60
ggggctagca atagatatat cttcttttgc cccgaatctt tccacattcc tccgcatggg     120
gtgatattgc ttcacctcag agtgagcgtg ctggttccta ctggatatca gggcagattt     180
atggccttga tgactacca tgccagggc atactaaccc agtccgatgt gatatttgcc       240
gggagaagac atgatctctc tgtgctgctc tttaaccaca cggaccgatt tttgtatgtc     300
cgcgagggcc acccagtggg aaccctgctg ctggagagag tgattttcc ttcagtgaga      360 atatag                                                                366

<210> SEQ ID NO 4
<211> LENGTH: 121
<212> TYPE: PRT
<213> ORGANISM: Adenovirus type 36

<400> SEQUENCE: 4

Met Ala Glu Ser Leu Tyr Ala Phe Ile Asp Ser Pro Gly Gly Ile Ala
1               5                   10                  15

Pro Val Gln Glu Gly Ala Ser Asn Arg Tyr Ile Phe Phe Cys Pro Glu
            20                  25                  30

Ser Phe His Ile Pro Pro His Gly Val Ile Leu Leu His Leu Arg Val
        35                  40                  45

Ser Val Leu Val Pro Thr Gly Tyr Gln Gly Arg Phe Met Ala Leu Asn
    50                  55                  60

Asp Tyr His Ala Arg Gly Ile Leu Thr Gln Ser Asp Val Ile Phe Ala
65                  70                  75                  80

Gly Arg Arg His Asp Leu Ser Val Leu Leu Phe Asn His Thr Asp Arg
                85                  90                  95

Phe Leu Tyr Val Arg Glu Gly His Pro Val Gly Thr Leu Leu Leu Glu
            100                 105                 110

Arg Val Ile Phe Pro Ser Val Arg Ile
            115                 120
```